(12) United States Patent
Patel et al.

(10) Patent No.: US 10,822,648 B1
(45) Date of Patent: Nov. 3, 2020

(54) HYBRID MULTI-STEP NUCLEIC ACID AMPLIFICATION

(71) Applicant: Labrador Diagnostics LLC, Healdsburg, CA (US)

(72) Inventors: Pranav Patel, Fremont, CA (US); Indira Wu, San Jose, CA (US); Aaron Richardson, Palo Alto, CA (US); Zahra Kamila Belhocine, Fremont, CA (US); Josephine Lee, Hayward, CA (US); Scott Tabakman, Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 100 days.

(21) Appl. No.: 15/664,769

(22) Filed: Jul. 31, 2017

Related U.S. Application Data

(60) Provisional application No. 62/369,179, filed on Jul. 31, 2016, provisional application No. 62/368,904, filed on Jul. 29, 2016, provisional application No. 62/368,961, filed on Jul. 29, 2016, provisional application No. 62/368,995, filed on Jul. 29, 2016, provisional application No. 62/369,006, filed on Jul. 29, 2016.

(51) Int. Cl.
  *C12Q 1/68* (2018.01)
  *C12Q 1/686* (2018.01)
  *C12Q 1/6806* (2018.01)

(52) U.S. Cl.
  CPC .......... *C12Q 1/686* (2013.01); *C12Q 1/6806* (2013.01)

(58) Field of Classification Search
  None
  See application file for complete search history.

(56) References Cited

U.S. PATENT DOCUMENTS

| | | | |
|---|---|---|---|
| 6,605,451 B1 | 8/2003 | Marmaro et al. | |
| 7,498,131 B2 | 3/2009 | Eijk | |
| 7,794,985 B2 * | 9/2010 | Shoemaker | C12Q 1/6846 435/6.1 |
| 9,909,193 B2 * | 3/2018 | Patel | C12Q 1/6858 |
| 2002/0081598 A1 | 6/2002 | Evans et al. | |

(Continued)

FOREIGN PATENT DOCUMENTS

| | | |
|---|---|---|
| JP | 2005137287 A | 6/2005 |
| JP | 2014140367 | 8/2014 |

(Continued)

OTHER PUBLICATIONS

Jensen Soe et al. (Clin Chem, 2013, 59:2, p. 436-439) (Year: 2013).*

(Continued)

*Primary Examiner* — Stephanie K Mummert

(57) ABSTRACT

Improved methods for amplifying target nucleic acid sequences are provided by 1) first amplifying the number of copies of target nucleic acid sequences in a sample by a first nucleic acid amplification method, and then 2) applying a second nucleic amplification method to the amplified sample, or aliquot thereof, further amplifying the number of copies of target sequences. In embodiments, a first nucleic acid amplification method is a thermocycling method, and a second nucleic acid amplification method is an isothermal method.

5 Claims, 24 Drawing Sheets

Specification includes a Sequence Listing.

(56) References Cited

U.S. PATENT DOCUMENTS

| | | | |
|---|---|---|---|
| 2008/0153763 A1 | 6/2008 | Takagi et al. | |
| 2009/0263789 A1 | 10/2009 | Rabbani et al. | |
| 2010/0075384 A1 | 3/2010 | Kong et al. | |
| 2012/0070831 A1 | 3/2012 | Johnson | |
| 2012/0115140 A1 | 5/2012 | Rivkees et al. | |
| 2013/0224746 A1 | 8/2013 | Barany et al. | |
| 2017/0342476 A1 | 11/2017 | Patel | |
| 2019/0203278 A1 | 7/2019 | Belhocine et al. | |

FOREIGN PATENT DOCUMENTS

| | | |
|---|---|---|
| WO | 2001094634 A2 | 12/2001 |
| WO | 2009002891 A1 | 12/2008 |
| WO | 2012012037 A1 | 1/2012 |
| WO | 2014025337 A1 | 2/2014 |
| WO | 2014145296 A2 | 9/2014 |
| WO | 2015076919 A1 | 5/2015 |
| WO | 2016044664 A1 | 3/2016 |

OTHER PUBLICATIONS

Lehman et al. (Med Micro Immunol, 2008, 197:313-324) (Year: 2008).*

Fukuda et al. Rapid and Sensitive Detection of Norovirus Genomes in Oysters by a Two-Step Isothermal Amplification Assay System Combining Nucleic Acid Sequence-Based Amplification and Reverse Transcription-Loop-Mediated Isothermal Amplification Assays. Applied and Environmental Microbiology, 2008, vol. 74, No. 12, p. 3912-3914

International Search Report and Written Opinion dated Feb. 9, 2016 for PCT/US2015/050822.

Jensen et al., IsoPCR: Analytically Sensitive, Nested, Multiplex Nucleic Acid amplification Method, Clinical Chemistry, Feb. 1, 2013, p. 436.

Jensen et al., RT-isoPCR: nested, high, multiples mRNA amplification. Analyst, vol. 138, No. 20, Jan. 1, 2013, p. 5871.

Salem A N B et al, Multiplex nested RT-PCR for the detection of porcine enteric viruses, Journal of Virological Methods, Elsevier BV, NL, vol. 165, No. 2, May 1, 2010, pp. 283-293.

Office Action dated Nov. 26, 2019 for U.S. Appl. No. 15/458,528.

Office Action dated Feb. 25, 2019 for U.S. Appl. No. 15/458,528.

Anonymous—T4 Polynucleotide Kinase, Thermo Scientific, Jan. 1, 2012.

Callow et al. Selective DNA amplification from complex genomes using universal double-sided adapters, Nucleic Acids Research 2004, 32(2):e21, 2004.

Fu et al. A novel PCT method for amplifying exons (or genes) over intragenic (or intergenic) regions in the genome. Nucleic Acids Research, vol. 20, No. 11, Jun. 11, 1992, pp. 2903-2903.

International Search Report and Written Opinion dated Feb. 9, 2016 for PCT/US2015/050811.

Kimura et al. Optimization of turn-back primers in isothermal amplification. Nucleic Acids Res., 2011, 39(9), e59.

Kuniyoshi, et al. Cloning of Full-length cDNA of Teleost Corticotropin Releasing Hormone Precursor by Improved Inverse PCR. Bioscience Biotechnology Biochemistry, vol. 70, No. 8, Aug. 23, 2006, pp. 1983-1986.

Mitani et al. Mung bean nuclease treatment improves Se genotyping by allele-specific inverse polymerase chain reaction amplification. Legal Medicine, vol. 5, No. 4, Dec. 1, 2003, pp. 233-237.

Office Action dated Dec. 12, 2019 for U.S. Appl. No. 15/881,375.

Office Action dated Feb. 22, 2017 for U.S. Appl. No. 15/087,840.

Office Action dated Sep. 15, 2016 for U.S. Appl. No. 15/087,840.

Wielders et al. mecA Gene IS Widely Disseminated in *Staphylococcus aureus* Population, J Clin Microbiol, 2002, 40 (11): 3970-3975.

* cited by examiner

| | | | |
|---|---|---|---|
| RLX3297 | /5PHOS/GAACCAACGCATGACCCAAG | By Aaron for Pranav | hybrid_orfX_354bp_rc_mecA_1_F |
| RLX3298 | /5PHOS/TTGAACCAACGCATGACCC | By Aaron for Pranav | hybrid_orfX_354bp_rc_mecA_2_F |
| RLX3299 | /5PHOS/CAGACGAAAAGCACCAGAA | By Aaron for Pranav | hybrid_orfX_354bp_rc_mecA_3_F |
| RLX3300 | /5PHOS/GCACCAGAAATATGAGCGAC | By Aaron for Pranav | hybrid_orfX_354bp_rc_mecA_4_F |
| RLX3301 | /5PHOS/ATCCGGTACTGCAGAACTCA | By Aaron for Pranav | hybrid_orfX_354bp_rc_mecA_1_R |
| RLX3302 | /5PHOS/GCAAATCCGGTACTGCAGAA | By Aaron for Pranav | hybrid_orfX_354bp_rc_mecA_2_R |
| RLX3303 | /5PHOS/ATTGGCAAATCCGGTACTGC | By Aaron for Pranav | hybrid_orfX_354bp_rc_mecA_3_R |
| RLX3304 | /5PHOS/GGCAGACAATTGGGTGGTT | By Aaron for Pranav | hybrid_orfX_354bp_rc_mecA_4_R |

| | | | |
|---|---|---|---|
| RLX3367 | GCCAATGACGAATACAAAGTC | Pranav | orfx-mecA post ligation-F |
| RLX3368 | TAATAGCCATCATCATGTTTGG | Pranav | orfx-mecA post ligation-R |

Figure 6

| | | |
|---|---|---|
| RLX3427 | GGAACGAGGACCATCGCATCACCCAAGGTCCTGTTATCCAGATGTATACCAATGTAGAC Pranav | Q80K_F |
| RLX3428 | CGCAGGTGCAGGGTGTCAATGAGCGGGCACCTTGAGGAGCGGGCCAGCCCACGAGGTCT Pranav | Q80K_R |

Figure 8

| Primer | Sequence |
|---|---|
| 1083 A10 | TTTGTCTAAAGGGTCCTGTTATCC |
| 1083 B10 | TAGACAAACAGCCCACGAGG |
| 1083 E08 | TTTGTCTAGTTATCCAGATGTAT |
| 1083 F08 | TAGACAAACCAGCCCACGAGGTC |
| 1087 G01 | TCTTGGTCCAAGGGTCCTGTTATC |
| 1087 H01 | GACCAAGAAGGGTGTCAATGAG |

Figure 10

Histogram plot for Cut-off determination for ZNAT.

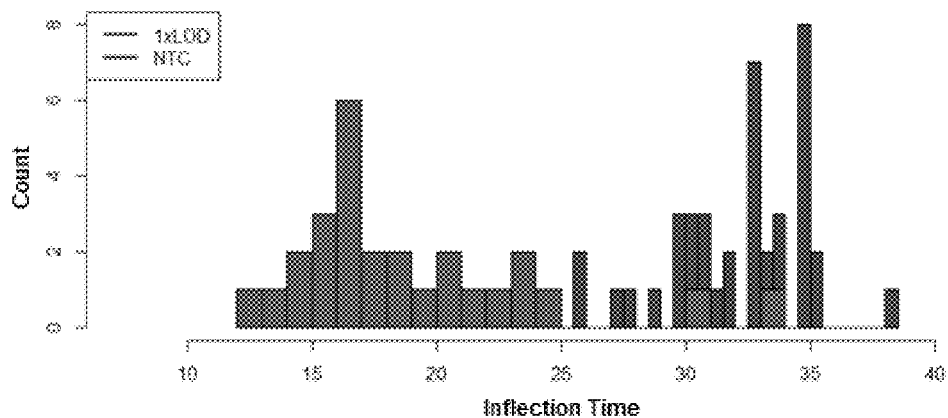

Histogram of ZIKV inflection times <40 min including 40 and 27 venous serum samples, with added ZIKV at 320 copies/mL (10 PFU/mL; 1xLOD) or without ZIKV (No Template Control).

FIG. 11A

ZNAT results interpretation.

| Zika Target | Negative Control | MS2 Control | Zika DNA Control | Final Call |
|---|---|---|---|---|
| Neg | Neg | Pos | Pos | Zika RNA not detected |
| Pos | Neg | Pos | Pos | Zika RNA detected |
| Pos or Neg | Neg | Neg | Pos | Invalid result |
| Pos or Neg | Neg | Pos | Neg | Invalid result |
| Pos or Neg | Pos | Neg | Pos | Invalid result |

FIG. 11B

Quantification of three ZIKV lysates.

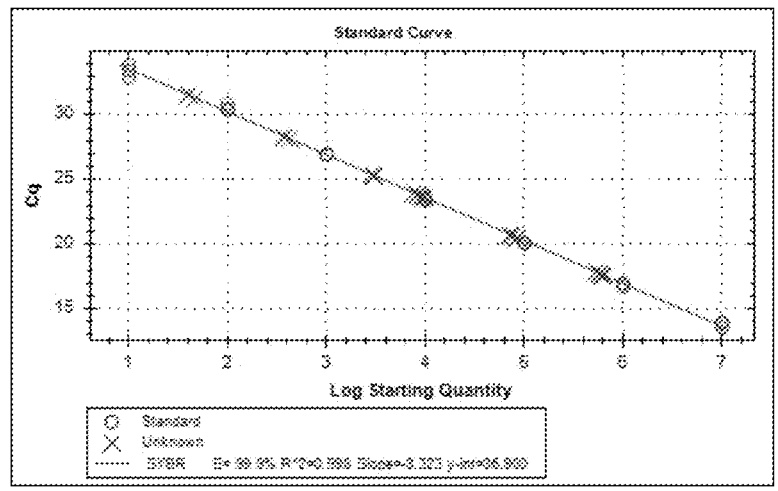

qRT-PCR was used to convert PFU and TCID$_{50}$ to genomic copies for three different ZIKV lysates. Ten-fold serial dilutions of synthetic RNA standards (indicated by green circles) were used to determine a standard curve. Lysates of unknown concentrations tested in parallel are indicated by green crosses.

FIG. 12

Analytical sensitivity determination in ZNAT.

| Blood Matrix | Added ZIKV Concentration (copies/mL) | N (Positive)/ N (Replicates) | % Positive |
|---|---|---|---|
| Venous Serum | 1920 | 6/6 | 100% |
| | 960 | 6/6 | 100% |
| | 480 | 25/26 | 96% |
| | 160 | 4/6 | 66.7% |
| | 32 | 2/6 | 33.3% |
| | 0 | 0/6 | 0% |
| Capillary whole blood | 1920 | 6/6 | 100% |
| | 960 | 6/6 | 100% |
| | 480 | 6/6 | 100% |
| | 320 | 25/26 | 96% |
| | 160 | 24/26 | 92% |
| | 32 | 2/6 | 33.3% |
| | 0 | 0/6 | 0% |

FIG. 13

*In silico* analysis of ZNAT primers against sequenced Zika virus strains.

| | | Pre-amplification Primers | | Isothermal Primers | | |
|---|---|---|---|---|---|---|
| | | # Basepair Mistmatches | | # Basepair Mistmatches | | |
| Genbank ID | Zika Virus Strain/Isolate Description | Forward Primer | Reverse Primer | Forward Primer | Reverse Primer | Tail Region |
| AY632535.2 | MR 766; complete genome | 0 | 0 | 0 | 0 | 0 |
| DQ859059.1 | MR 766 polyprotein gene; complete cds | 0 | 2 | 0 | 1 | 0 |
| EU545988.1 | Polyprotein gene; complete cds | 0 | 0 | 0 | 0 | 0 |
| HQ234498.1 | MR_766 polyprotein gene; partial cds | 0 | 0 | 0 | 0 | 0 |
| HQ234499.1 | P6-740 polyprotein gene; partial cds | 0 | 1 | 0 | 1 | 0 |
| HQ234500.1 | IbH_30656 polyprotein gene; partial cds | 0 | 1 | 0 | 0 | 0 |
| HQ234501.1 | ArD_41519 polyprotein gene; partial cds | 0 | 0 | 0 | 0 | 0 |
| JN860885.1 | FSS13025 polyprotein gene; partial cds | 0 | 0 | 0 | 0 | 0 |
| KF268948.1 | ARB13565 polyprotein gene; complete cds | 1 | 0 | 1 | 0 | 0 |
| KF268949.1 | ARB15076 polyprotein gene; complete cds | 0 | 0 | 0 | 0 | 0 |
| KF268950.1 | ARB7701 polyprotein gene; complete cds | 1 | 0 | 1 | 0 | 0 |
| KF383115.1 | ArB1362 polyprotein gene; complete cds | 0 | 0 | 0 | 0 | 0 |
| KF383116.1 | ArD7117 polyprotein gene; complete cds | 0 | 0 | 0 | 0 | 0 |
| KF383117.1 | ArD128000 polyprotein gene; complete cds | 0 | 0 | 0 | 0 | 0 |
| KF383118.1 | ArD157995 polyprotein gene; complete cds | 3 | 1 | 1 | 2 | 0 |
| KF383119.1 | ArD158084 polyprotein gene; complete cds | 0 | 0 | 0 | 0 | 0 |
| KF383120.1 | ArD142623 nonfunctional polyprotein gene; partial | 0 | 0 | 0 | 0 | 0 |
| KF383121.1 | ArD158095 polyprotein gene; partial cds | 0 | 0 | 0 | 0 | 0 |
| KF993678.1 | PLCal_ZV from Canada polyprotein gene; partial cds | 0 | 0 | 0 | 0 | 0 |
| KJ634273.1 | CK-ISL 2014 E protein (E) gene; partial cds | 0 | 0 | 0 | 0 | 0 |
| KJ776791.1 | H/PF/2013 polyprotein gene; complete cds | 0 | 0 | 0 | 0 | 0 |
| KU312312.1 | Z1106033 polyprotein gene; complete cds | 0 | 0 | 0 | 0 | 0 |
| KU312313.1 | Z1106032 polyprotein gene; partial cds | 0 | 0 | 0 | 0 | 0 |
| KU312314.1 | Z1106031 polyprotein gene; partial cds | 0 | 0 | 0 | 0 | 0 |
| KU312315.1 | Z1106027 polyprotein gene; partial cds | 0 | 0 | 0 | 0 | 0 |
| KU321639.1 | ZikaSPH2015; complete genome | 0 | 1 | 0 | 0 | 0 |
| KU365777.1 | BeH818995 polyprotein gene; complete cds | 0 | 0 | 0 | 0 | 0 |
| KU365778.1 | BeH819015 polyprotein gene; complete cds | 0 | 0 | 0 | 0 | 0 |
| KU365779.1 | BeH819966 polyprotein gene; complete cds | 0 | 0 | 0 | 0 | 0 |
| KU365780.1 | BeH815744 polyprotein gene; complete cds | 0 | 0 | 0 | 0 | 0 |
| KU497555.1 | Brazil-ZKV2015; complete genome | 0 | 0 | 0 | 0 | 0 |
| KU501215.1 | PRVABC59; complete genome | 0 | 0 | 0 | 0 | 0 |
| KU501216.1 | 103344 polyprotein gene; complete cds | 0 | 0 | 0 | 0 | 0 |
| KU501217.1 | 8375 polyprotein gene; complete cds | 0 | 0 | 0 | 0 | 0 |
| KU509998.3 | Haiti/1225/2014; complete genome | 0 | 1 | 0 | 0 | 0 |
| KU527068.1 | Natal RGN; complete genome | 0 | 0 | 0 | 0 | 0 |
| KU646827.1 | Si323 polyprotein gene; partial cds | 0 | 0 | 0 | 0 | 0 |
| KU646828.1 | Si322 polyprotein gene; partial cds | 0 | 0 | 0 | 0 | 0 |
| KU647676.1 | MRS_OPY_Martinique_PaRi_2015 polyprotein gene | 0 | 0 | 0 | 0 | 0 |
| KU681081.3 | H.sapiens-tc/THA/2014/SV0127-14; complete genome | 0 | 0 | 0 | 0 | 0 |
| KU681082.3 | H.sapiens-tc/PHL/2012/CPC-0740; complete genome | 1 | 0 | 0 | 0 | 0 |
| KU707826.1 | SSABR1; complete genome | 0 | 0 | 0 | 0 | 0 |
| KU720415.1 | MR 766 polyprotein gene; complete cds | 0 | 0 | 0 | 0 | 0 |
| KU729217.2 | BeH823339 polyprotein gene; complete cds | 0 | 0 | 0 | 0 | 0 |
| KU729218.1 | BeH828305 polyprotein gene; complete cds | 0 | 0 | 0 | 0 | 0 |
| KU740184.2 | GD01 polyprotein gene; complete cds | 0 | 0 | 0 | 0 | 0 |
| KU744693.1 | VE_Ganxian; complete genome | 0 | 1 | 0 | 0 | 0 |
| KU758868.1 | 27229 polyprotein gene; partial cds | 0 | 0 | 0 | 0 | 0 |
| KU758869.1 | 05211 polyprotein gene; partial cds | 0 | 0 | 0 | 0 | 0 |
| KU758870.1 | 17160 polyprotein gene; partial cds | 0 | 0 | 0 | 0 | 0 |
| KU758871.1 | 17170 polyprotein gene; partial cds | 0 | 0 | 0 | 0 | 0 |
| KU758872.1 | 01170 polyprotein gene; partial cds | 0 | 0 | 0 | 0 | 0 |
| KU758873.1 | 18246 polyprotein gene; partial cds | 0 | 0 | 0 | 0 | 0 |
| KU758874.1 | 20114 polyprotein gene; partial cds | 0 | 0 | 0 | 0 | 0 |
| KU758875.1 | 15042 polyprotein gene; partial cds | 0 | 0 | 0 | 0 | 0 |
| KU758876.1 | 21068 polyprotein gene; partial cds | 0 | 0 | 0 | 0 | 0 |
| KU758877.1 | 17271 polyprotein gene; complete cds | 0 | 0 | 0 | 0 | 0 |
| KU761564.1 | GDZ16001 polyprotein gene; complete cds | 0 | 0 | 0 | 0 | 0 |
| KU820897.3 | FLR polyprotein gene; complete cds | 0 | 0 | 0 | 0 | 0 |

FIG. 14

| | | Pre-amplification Primers | | Isothermal Primers | | |
|---|---|---|---|---|---|---|
| | | # Basepair Mismatches | | # Basepair Mistmatches | | |
| Genbank ID | Zika Virus Strain/Isolate Description | Forward Primer | Reverse Primer | Forward Primer | Reverse Primer | Tail Region |
| KU820898.1 | GZ01 polyprotein gene; complete cds | 0 | 0 | 0 | 0 | 0 |
| KU820899.2 | ZJ03; complete genome | 0 | 0 | 0 | 0 | 0 |
| KU853012.1 | Dominican Republic/2016/PD1; complete genome | 0 | 0 | 0 | 0 | 0 |
| KU853013.1 | Dominican Republic/2016/PD2; complete genome | 0 | 0 | 0 | 0 | 0 |
| KU866423.1 | SZ01/2016 polyprotein gene; complete cds | 0 | 0 | 0 | 0 | 0 |
| KU870645.1 | FB-GWUH-2016; complete genome | 0 | 0 | 0 | 0 | 0 |
| KU922923.1 | MEX/InDRE/Lm/2016; complete genome | 0 | 0 | 0 | 0 | 0 |
| KU922960.1 | MEX/InDRE/Sm/2016; complete genome | 0 | 0 | 0 | 0 | 0 |
| KU926309.1 | Rio-U1; complete genome | 0 | 0 | 0 | 0 | 0 |
| KU926310.1 | Rio-S1; complete genome | 0 | 0 | 0 | 0 | 0 |
| KU937936.1 | ZIKVNL00013 polyprotein gene; complete cds | 0 | 0 | 0 | 0 | 0 |
| KU940224.1 | Bahia09; partial genome | 0 | 0 | 0 | 0 | 0 |
| KU940228.1 | Bahia07; partial genome | 0 | 0 | 0 | 0 | 0 |
| KU955589.1 | Z16006 polyprotein gene; complete cds | 0 | 0 | 0 | 0 | 0 |
| KU955590.1 | Z16019 polyprotein gene; complete cds | 0 | 0 | 0 | 0 | 0 |
| KU955591.1 | A.africanus-tc/SEN/1984/41525-DAK; complete genome | 0 | 0 | 0 | 0 | 0 |
| KU955592.1 | A.taylori-tc/SEN/1984/41662-DAK; complete genome | 0 | 0 | 0 | 0 | 0 |
| KU955593.1 | H.sapiens-tc/KHM/2010/FSS13025; complete genome | 0 | 0 | 0 | 0 | 0 |
| KU955594.1 | M.mulatta-tc/UGA/1947/MR-766; complete genome | 0 | 0 | 0 | 0 | 0 |
| KU955595.1 | A.taylori-tc/SEN/1984/41671-DAK; complete genome | 0 | 0 | 0 | 0 | 0 |
| KU963573.1 | MR-766_SM150-V8/1947 polyprotein (GP1) gene | 0 | 0 | 0 | 0 | 0 |
| KU963574.1 | NGA/IbH-30656_SM21V1-V3/1968 polyprotein (GP1) gene | 0 | 1 | 0 | 0 | 0 |
| KU963796.1 | SZ-WIV01 polyprotein gene; complete cds | 0 | 0 | 0 | 0 | 0 |
| KU985088.1 | MEX/InDRE/Zika-2/2015 envelope protein gene; partial cds | 0 | 0 | 0 | 0 | 0 |
| KU991811.1 | Brazil/2016/INMI1 polyprotein gene; complete cds | 0 | 0 | 0 | 0 | 0 |
| KX051563.1 | Haiti/1/2016; complete genome | 0 | 0 | 0 | 0 | 0 |
| KX056898.1 | GZ02/2016 polyprotein gene; complete cds | 0 | 0 | 0 | 0 | 0 |
| KX087101.2 | PRI/PRVABC59/2015; complete genome | 0 | 0 | 0 | 0 | 0 |
| KX087102.1 | COL/FLR/2015; complete genome | 0 | 0 | 0 | 0 | 0 |
| KX101060.1 | Bahia02; partial genome | 0 | 1 | 0 | 0 | 0 |
| KX117076.1 | Zhejiang04; complete genome | 0 | 0 | 0 | 0 | 0 |
| KX156774.1 | PAN/CDC-259359_V1-V3/2015; complete genome | 0 | 0 | 0 | 0 | 0 |
| KX156775.1 | PAN/CDC-259249_V1-V3/2015; complete genome | 0 | 0 | 0 | 0 | 0 |
| KX156776.1 | PAN/CDC-259364_V1-V2/2015; complete genome | 0 | 0 | 0 | 0 | 0 |
| KX173840.1 | 16Z10 envelope protein gene; partial cds | 0 | 0 | 0 | 0 | 0 |
| KX173841.1 | 16Z11 envelope protein gene; partial cds | 0 | 0 | 0 | 0 | 0 |
| KX173843.1 | 16Z62 envelope protein gene; partial cds | 0 | 0 | 0 | 0 | 0 |
| KX173844.1 | 16Z62 envelope protein gene; partial cds | 0 | 0 | 0 | 0 | 0 |
| KX185891.1 | CN/SZ02/2016 polyprotein gene; complete cds | 0 | 0 | 0 | 0 | 0 |
| KX197192.1 | Brazil/PE243/2015; complete genome | 0 | 1 | 0 | 0 | 0 |
| KX198134.1 | DAK-AR-41524_A1C1-V2/1984; complete genome | 0 | 0 | 0 | 0 | 0 |
| KX198135.1 | PAN/BEI-259634_V4/2016; complete genome | 0 | 0 | 0 | 0 | 0 |
| KX247632.1 | MEX_I_7 polyprotein gene; complete cds | 0 | 0 | 0 | 0 | 0 |
| KX247646.1 | COL/UF-1/2016; complete genome | 0 | 0 | 0 | 0 | 0 |
| KX253996.1 | ZKC2/2016; complete genome | 0 | 0 | 0 | 0 | 0 |
| KX262887.1 | 103451; complete genome | 0 | 0 | 0 | 0 | 0 |
| KX280026.1 | Paraiba_01; complete genome | 0 | 0 | 0 | 0 | 0 |
| LC002520.1 | MR766-NIID | 0 | 0 | 0 | 0 | 0 |

FIG. 14 (continued)

Inclusivity of ZNAT and CDC ZIKV RT-PCR

| Zika Virus Strain | Concentration (copies/mL) | MicroLab ZNAA | CDC RT-PCR | In-house RT-PCR* |
|---|---|---|---|---|
| DakArD 41662 | 960 | 3/3 | 0/3 | 3/3 |
| MR 766 | 960 | 3/3 | 0/3 | 3/3 |

*Amplified same RNA extract as used for the CDC RT-PCR to determine whether proper RNA extraction occurred.

FIG. 15

*In silico* mismatch analysis of ZNAT primers against potentially cross-reacting organisms.

| Organism | Strain/Chromosome | GenBank ID | Pre-amp primers | | | Isothermal primers | | | # Mismatches on Tail/Probe |
|---|---|---|---|---|---|---|---|---|---|
| | | | Predicted Product Length (bp) | # Mismatches on Forward Priming Site | # Mismatches on Reverse Priming Site | Predicted Product Length (bp) | # Mismatches on Forward Priming Site | # Mismatches on Reverse Priming Site | |
| Trypanosoma cruzi | CL Brener | KM_800123.1 | NA | NA | NA | 325 | 1 | 2 | 2 |
| Trypanosoma cruzi | CL Brener | XM_812740.1 | NA | NA | NA | 656 | 3 | 2 | 3 |
| Enterovirus B Echovirus | Echovirus E21 isolate 24-YN-2006AFP | JQ963969.1 | NA | NA | NA | 216 | 2 | 2 | 2 |
| Schistosoma mansoni | Puerto Rico chromosome W | HE601631.1 | NA | NA | NA | 52 | 3 | 2 | 2 |
| Schistosoma mansoni | Puerto Rico chromosome W | HE601631.1 | NA | NA | NA | 27 | 4 | 4 | 3 |
| Schistosoma mansoni | Puerto Rico chromosome 1 | HE601624.1 | NA | NA | NA | 682 | 3 | 3 | 3 |
| Schistosoma mansoni | Puerto Rico chromosome 5 | HE601628.1 | NA | NA | NA | 131 | 3 | 1 | 3 |
| Schistosoma mansoni | Puerto Rico chromosome W | HE601631.1 | 521 | 4 | 4 | NA | NA | NA | NA |
| Schistosoma mansoni | Puerto Rico chromosome W | HE601631.1 | 972 | 6 | 4 | NA | NA | NA | NA |
| Schistosoma mansoni | Puerto Rico chromosome 1 | HE601624.1 | 513 | 4 | 5 | NA | NA | NA | NA |
| Schistosoma haematobium | - | KM_012945467.1 | 321 | 6 | 6 | NA | NA | NA | NA |
| Koutango virus | DakArD 5443 | EU082200.1 | 101 | 5 | 3 | NA | NA | NA | NA |
| West Nile virus | KOU DakArD 5443 | AF196537.1 | 102 | 3 | 3 | NA | NA | NA | NA |
| Leptospira biflexa | serovar Patoc 1 (Paris) chromosome I | CP000786.1 | 312 | 5 | 3 | NA | NA | NA | NA |
| Leptospira biflexa | serovar Patoc 1 (Paris) chromosome I | CP000786.1 | 329 | 5 | 4 | NA | NA | NA | NA |
| Leptospira biflexa | serovar Patoc 1 (Paris) chromosome I | CP000786.1 | 388 | 6 | 6 | NA | NA | NA | NA |
| Leptospira biflexa | serovar Patoc 1 (Ames) chromosome I | CP000777.1 | 312 | 5 | 3 | NA | NA | NA | NA |
| Leptospira biflexa | serovar Patoc 1 (Ames) chromosome I | CP000777.1 | 329 | 5 | 4 | NA | NA | NA | NA |
| Leptospira biflexa | serovar Patoc 1 (Ames) chromosome I | CP000777.1 | 388 | 6 | 6 | NA | NA | NA | NA |
| Plasmodium vivax | 18S ribosomal RNA gene | AF316893.1 | 695 | 4 | 4 | NA | NA | NA | NA |
| Plasmodium vivax | 18S ribosomal RNA gene | AF316893.1 | 695 | 6 | 4 | NA | NA | NA | NA |

FIG. 17

*In-silico* analysis of Zika preliminary amplification and isothermal primers against nucleic acid sequences from prevalent diseases with Zika-like onset symptoms

| Organism | Taxid | Preamp Primers | Isothermal Primers | Conclusion |
|---|---|---|---|---|
| Dengue virus group | 11052 | No Cross-reactivity | No Cross-reactivity | No Cross-reactivity |
| Dengue virus 1 | 11053 | No Cross-reactivity | No Cross-reactivity | No Cross-reactivity |
| Dengue virus 2 | 11060 | No Cross-reactivity | No Cross-reactivity | No Cross-reactivity |
| Dengue virus 3 | 11069 | No Cross-reactivity | No Cross-reactivity | No Cross-reactivity |
| Dengue virus 4 | 11070 | No Cross-reactivity | No Cross-reactivity | No Cross-reactivity |
| Yellow fever virus group | 40005 | No Cross-reactivity | No Cross-reactivity | No Cross-reactivity |
| Yellow fever virus 17D | 11090 | No Cross-reactivity | No Cross-reactivity | No Cross-reactivity |
| West Nile virus | 11082 | Predicted products on: AF196835.1 | No Cross-reactivity | No Cross-reactivity |
| Chikungunya virus | 37124 | No Cross-reactivity | No Cross-reactivity | No Cross-reactivity |
| Mayaro virus | 59301 | No Cross-reactivity | No Cross-reactivity | No Cross-reactivity |
| Human parvovirus B19 | 10798 | No Cross-reactivity | No Cross-reactivity | No Cross-reactivity |
| Plasmodium falciparum | 5833 | No Cross-reactivity | No Cross-reactivity | No Cross-reactivity |
| St. Louis encephalitis virus | 11080 | No Cross-reactivity | No Cross-reactivity | No Cross-reactivity |
| Koutango virus | 11071 | Predicted products on: EU082200.1 | No Cross-reactivity | No Cross-reactivity |
| Spondweni virus | 64318 | No Cross-reactivity | No Cross-reactivity | No Cross-reactivity |
| Hepatitis C virus | 11103 | No Cross-reactivity | No Cross-reactivity | No Cross-reactivity |
| Eastern equine encephalitis virus | 11021 | No Cross-reactivity | No Cross-reactivity | No Cross-reactivity |
| Western equine encephalitis virus | 11039 | No Cross-reactivity | No Cross-reactivity | No Cross-reactivity |
| Ross River virus | 11029 | No Cross-reactivity | No Cross-reactivity | No Cross-reactivity |
| Barmah Forest virus | 11020 | No Cross-reactivity | No Cross-reactivity | No Cross-reactivity |
| O'nyong-nyong virus | 11027 | No Cross-reactivity | No Cross-reactivity | No Cross-reactivity |
| Sindbis virus | 11034 | No Cross-reactivity | No Cross-reactivity | No Cross-reactivity |
| Tonate virus | 60877 | No Cross-reactivity | No Cross-reactivity | No Cross-reactivity |
| Una virus | 59304 | No Cross-reactivity | No Cross-reactivity | No Cross-reactivity |
| Measles virus | 11234 | No Cross-reactivity | No Cross-reactivity | No Cross-reactivity |
| Rubella virus | 11041 | No Cross-reactivity | No Cross-reactivity | No Cross-reactivity |
| Enterovirus | 12059 | No Cross-reactivity | No Cross-reactivity | No Cross-reactivity |
| Enterovirus A | 138948 | No Cross-reactivity | No Cross-reactivity | No Cross-reactivity |
| Enterovirus B | 138949 | No Cross-reactivity | Predicted products on: JQ868989.1 | No Cross-reactivity* |
| Enterovirus C | 138950 | No Cross-reactivity | No Cross-reactivity | No Cross-reactivity |
| Enterovirus 271 | 39054 | No Cross-reactivity | No Cross-reactivity | No Cross-reactivity |
| Coxsackievirus A6 | 86107 | No Cross-reactivity | No Cross-reactivity | No Cross-reactivity |
| Echovirus E30 | 41846 | No Cross-reactivity | No Cross-reactivity | No Cross-reactivity |
| Coxsackievirus A16 | 31704 | No Cross-reactivity | No Cross-reactivity | No Cross-reactivity |
| Human mastadenovirus B | 108098 | No Cross-reactivity | No Cross-reactivity | No Cross-reactivity |
| Human mastadenovirus D | 130310 | No Cross-reactivity | No Cross-reactivity | No Cross-reactivity |
| Human mastadenovirus C | 129951 | No Cross-reactivity | No Cross-reactivity | No Cross-reactivity |
| Human adenovirus B1 | 565302 | No Cross-reactivity | No Cross-reactivity | No Cross-reactivity |
| Human adenovirus 7 | 10519 | No Cross-reactivity | No Cross-reactivity | No Cross-reactivity |
| Human mastadenovirus F | 130309 | No Cross-reactivity | No Cross-reactivity | No Cross-reactivity |
| Human adenovirus 83 | 45659 | No Cross-reactivity | No Cross-reactivity | No Cross-reactivity |
| Human adenovirus 21 | 32603 | No Cross-reactivity | No Cross-reactivity | No Cross-reactivity |
| Hepatitis B virus | 10407 | No Cross-reactivity | No Cross-reactivity | No Cross-reactivity |
| Human immunodeficiency virus 1 | 11676 | No Cross-reactivity | No Cross-reactivity | No Cross-reactivity |
| Human immunodeficiency virus 2 | 11709 | No Cross-reactivity | No Cross-reactivity | No Cross-reactivity |
| Varicella Zoster Virus (Human herpesvirus 3) | 10335 | No Cross-reactivity | No Cross-reactivity | No Cross-reactivity |
| Cytomegalovirus | 10358 | No Cross-reactivity | No Cross-reactivity | No Cross-reactivity |
| Epstein-Barr virus (Human herpesvirus 4) | 10376 | No Cross-reactivity | No Cross-reactivity | No Cross-reactivity |
| Rickettsia felis | 42862 | No Cross-reactivity | No Cross-reactivity | No Cross-reactivity |
| Borrelia burgdorferi | 139 | No Cross-reactivity | No Cross-reactivity | No Cross-reactivity |
| Hepatovirus A | 12092 | No Cross-reactivity | No Cross-reactivity | No Cross-reactivity |
| Schistosoma mansoni | 6183 | Predicted products on: HE601631.1, HE601624.1 | Predicted products on: HE601631.1, HE601621.1, HE601628.1, HE601624.1 | No Cross-reactivity* |
| Plasmodium sp. | 31272 | No Cross-reactivity | No Cross-reactivity | No Cross-reactivity |
| Rickettsia sp. | 783 | No Cross-reactivity | No Cross-reactivity | No Cross-reactivity |
| Plasmodium vivax | 5855 | Predicted products on: AF316892.1, AF316895.1 | No Cross-reactivity | No Cross-reactivity |
| Schistosoma mekongi | 38744 | No Cross-reactivity | No Cross-reactivity | No Cross-reactivity |
| Schistosoma haematobium | 6185 | Predicted products on: XM_012945467.1 | No Cross-reactivity | No Cross-reactivity |
| Schistosoma guineensis | 293876 | No Cross-reactivity | No Cross-reactivity | No Cross-reactivity |
| Schistosoma intercalatum | 6187 | No Cross-reactivity | No Cross-reactivity | No Cross-reactivity |
| Schistosoma japonicum | 6182 | No Cross-reactivity | No Cross-reactivity | No Cross-reactivity |
| Trypanosoma cruzi | 5693 | No Cross-reactivity | Predicted products on: XM_800223.1, XM_812740.1 | No Cross-reactivity* |
| Salmonella enterica subsp. enterica serovar Typhi | 90370 | No Cross-reactivity | No Cross-reactivity | No Cross-reactivity |
| Leptospira biflexa | 172 | Predicted products on: CP000786.1, CP000777.1 | No Cross-reactivity | No Cross-reactivity |
| Streptococcus sp. 'group A' | 36470 | ND | ND | ND |

*Further in-silico analyses done; ND = Not determined

FIG. 16

Analytical specificity of Theranos ZNAT in serum

| | | Cross-Reactivity | | Interference | |
|---|---|---|---|---|---|
| | | 0 copies/mL ZIKV | | 960 copies/mL ZIKV | |
| Virus/Bacteria/Parasite | Concentration | N Positive/ N Replicates | % Positive | N Positive/ N Replicates | % Positive |
| P. falciparum | 1 x 10$^6$ copies/mL | 0/3 | 0% | 3/3 | 100% |
| Dengue Virus 1 | 1 x 10$^6$ copies/mL | 0/3 | 0% | 3/3 | 100% |
| Dengue Virus 2 | 1 x 10$^6$ copies/mL | 0/3 | 0% | 3/3 | 100% |
| Dengue Virus 3 | 1 x 10$^6$ copies/mL | 0/3 | 0% | 3/3 | 100% |
| Dengue Virus 4 | 1 x 10$^6$ copies/mL | 0/3 | 0% | 3/3 | 100% |
| West Nile 1 | 1 x 10$^5$ copies/mL | 0/3 | 0% | 3/3 | 100% |
| West Nile 2 | 1 x 10$^5$ copies/mL | 0/3 | 0% | 3/3 | 100% |
| Chikungunya | 5 x 10$^3$ copies/mL | 0/3 | 0% | 3/3 | 100% |
| Yellow Fever | 1 x 10$^4$ copies/mL | 0/3 | 0% | 3/3 | 100% |
| Parvovirus | 1 x 10$^6$ copies/mL | 0/3 | 0% | 3/3 | 100% |
| Mayaro Virus | 1 x 10$^6$ copies/mL | 0/3 | 0% | 3/3 | 100% |
| Bilirubin | 342 μM | 0/3 | 0% | 3/3 | 100% |
| Cholesterol | 13 mM | 0/3 | 0% | 3/3 | 100% |
| EDTA, pH 8-0 | 6-2 mM | 0/3 | 0% | 3/3 | 100% |
| Gamma Globulin | 5 mg/mL | 0/3 | 0% | 3/3 | 100% |
| Hemoglobin | 5 mg/mL | 0/3 | 0% | 3/3 | 100% |
| Heparin Lithium Salt | 19 U/mL | 0/3 | 0% | 3/3 | 100% |
| Human Genomic DNA | 4 μg/mL | 0/3 | 0% | 3/3 | 100% |
| Triglyceride Mixture (C2-C10) | 37 mM | 0/3 | 0% | 3/3 | 100% |
| Sodium Citrate | 0-25% | 0/3 | 0% | 3/3 | 100% |

FIG. 18

Interfering substances analysis of ZNAT in serum

| | | 0 PFU/mL Zika Virus | | | 30 PFU/mL Zika Virus | | |
|---|---|---|---|---|---|---|---|
| Interferent | Concentration | Replicates (n) | Positive Inflections | Positive Calls | Replicates (n) | Positive Inflections | Positive Calls |
| Bilirubin | 342 μM | 3 | 0 | 0% | 3 | 3 | 100% |
| Cholesterol | 13 mM | 3 | 0 | 0% | 3 | 3 | 100% |
| EDTA, pH 8-0 | 6-2 mM | 3 | 0 | 0% | 3 | 3 | 100% |
| Gamma Globulin | 5 mg/mL | 3 | 0 | 0% | 3 | 3 | 100% |
| Hemoglobin | 5 mg/mL | 3 | 0 | 0% | 3 | 3 | 100% |
| Heparin Lithium Salt | 19 U/mL | 3 | 0 | 0% | 3 | 3 | 100% |
| Human Genomic DNA | 4 μg/mL | 3 | 0 | 0% | 2 | 2 | 100% |
| Triglyceride Mixture (C2-C10) | 37 mM | 3 | 0 | 0% | 3 | 3 | 100% |
| Sodium Citrate | 0-25% | 3 | 0 | 0% | 3 | 3 | 100% |
| P. falciparum | 1 x 10$^6$ copies/mL | 3 | 0 | 0% | 3 | 3 | 100% |
| Dengue Virus 1 | 1 x 10$^6$ copies/mL | 3 | 0 | 0% | 3 | 3 | 100% |
| Dengue Virus 2 | 1 x 10$^6$ copies/mL | 3 | 0 | 0% | 3 | 3 | 100% |
| Dengue Virus 3 | 1 x 10$^6$ copies/mL | 3 | 0 | 0% | 3 | 3 | 100% |
| Dengue Virus 4 | 1 x 10$^6$ copies/mL | 3 | 0 | 0% | 3 | 3 | 100% |
| West Nile 1 | 1 x 10$^5$ copies/mL | 3 | 0 | 0% | 3 | 3 | 100% |
| West Nile 2 | 1 x 10$^5$ copies/mL | 3 | 0 | 0% | 3 | 3 | 100% |
| Chikungunya | 5 x 10$^3$ copies/mL | 3 | 0 | 0% | 3 | 3 | 100% |
| Yellow Fever | 1 x 10$^4$ copies/mL | 3 | 0 | 0% | 3 | 3 | 100% |
| Parvovirus | 1 x 10$^6$ copies/mL | 3 | 0 | 0% | 3 | 3 | 100% |
| Mayaro Virus | 1 x 10$^6$ copies/mL | 3 | 0 | 0% | 3 | 3 | 100% |

FIG. 19

Run-to-run contamination analysis of ZNAT in serum

| Round | Sample | Concentration (copies/mL) | N Positive/ N Replicates | % Positive |
|---|---|---|---|---|
| 1 | Zika culture | $1.3 \times 10^7$ | 5/5 | 100% |
|   | NTC | 0 | 0/5 | 0% |
| 2 | Zika culture | $1.3 \times 10^7$ | 5/5 | 100% |
|   | NTC | 0 | 0/5 | 0% |
| 3 | Zika culture | $1.3 \times 10^7$ | 5/5 | 100% |
|   | NTC | 0 | 0/5 | 0% |
| 4 | Zika culture | $1.3 \times 10^7$ | 5/5 | 100% |
|   | NTC | 0 | 0/5 | 0% |
| 5 | Zika culture | $1.3 \times 10^7$ | 5/5 | 100% |
|   | NTC | 0 | 0/5 | 0% |

NTC: Non-templated control.

FIG. 20

Clinical studies using ZNAT

| | | | ZIKV Positive Detections (N Positive/N Replicates) | | |
|---|---|---|---|---|---|
| | | | Minilab ZNAA | CDC RT-PCR Serum | altona RealStar® | |
| | Country of Origin | Donor Symptoms | | | Serum | Urine |
| Venous Serum | Dominican Republic & Colombia† | Zika-symptomatic | 39/69 | 17/69 | 17/22 | |
| | | Zika-symptomatic with added ZIKV | 33/33 | 33/33 | | |
| | U.S. | Healthy/Febrile‡ | 0/78 | 0/78 | | |
| Capillary Whole Blood | Dominican Republic | Zika-symptomatic | 26/30 | 5/30 | 11/21 | 10/10 |
| | U.S. | Healthy with added ZIKV* | 24/25 | 23/25 | 2/2 | |
| | | Healthy | 0/52 | 0/52 | | |

†Among the 69 Zika-symptomatic donors, 34 were from Colombia while the remaining 35 were from Dominican Republic. All Zika-symptomatic with added ZIKV specimens were prepared at 480, 960, and 2,400 copies/mL from Dominican Republic donors. ‡Among 78 donors, 25 were febrile while the remaining 53 were healthy. *At 480, 960, and 2,400 copies/mL.

CDC RT-PCR with altona confirmation

| | | Positive | Negative |
|---|---|---|---|
| Minilab ZNAA | Positive | 67 | 5 |
| | Negative | 0 | 108 |
| | Total | 67 | 113 |

PPA: 100·0% (95% CI 94·6-100)
NPA: 95·6% (95% CI 90·1-98·1)

CDC RT-PCR with altona confirmation

| | | Positive | Negative |
|---|---|---|---|
| Minilab ZNAA | Positive | 50 | 0 |
| | Negative | 1 | 56 |
| | Total | 51 | 56 |

PPA: 98·0% (95% CI 89·7-99·7)
NPA: 100·0% (95% CI 93·6-100·0)

FIG. 21

Nucleic Acid Amplification (NAA) Detector and Thermocycler

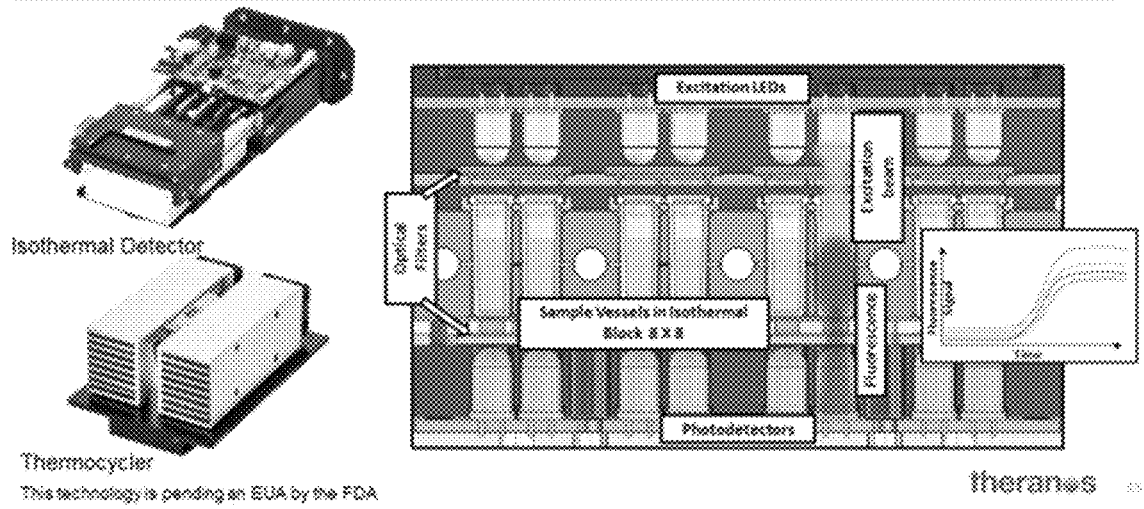

FIG. 22

NAA Zika Assay – Methodology

- Magnetic beads extract nucleic acids via liquid handling
- Thermocycle based pre-amplification step performed via multiplex rRT-PCR
- Isothermal amplification and detection method
- High sensitivity achieved through integrated on-board sample extraction, amplification, and detection
- Sample-to-result

FIG. 23A

NAA Zika Assay in Venous Serum on TSPU - Performance Characteristics

- Sensitivity (LoD)
- Specificity
- Inclusivity
- Clinical performance (concordance)

This technology is pending an EUA by the FDA theranos

FIG. 23B

NAA Zika Assay - Analytical Sensitivity Limit of Detection (LoD)

| Concentration (copies/mL) | Detection (# detected / # tested) | % Detection |
|---|---|---|
| 1920 | 6/6 | 100 % |
| 960 | 6/6 | 100 % |
| 480 (LoD) | 25/26 | 96 % |
| 160 | 4/6 | 67 % |
| 32 | 2/6 | 33 % |
| 0 | 0/6 | 0 % |

LoD for CDC Zika test = 930 copies/mL.
Emerg Infect Dis 2008; 14:1232-1239

This technology is pending an EUA by the FDA theranos

FIG. 24

NAA Zika Assay – Analytical Specificity

| | Concentration | | | | |
|---|---|---|---|---|---|
| P. falciparum | 1 x 10⁵ | 0/3 | 0% | 3/3 | 100% |
| Dengue Virus Types 1-4 | 1 x 10⁵ | 0/3 | 0% | 3/3 | 100% |
| West Nile Types 1 & 2 | 1 x 10⁵ | 0/3 | 0% | 3/3 | 100% |
| Chikungunya | 5 x 10⁵ | 0/3 | 0% | 3/3 | 100% |
| Yellow Fever | 1 x 10⁴ | 0/3 | 0% | 3/3 | 100% |
| Parvovirus | 1 x 10⁵ | 0/3 | 0% | 3/3 | 100% |
| Mayaro Virus | 1 x 10⁵ | 0/3 | 0% | 3/3 | 100% |

This technology is pending an EUA by the FDA theranos

FIG. 25

NAA Zika Assay – Analytical Specificity

| | Concentration | | | | |
|---|---|---|---|---|---|
| Bilirubin | 342 µM | 0/3 | 0% | 3/3 | 100% |
| Cholesterol | 13 mM | 0/3 | 0% | 3/3 | 100% |
| EDTA, pH 8.0 | 6.2 mM | 0/3 | 0% | 3/3 | 100% |
| Gamma Globulin | 5 mg/mL | 0/3 | 0% | 3/3 | 100% |
| Hemoglobin | 5 mg/mL | 0/3 | 0% | 3/3 | 100% |
| Heparin Lithium Salt | 19 U/mL | 0/3 | 0% | 3/3 | 100% |
| Human Genomic DNA | 4 µg/mL | 0/3 | 0% | 3/3 | 100% |
| Triglyceride Mixture (C2-C10) | 37 mM | 0/3 | 0% | 3/3 | 100% |
| Sodium Citrate | 0.25% | 0/3 | 0% | 3/3 | 100% |

This technology is pending an EUA by the FDA theranos

FIG. 26

Inclusivity of NAA Zika Assay

| Zika Virus Strain | Concentration (copies/mL) | # Replicates Detected / Total |
|---|---|---|
| DakArD 41662 | 980 | 3/3 |
| MR 766 | 980 | 3/3 |

*Amplified same RNA extract as used for CDC RT-PCR to determine whether proper RNA extraction occurred.
This technology is pending an EUA by the FDA theranos

FIG. 27A

Molecular Biology: NAA Zika Assay Shows No Carry-over

| Round | Zika Concentration (copies/mL) | # Replicates Positive | % Positive |
|---|---|---|---|
| 1 | $1.3 \times 10^7$ | 5/5 | 100% |
|   | 0 | 0/5 | 0% |
| 2 | $1.3 \times 10^7$ | 5/5 | 100% |
|   | 0 | 0/5 | 0% |
| 3 | $1.3 \times 10^7$ | 5/5 | 100% |
|   | 0 | 0/5 | 0% |
| 4 | $1.3 \times 10^7$ | 5/5 | 100% |
|   | 0 | 0/5 | 0% |
| 5 | $1.3 \times 10^7$ | 5/5 | 100% |
|   | 0 | 0/5 | 0% |

FIG. 27B

NAA Zika Assay – Clinical Study Overview

| | |
|---|---|
| Population | Healthy, febrile, or Zika symptomatic |
| Sample type and matrix | Venous serum |
| Analyzers & Assays | 24 TPSUs<br>CDC RT-PCR assay<br>altona RealStar® (EUA Cleared Method) |
| Study design | FDA EUA guidance |
| Analysis | Compute negative and positive percent agreement compared to the reference methods |

This technology is investigational and has not been cleared or approved by the FDA.

theranos

FIG. 28

Percent Agreement of NAA Zika Assay Compared to CDC RT-PCR with Confirmation by altona RealStar®

| | NAA/<br>CDC & altona | Percent<br>Agreement | 95% confidence interval |
|---|---|---|---|
| Negative percent agreement | 109 / 109 | 100% | [94.6, 100.0]% |
| Positive percent agreement | 67 / 72 | 95.6% | [90.1, 98.9]% |

Venous Serum (N=181)
    78 from US (healthy and febrile samples)
    103 from Dominican Republic and Colombia (Zika symptomatic)

This technology is pending an EUA by the FDA.

theranos

FIG. 29

NAA Zika Assay: Clinical Study Overview

| | |
|---|---|
| Population | Healthy or Zika symptomatic |
| Sample type and matrix | Capillary whole blood, venous serum, and urine |
| Analyzers & Assays | 20 TPSUs<br>CDC RT-PCR assay<br>altona RealStar® (EUA Cleared Method) |
| Study design | FDA EUA guidance |
| Analysis | Compute negative and positive percent agreement compared to the comparative methods |

FIG. 30

Molecular Biology: NAA Zika Assay with Capillary Whole Blood is Consistent with Comparators

| | NAA<br>CDC & altona | Percent<br>Agreement | 95% Confidence<br>Interval |
|---|---|---|---|
| Negative percent agreement | 56 / 56 | 100% | [93.6, 100.0]% |
| Positive percent agreement | 50 / 51 | 98% | [89.7, 99.7]% |

Capillary whole blood, venous serum, and urine (n = 107)
    77 from US (apparently healthy)
    30 from the Dominican Republic (Zika symptomatic)

LoD capillary = 320 copies/mL

FIG. 31

SEQUENCE LISTING

<160> NUMBER OF SEQ ID NOS: 39

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgccaactta tcatacaggc                                                  20

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gactgcgcca ctttcc                                                      16

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgccaactta tcatacaggc ctt                                              23

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgcccttcca aatacttgac tgcgcca                                          27

<210> SEQ ID NO 5
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
ggaacgagga ccatcgcatc acccaagggt cctgttatcc agatgtatac caatgtagac      60
caagacctcg tgggctggcc cgctcctcaa ggtgcccgct cattgacacc ctgcacctgc     120
g                                                                    121

<210> SEQ ID NO 6
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
ggaacgagga ccatcgcatc acccaagggt cctgttatcc agatgtatac caatgtagac        60
aaagacctcg tgggctggcc cgctcctcaa ggtgcccgct cattgacacc ctgcacctgc       120
g                                                                      121

<210> SEQ ID NO 7
<211> LENGTH: 101
<212> TYPE: DNA
<213> ORGANISM: Zika virus

<400> SEQUENCE: 7
aagcctacct tgacaagcaa tcagacactc aatatgtctg caaagaacg ttagtggaca         60 gaggctgggg aaatggatgt ggacttttg gcaaagggag c                            101

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aagcctacct tgacaagc                                                     18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctccctttg ccaaaaag                                                     18

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
accagcatcc gtagccttat t                                                 21

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggaccgcgtg tctgatcc                                                     18

<210> SEQ ID NO 12
<211> LENGTH: 25
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 12
tttccccatc agacactcaa tatgt                                              25

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggggaaagc caaaaagtcc aca                                                23

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtgccccagt tctccaacgg                                                    20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggggcactt gtaaggcgct gc                                                 22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctgtggcatg aacccaatag                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
ccacgctcca gctgcaaagg                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 18
atcccataga gcaccactcc                                               20

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gacatggctt cggacag                                                  17

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atattgagtg tctgattgct tg                                            22

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
tgcccaacac aaggtgaagc c                                             21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaaccaacgc atgacccaag                                               20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ttgaaccaac gcatgaccc                                                19

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagacgaaaa agcaccagaa                                            20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcaccagaaa atatgagcga c                                          21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atccggtact gcagaactca                                            20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcaaatccgg tactgcagaa                                            20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
attggcaaat ccggtactgc                                            20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggcagacaaa ttgggtggtt                                            20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 30
gccaatgacg aatacaaagt c                                              21

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
taatagccat catcatgttt gg                                             22

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggaacgagga ccatcgcatc acccaagggt cctgttatcc agatgtatac caatgtagac    60

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgcaggtgca gggtgtcaat gagcgggcac cttgaggagc gggccagccc acgaggtct     59

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tttgtctaaa gggtcctgtt atcc                                           24

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tagacaaaca gcccacgagg                                                20

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
```

```
tttgtctagt tatccagatg tat                                              23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tagacaaacc agcccacgag gtc                                              23

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcttggtcca agggtcctgt tatc                                             24

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gaccaagaag ggtgtcaatg agc                                              23
```

HYBRID MULTI-STEP NUCLEIC ACID AMPLIFICATION

CROSS-REFERENCE

This application claims priority to U.S. Applications Nos. 62/368,961 filed Jul. 29, 2016, 62/368,995 filed Jul. 29, 2016, 62/369,006 filed Jul. 29, 2016, 62/369,179 filed Jul. 31, 2016, and 62/368,904 filed Jul. 29, 2016. All of the foregoing applications and patents are incorporated herein by reference in their entirety for all purposes.

SEQUENCE LISTING

The instant application contains a Sequence Listing which has been submitted electronically in ASCII format and is hereby incorporated by reference in its entirety. Said ASCII copy, created on Nov. 16, 2017, is named 3043_201_SL.txt and is 9,540 bytes in size.

BACKGROUND

While multiple techniques for the amplification of nucleic acids are known, current techniques suffer from various limitations such as in relation to the speed, sensitivity, and/or specificity of target nucleic acid amplification. Accordingly, improved nucleic acid amplification techniques are needed.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Applicant discloses improved methods for amplifying one or more target nucleic acid sequences in a sample. Target nucleic acids may be DNA sequences, or may be RNA sequences. Improved nucleic acid amplification methods disclosed herein comprise utilizing two different nucleic acid amplification methods sequentially. In embodiments, a first nucleic amplification method is applied to a sample, amplifying the number of copies of one or more target nucleic acid sequences in the sample; followed by application of a second nucleic amplification method to the sample, or aliquot thereof, further amplifying the number of copies of one or more target nucleic acid sequences in the sample. In embodiments, any two nucleic amplification methods may be performed sequentially, wherein a first nucleic amplification method is applied to a sample, and then a second nucleic amplification method is applied to that sample, or an aliquot thereof, after amplification by the first nucleic amplification method. In embodiments, an improved nucleic acid amplification method comprises first utilizing a thermocycling amplification method, and then utilizing a non-thermocycling (e.g., an isothermal) amplification method, to amplify a target nucleic acid sequence, or to amplify a plurality of target nucleic acid sequences, in a sample. In embodiments, a first nucleic amplification method comprises a polymerase chain reaction (PCR) amplification method. Suitable PCR methods include two-step PCR, and include 3-step PCR methods. In embodiments where the target nucleic acid is RNA, reverse transcriptase PCR (rtPCR) may be used. In embodiments, a second nucleic amplification method comprises an isothermal nucleic acid amplification method as described in International Application No. PCT/US14/30028, filed Mar. 15, 2014; in International Application No. PCT/US14/30034, filed Mar. 15, 2014; in International Application No. PCT/US14/56151, filed Sep. 17, 2014; in International Application No. PCT/US14/30036, filed Mar. 15, 2014; or in International Application No. PCT/US15/50811, filed Sep. 17, 2015, each of which applications are hereby incorporated by reference herein in their entirety for all purposes.

Accordingly, a method for amplifying a target nucleic acid sequence in a sample comprises: amplifying the number of copies of one or more target nucleic acid sequences in the sample by a first nucleic acid amplification method; and then further amplifying the number of copies of said one or more target nucleic acid sequences in the sample, or an aliquot thereof, by a second nucleic amplification method. In embodiments, a method for amplifying a target nucleic acid sequence in a sample comprises: amplifying the number of copies of one or more target nucleic acid sequences in the sample by a thermocycling nucleic acid amplification method; and then further amplifying the number of copies of said one or more target nucleic acid sequences in the sample, or an aliquot thereof, by a non-thermocycling (e.g., an isothermal) nucleic amplification method. In embodiments, a method for amplifying a target nucleic acid sequence in a sample comprises: amplifying the number of copies of one or more target nucleic acid sequences in the sample by a polymerase chain reaction (PCR) nucleic acid amplification method; and then further amplifying the number of copies of said one or more target nucleic acid sequences in the sample, or an aliquot thereof, by an isothermal nucleic amplification method selected from an isothermal nucleic amplification method as described in International Application No. PCT/US14/30028, filed Mar. 15, 2014; in International Application No. PCT/US14/30034, filed Mar. 15, 2014; in International Application No. PCT/US14/56151, filed Sep. 17, 2014; in International Application No. PCT/US14/30036, filed Mar. 15, 2014; or in International Application No. PCT/US15/50811, filed Sep. 17, 2015.

In further embodiments, a method for amplifying a target nucleic acid sequence in a sample comprises: contacting a sample with a primer, or set of primers which hybridize to a target nucleic acid sequence; amplifying the number of copies of said target nucleic acid sequence in the sample by a first nucleic acid amplification method; and then further amplifying the number of copies of said target nucleic acid sequences in the sample, or an aliquot thereof, by a second nucleic amplification method. Further embodiments include contacting a sample with a plurality of primers, or a plurality of sets of primers, which hybridize to a plurality of target nucleic acid sequences; amplifying the number of copies of said target nucleic acid sequence in the sample by a first nucleic acid amplification method; and then further amplifying the number of copies of said target nucleic acid sequences in the sample, or an aliquot thereof, by a second nucleic amplification method.

In further embodiments, an improved nucleic acid amplification method comprises first utilizing a non-thermocycling (e.g., an isothermal) amplification method to amplify a target nucleic acid sequence, or to amplify a plurality of target nucleic acid sequences, in a sample, and then second applying a thermocycling amplification method to the amplified sample, or aliquot thereof, to further amplify a target nucleic acid sequence, or to amplify a plurality of target nucleic acid sequences, in the sample.

Accordingly, Applicant discloses herein methods, devices, systems, implements (e.g., vessels), and kits for performing nucleic acid amplification. In embodiments, such methods, devices, systems, implements (e.g., vessels), and kits for performing nucleic acid amplification include methods, devices, systems, implements (e.g., vessels), and kits for amplification of nucleic acids from a sample, such as a clinical sample. In embodiments, a portion (e.g., an aliquot) of a sample may be used to provide a nucleic acid for amplification. In embodiments, such a sample may be a blood, urine, saliva, or other clinical sample, or a portion (e.g., an aliquot) of a blood, urine, saliva, or other clinical sample.

Accordingly, in embodiments, Applicant discloses a method for amplifying a target nucleic acid sequence in a sample, comprising:

first amplifying the number of copies of one or more target nucleic acid sequences in the sample by a first nucleic acid amplification method; and next further amplifying the number of copies of said one or more target nucleic acid sequences in the sample, or an aliquot thereof, by a second nucleic amplification method. In embodiments of such methods, said first nucleic acid amplification method comprises a thermocycling nucleic acid amplification method. In embodiments of such methods, said second nucleic acid amplification method comprises an isothermal nucleic amplification method. In embodiments of such methods, said first nucleic acid amplification method comprises a thermocycling nucleic acid amplification method, and said second nucleic acid amplification method comprises an isothermal nucleic amplification method. In embodiments of such methods, said first nucleic acid amplification method comprises a polymerase chain reaction (PCR) nucleic acid amplification method. In embodiments of such methods, the nucleic acid amplified by the PCR amplification method comprises DNA. In embodiments of such methods, the nucleic acid amplified by the PCR amplification method comprises RNA. In embodiments, the nucleic acid may include uracil, and in embodiments may include dideoxyuracil (e.g., may include dideoxyuracil in place of a thymine during amplification). In embodiments of such methods, said second nucleic acid amplification method comprises an isothermal nucleic amplification method.

In embodiments of the methods disclosed herein, primers used in the amplification methods are directed to a single target nucleic acid sequence, and its complement. In embodiments of the methods disclosed herein, primers used in the amplification methods are directed to a plurality of target nucleic acid sequences, and complements thereof.

Accordingly, in embodiments, Applicant discloses a method for detecting a first genetic element and a second genetic element on a common nucleic acid molecule, the method comprising:

performing a first nucleic acid amplification reaction using a first primer and a second primer, wherein both the first primer and the second primer are phosphorylated on the 5' end of the primer, wherein the first primer is complementary to the first genetic element, wherein the second primer is complementary to the second genetic element, and wherein a first reaction product is formed, wherein the first reaction product contains at least a portion of the first genetic element and at least a portion of the second genetic element, wherein the least a portion of the first genetic element and at least a portion of the second genetic element are separated from each other in the first reaction product by X number of nucleotides;

incubating the first reaction product with a ligase enzyme, to form at least a first ligation product containing the first reaction product, wherein within the first ligation product a copy of the at least a portion of the first genetic element and a copy of the at least a portion of the second genetic element are separated from each other by less than X number of nucleotides;

performing a second nucleic acid amplification reaction using a third primer and a fourth primer, wherein the third primer is complementary to the first genetic element, and wherein the fourth primer is complementary to the second genetic element, wherein a second reaction product is formed; and detecting the second reaction product.

Accordingly, in embodiments, Applicant discloses a method for amplifying a polynucleotide template, the method comprising:

A) generating multiple copies of a polynucleotide template in a polymerase chain reaction (PCR) amplification reaction mixture, wherein the PCR amplification reaction mixture comprises a first PCR amplification reaction primer and a second PCR amplification reaction primer, wherein in the PCR amplification reaction mixture, the first PCR amplification reaction primer anneals to the polynucleotide template and the second PCR amplification reaction primer anneals to a polynucleotide which is complementary to the polynucleotide template, and wherein in the PCR amplification reaction mixture, multiple copies of a PCR amplification reaction product are formed, wherein the PCR amplification reaction product is a double-stranded nucleic acid molecule comprising a first strand and a second strand, and wherein a first strand of the PCR amplification reaction product is a copy of the polynucleotide template;

B) incubating copies of the polynucleotide template in a non-thermocycling reaction mixture comprising a non-thermocycling reaction first primer and a non-thermocycling reaction second primer, wherein:

the polynucleotide template comprises a first portion, a second portion and a third portion, wherein the third portion is situated in the polynucleotide template between the first portion and the second portion;

the first primer comprises a first region and a second region, wherein the second region of the first primer is complementary to the first portion of the polynucleotide template; and the second primer comprises a first region and a second region, wherein the second region of the second primer is complementary to a sequence in the PCR amplification reaction product second strand which is complementary to the second portion of the polynucleotide template, the first region of the second primer is complementary to the first region of the first primer, and the first region of the second primer is complementary to the third portion of the polynucleotide template.

In embodiments of the methods disclosed herein, the first portion and second portion of the polynucleotide template are each between 6 and 30 nucleotides in length. In embodiments of such methods, the third portion of the polynucleotide template is between 4 and 14 nucleotides in length. In embodiments of the methods disclosed herein, the number of copies of the polynucleotide template in the non-thermocycling reaction mixture is increased at least 10-fold within 60 minutes of initiation of the method. In embodiments of the methods disclosed herein, a concatemer strand comprising at least three copies of the polynucleotide template is generated during the incubation of the non-thermocycling reaction mixture.

Applicants further disclose herein a vessel, and vessels, comprising therein any one or more components of a reaction mixture provided herein. Applicants further disclose herein a kit, and kits, comprising therein any one or more components of a reaction mixture provided herein.

The assays and methods disclosed herein may be performed on a device, or on a system, for processing a sample. The assays and methods disclosed herein can be readily incorporated into and used in an automated assay device, and in an automated assay system. For example, systems as disclosed herein may include a communication assembly for transmitting or receiving a protocol based on the analyte to be detected (e.g., one or more nucleic acid markers indicative of a virus, a bacterium, or other target) or based on other analytes to be detected by the device or system. In embodiments, an assay protocol may be changed based on optimal scheduling of a plurality of assays to be performed by a device, or may be changed based on results previously obtained from a sample from a subject, or based on results previously obtained from a different sample from the subject. In embodiments, a communication assembly may comprise a channel for communicating information from said device to a computer, said wherein said channel is selected from a computer network, a telephone network, a metal communication link, an optical communication link, and a wireless communication link. In embodiments, systems as disclosed herein may transmit signals to a central location, or to an end user, and may include a communication assembly for transmitting such signals. Systems as disclosed herein may be configured for updating a protocol as needed or on a regular basis.

Devices and systems configured to measure nucleic acid markers (e.g., which may be indicative of a virus, a bacterium, or other target) in a sample of blood according to a method disclosed herein may be configured to determine from analysis of a portion of a sample (e.g., a sample of blood, urine, sputum, tears, or other sample) that comprises a volume of no more than about 1000 µL, or no more than about 500 µL, no more than about 250 µL, or no more than about 150 µL, or no more than about 100 µL, or no more than about 50 µL, or, in embodiments, wherein the volume of the sample comprises no more than about 25 µL, or comprises no more than about 10 µL, or wherein said sample of blood comprises less than about 10 µL. Such devices may be configured to measure target levels, or to detect the presence or absence of a target in a sample, in less than about one hour, or, in embodiments, in less than about 40 minutes, or in less than about 30 minutes.

Devices disclosed herein may be configured to perform an assay for the measurement of a target nucleic acid and also to perform an assay for the measurement of another analyte in the blood sample. Devices disclosed herein may be configured to perform an assay for the measurement of a target nucleic acid molecule, and also to perform an assay comprising the measurement of a morphological characteristic of a blood cell in the blood sample. Devices disclosed herein may be configured to perform an assay for the measurement of a target nucleic acid molecule and also to perform an assay comprising the measurement of another blood analyte, e.g., a vitamin, a hormone, a drug or metabolite of a drug, or other analyte. Such devices may be configured wherein the assays, or the order of performance of assays, that are performed by said device may be altered by communication with another device.

Applicants also disclose systems comprising a device as disclosed herein. In embodiments, the system comprises a device that is configured to perform an assay for the measurement of a target nucleic acid molecule and also to perform an assay for the measurement of another analyte in the sample. In embodiments, the system comprises a device that is configured to perform an assay for the measurement of a target nucleic acid molecule and also to perform an assay for the measurement of a morphological characteristic of a cell in the sample. In embodiments of such a system, assays, or the order of performance of assays, that are performed by said device may be altered by communication with another device.

Methods, systems, devices, kits, and compositions disclosed herein provide rapid assays which require only small amounts of sample, such as only small amounts of blood, urine, tears, sweat, tissue, or other sample. Device and systems disclosed herein are configured to perform such rapid assays which require only small amounts of sample, such as samples or sample portions having volumes of less than about 250 µL, or less than about 200 µL, or less than about 150 µL, or less than about 100 µL. Accordingly, the methods, compositions, devices, and systems provide rapid tests, which require only small biological samples, and thus provide advantages over other methods, compositions, assays, devices, and systems.

Applicant discloses herein compositions comprising one or more of reagents, including primers, nucleotides, dyes, buffers, and other reagents useful for methods disclosed herein. Applicant discloses herein vessels for use in assay devices, assay systems, including automated assay devices, automated assay systems (which may also be termed sample analysis devices and systems, and automated sample analysis devices and systems) useful for methods disclosed herein. Applicant discloses herein implements, tools, and disposables for use in assay devices, assay systems, including automated assay devices and automated assay systems useful for methods disclosed herein. Applicant discloses herein vessels containing one or more of reagents, including primers, nucleotides, dyes, and other reagents useful for methods disclosed herein. Applicant discloses herein kits including compositions comprising one or more of reagents, including primers, nucleotides, dyes, buffers, and other reagents useful for methods disclosed herein; kits including vessels for use in assay devices, assay systems, including automated assay devices and automated assay systems useful for methods disclosed herein; and kits including compositions and vessels for use in assay devices, assay systems, including automated assay devices and automated assay systems useful for methods disclosed herein.

Methods, systems, devices, kits, and compositions disclosed herein provide advantages including greater sensitivity than other methods. Methods, systems, devices, kits, and compositions disclosed herein provide advantages including improved ability to multiplex two or more amplification reactions in a single nucleic amplification device or system (which may be or include, e.g., automated assay devices, automated assay systems, which may also be termed sample analysis devices and systems, and automated sample analysis devices and systems). Methods, systems, devices, kits, and compositions disclosed herein provide advantages including improved ability to amplify two, three, or more target nucleic acids in a single vessel in a first nucleic acid amplification step, and follow up with steps directed to individual target nucleic acids in multiple individual vessels in multiple second nucleic acid amplification steps. Methods, systems, devices, kits, and compositions disclosed herein provide advantages including improved ability to amplify, detect, or identify, and combinations thereof, single nucleotide polymorphisms (SNPs) in target nucleic acids.

Methods, systems, devices, kits, and compositions disclosed herein provide advantages including improved ability to perform PCR without use of dyes in a first nucleic acid amplification step, and to follow up with a second nucleic acid amplification step comprising the use of dyes, for detecting target nucleic acids pursuant to a second nucleic acid amplification step; for example, such methods systems, devices, kits, and compositions may be useful for detection of SNPs.

Methods, systems, devices, kits, and compositions disclosed herein provide advantages including the ability to utilize samples with less pre-processing than might otherwise be required. Methods, systems, devices, kits, and compositions disclosed herein provide advantages including the ability to dilute samples to a greater amount of dilution than might otherwise be required. Methods, systems, devices, kits, and compositions disclosed herein provide advantages including reducing susceptibility to contamination by humans (e.g., operator) other than the subject than might otherwise occur. Methods, systems, devices, kits, and compositions disclosed herein provide advantages including the ability to apply these techniques to the analysis of nasal swabs, where other methods might require nasopharyngeal swabs.

Other goals and advantages of the invention will be further appreciated and understood when considered in conjunction with the following description and accompanying drawings. While the following description may contain specific details describing particular embodiments of the invention, these should not be construed as limitations to the scope of the invention but rather as exemplifications of possible embodiments. For each aspect of the invention, many changes and modifications can be made within the scope of the invention without departing from the spirit thereof.

BRIEF DESCRIPTION OF THE DRAWINGS

In the drawings,

FIG. 6 depicts exemplary primer sequences which may be used with a method provided herein. Figure discloses SEQ ID NOS 22-31, respectively, in order of appearance.

FIG. 8 are exemplary primer sequences which may be used with a method provided herein. Figure discloses SEQ ID NOS 32-33, respectively, in order of appearance.

FIG. 10 shows primer sequences used for a method provided herein. Figure discloses SEQ ID NOS 34-39, respectively, in order of appearance.

FIG. 11A shows a histogram plot for cut-off determination for ZNAT.

FIG. 11B shows a Table for ZNAT results interpretation.

FIG. 12 provides a standard curve showing the quantification of three ZIKV lysates using qRT-PCR to convert plaque-forming units (PFU) and half-maximal tissue culture infective dose ($TCID_{50}$) to genomic copies for three different ZIKV lysates.

FIG. 13 shows results of analytical sensitivity determinations of ZNAT.

FIG. 14 provides a table showing the results of in silico analyses of ZNAT primers against sequenced Zika virus strains.

FIG. 15 shows, in Table form, the results of reactivity/inclusivity analysis of ZNAT in serum samples.

FIG. 16 provides a table showing in silico analysis of Zika preliminary amplification and isothermal primers against prevalent diseases with Zika-like onset symptoms.

FIG. 17 provides a table showing the results of in silico mismatch analyses of ZNAT primers against potentially cross-reacting organisms.

FIG. 18 provides a table showing cross-reactivity and the results of interfering substances analyses of ZNAT in serum.

FIG. 19 shows a table listing the results of ZNAT tests against possible interfering substances in serum.

FIG. 20 provides a table showing the results of analyses of run-to-run contamination of ZNAT in serum.

FIG. 21 provides a table showing the results of concordance studies using ZNAT. Concordance studies results for SPU, CDC RT-PCR, and altona RealStar® assays. Positive and negative percent agreement (PPA and NPA, respectively) values were determined from results that were in agreement between the ZNAT assay run using the SPU and the combined CDC RT-PCR and altona assays for venous serum samples and capillary whole blood samples.

FIG. 22 shows a schematic illustration and a perspective image of a nucleic acid amplification (NAA) detector and thermocycler module as disclosed herein, and includes a schematic illustration of a cross-section of a photodetection system for detecting fluorescence generated by nucleic acid amplification, and further includes (as an inset) an idealized illustration of a plot of fluorescence generated over time (typically as numbers of cycles) by such amplification.

FIG. 23A shows a listing of exemplary steps of methodology for a NAA Zika Assay as disclosed herein.

FIG. 23B shows a listing of performance characteristics of a NAA Zika Assay as disclosed herein, using venous serum samples.

FIG. 24 shows a listing of analytical sensitivity (limit of detection (LoD)) of a NAA Zika Assay as disclosed herein.

FIG. 25 shows a listing of analytical specificity of a NAA Zika Assay as disclosed herein.

FIG. 26 shows a further listing of analytical specificity of a NAA Zika Assay as disclosed herein.

FIG. 27A shows a listing of inclusivity of a NAA Zika Assay as disclosed herein.

FIG. 27B shows a listing of data demonstrating no significant carry-over between different samples when analyzed using automated sample analysis devices and the NAA Zika Assay as disclosed herein.

FIG. 28 shows a clinical study overview of a NAA Zika Assay as disclosed herein.

FIG. 29 shows a comparison (as percent agreement) of a NAA Zika Assay as disclosed herein with CDC RT-PCR with confirmation by altona RealStar®.

FIG. 30 lists some descriptive characteristics of a clinical study using the NAA Zika Assay nucleic acid amplification methods disclosed herein.

FIG. 31 provides a table listing data demonstrating that the results of a clinical study using the NAA Zika Assay nucleic acid amplification methods disclosed herein are consistent with results of comparative assays.

Figure 1:
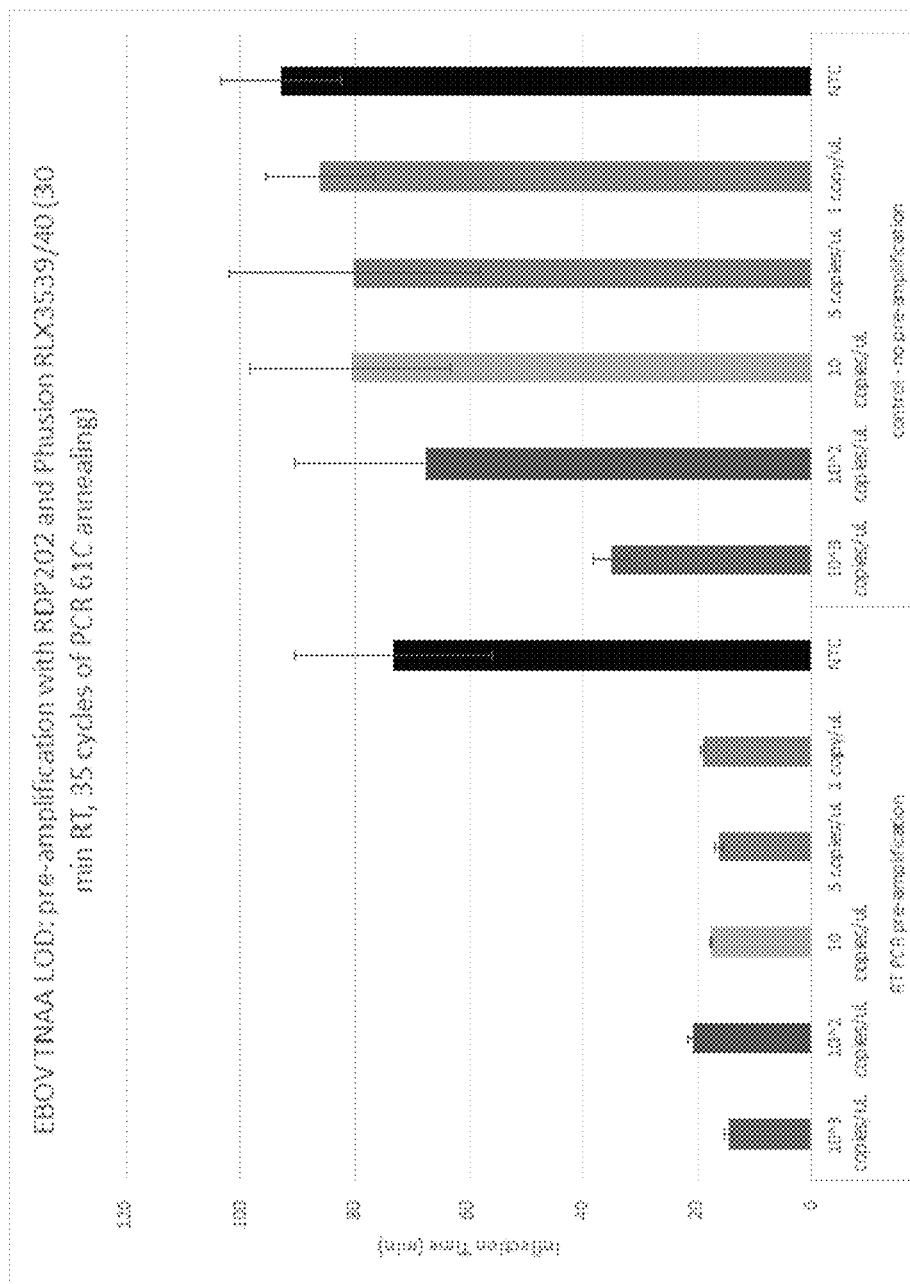
FIG. 1 shows exemplary results according to a method provided herein.

It is noted that the drawings and elements therein are not necessarily drawn to shape or scale. For example, the shape or scale of elements of the drawings may be simplified or modified for ease or clarity of presentation. It should further be understood that the drawings and elements therein are for exemplary illustrative purposes only, and not be construed as limiting in any way.

DETAILED DESCRIPTION

This application hereby incorporates by reference for all purposes and in their entirety the following patent applications: U.S. Provisional Patent Application No. 62/051,912, filed Sep. 17, 2014; U.S. Provisional Patent Application No. 62/051,945, filed Sep. 17, 2014; U.S. Provisional Patent Application No. 62/068,603, filed Oct. 24, 2014; U.S. Provisional Patent Application No. 62/068,605, filed Oct. 24, 2014; U.S. Provisional Patent Application No. 62/151,358, filed Apr. 22, 2015; U.S. Provisional Patent Application No. 61/908,027, filed Nov. 22, 2013; U.S. Provisional Patent Application No. 62/001,050, filed May 20, 2014; and U.S. Provisional Patent Application No. 61/800,606, filed Mar. 15, 2013; U.S. Non-Provisional patent application Ser. No. 14/214,850, filed Mar. 15, 2014; International Patent Application No. PCT/US14/30034, filed Mar. 15, 2014; International Patent Application No. PCT/US14/56151, filed Sep. 17, 2014; International Application No. PCT/US15/50811, filed Sep. 17, 2015; International Application No. PCT/US15/50822, filed Sep. 17, 2015; and U.S. Non-Provisional patent application Ser. No. 15/087,840, filed Mar. 31, 2016.

Provided herein are devices, systems and methods for amplification of nucleic acids. Various features described herein may be applied to any of the particular embodiments set forth below or for any other types systems for or involving nucleic acid amplification. Systems and methods described herein may be applied as a standalone system or method, or as part of an integrated system or method. It shall be understood that different aspects of the disclosed systems and methods can be appreciated individually, collectively, or in combination with each other.

In embodiments, a method provided herein may be performed as follows. A polynucleotide template may be amplified in a first amplification reaction, wherein the first amplification reaction is a thermocycling nucleic acid amplification reaction (e.g., a polymerase chain reaction (PCR)). In the first amplification reaction, a nucleic acid amplification reaction product may be generated (e.g., a PCR amplification reaction product may be generated). Amplification reaction product generated by the first amplification reaction may then be amplified in a second amplification reaction, wherein the second amplification reaction is a non-thermocycling nucleic acid amplification reaction (e.g., an isothermal nucleic acid amplification reaction).

In embodiments, a method provided herein may be performed as follows. A polynucleotide template may be amplified in a first amplification reaction, wherein the first amplification reaction is a polymerase chain reaction (PCR) reaction. In the first amplification reaction, a PCR amplification reaction product may be generated. The PCR amplification reaction product may be a double-stranded nucleic acid molecule comprising a first strand and a second strand, and wherein a first strand of the PCR amplification reaction product is a copy of the polynucleotide template. Next, the PCR reaction product (which comprises a copy of the polynucleotide template) may be used as a template in a non-thermocycling amplification reaction as provided in PCT/US14/56151, in order to generate a non-thermocycling reaction product as described in PCT/US14/56151. Such non-thermocycling reaction products may include concatemers. In embodiments of this method involving a PCR amplification reaction followed by a non-thermocycling amplification reaction, only the non-thermocycling reaction products are detected (not the PCR reaction products). In embodiments, the non-thermocycling reaction products are detected in real-time as they are formed. In embodiments, a method of PCT/US14/56151 may involve a first primer and a second primer. In embodiments, the first primer of a method of PCT/US14/56151 contains a first region and a second region, wherein the first region comprises a 5' end of the primer, the second region comprises a 3' end of the primer, and the second region is complementary to a least a portion of a first strand of a double-stranded nucleic acid template (i.e. a double-stranded nucleic acid molecule, such as a PCR amplification reaction product). In embodiments, the second primer of a method of PCT/US14/56151 contains a first region and a second region, wherein the first region comprises a 5' end of the primer and is complementary to the first region of the first primer, the second region comprises a 3' end of the primer, and wherein the second region is complementary to a least a portion of a second strand of the double-stranded nucleic acid template. In embodiments, the second region of a first primer of a method of PCT/US14/56151 may anneal to a first strand of a PCR amplification reaction product in methods herein in the same way as a first PCR amplification reaction primer anneals to a polynucleotide template strand in PCR amplification reactions provided herein, and the second region of a second primer of a method of PCT/US14/56151 may anneal to a second strand of a PCR amplification reaction product as provided in methods herein in the same way as a second PCR amplification reaction primer anneals to a polynucleotide which is complementary to the polynucleotide template in PCR amplification reaction methods provided herein.

In further, alternative embodiments, a method provided herein may be performed as follows. A polynucleotide template may be amplified in a first amplification reaction, wherein the first amplification reaction is a non-thermocycling nucleic acid amplification reaction (e.g., an isothermal nucleic acid amplification reaction). In the first amplification reaction, a nucleic acid amplification reaction product may be generated. Amplification reaction product generated by the first amplification reaction may then be amplified in a second amplification reaction, wherein the second amplification reaction is a thermocycling nucleic acid amplification reaction (e.g., a PCR reaction).

The methods disclosed herein may be performed by assay devices and assay systems, including automated assay devices and automated assay systems (which may also be termed sample analysis devices and systems, and automated sample analysis devices and systems).

Definitions

As used herein, a "polynucleotide" refers to a polymeric chain containing two or more nucleotides. "Polynucleotides" includes primers, oligonucleotides, nucleic acid strands, etc. A polynucleotide may contain standard or non-standard nucleotides. Typically, a polynucleotide contains a 5' phosphate at one terminus ("5' terminus") and a 3' hydroxyl group at the other terminus ("3' terminus) of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide.

The term "downstream" as used herein in the context of a polynucleotide containing a 5' terminal nucleotide and a 3' terminal nucleotide refers to a position in the polynucleotide which is closer to the 3' terminal nucleotide than a reference position in the polynucleotide. For example, in a primer having the sequence: 5' ATAAGC 3', the "G" is downstream from the "T" and all of the "A"s.

The term "upstream" as used herein in the context of a polynucleotide containing a 5' terminal nucleotide and a 3' terminal nucleotide, refers to a position in the polynucleotide which is closer to the 5' terminal nucleotide than a reference position in the polynucleotide. For example, in a primer having the sequence: 5' ATAAGC 3', the "T" is upstream from the "G", the "C", and the two "A"s closest to the "G".

As used herein, "nucleic acid" includes both deoxyribonucleic acid (DNA) and ribonucleic acid (RNA) molecules, including DNA and RNA containing non-standard nucleotides. A "nucleic acid" contains at least one polynucleotide (a "nucleic acid strand"). A "nucleic acid" may be single-stranded or double-stranded. Acronyms and abbreviations related to nucleic acids as used herein have their standard meanings (e.g., "mRNA" refers to messenger RNA, "ssDNA" refers to single-stranded DNA, "dsDNA" refers to double-stranded DNA, etc.).

As used herein "cDNA" refers to DNA molecules ("complementary DNA") produced by reverse transcription of an RNA molecule. Such reverse transcription produces a DNA molecule having a nucleotide sequence that is the same as the nucleotide sequence of that RNA molecule, with the exception that where the RNA molecule has a uracil moiety (U) the DNA molecule has instead a thymine (T). A cDNA produced by reverse transcription of an RNA molecule is complementary to the complement of that RNA molecule.

The term "primer" as used herein refers to a polynucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an inducing agent such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is a poly-deoxyribonucleotide. The primer must be sufficiently long to prime the synthesis of extension products in the presence of the inducing agent. The exact lengths of the primers will depend on many factors, including temperature, source of primer and use of the method. For example, for diagnostics applications, depending on the complexity of the target sequence, the polynucleotide primer typically contains about 10-30 or more nucleotides, or about 15-25 or more nucleotides, although it may contain fewer nucleotides. For other applications, the polynucleotide primer is typically shorter, e.g., 7-15 nucleotides. Such short primer molecules generally require cooler temperatures to form sufficiently stable hybrid complexes with template.

As used herein, when a first polynucleotide is described as "annealed", "annealing" or the like to a second polynucleotide, the entirety of the first polynucleotide or any portion thereof may anneal to the second polynucleotide, and vice versa.

The "Tm" indicates the annealing temperature for a particular primer set; a primer set may have a different Tm than other primer sets, or may have the same Tm as another primer set. In many cases, Tm is typically between about 45° C. to about 80° C., or between about 50° C. to about 75° C.

As used herein, "reverse transcriptase" (RT) refers to an enzyme which can be used to produce a DNA molecule that is complementary to a RNA molecule. The act of producing such a DNA molecule from an RNA template is termed "reverse transcription". Where a target nucleic acid is a RNA molecule, and DNA is desired (e.g., for use with PCR amplification methods), a cDNA molecule corresponding to the target RNA may be generated by reverse transcription.

As used herein, a "concatemer" refers to a nucleic acid molecule which contains within it two or more copies of a particular nucleic acid, wherein the copies are linked in series. Within the concatemer, the copies of the particular nucleic acid may be linked directly to each other, or they may be indirectly linked (e.g. there may be nucleotides between the copies of the particular nucleic acid). In an example, the particular nucleic acid may be that of a double-stranded nucleic acid template, such that a concatemer may contain two or more copies of the double-stranded nucleic acid template. In another example, the particular nucleic acid may be that of a polynucleotide template, such that a concatemer may contain two or more copies of the polynucleotide template.

As used herein, a "target" nucleic acid or molecule refers to a nucleic acid of interest. A target nucleic acid/molecule may be of any type, including single-stranded or double stranded DNA or RNA (e.g. mRNA).

As used herein, "complementary" sequences refer to two nucleotide sequences which, when aligned anti-parallel to each other, contain multiple individual nucleotide bases which can pair with each other according to standard base-pairing rules (e.g. A-T, G-C, or A-U), such that molecules containing the sequences can specifically anneal to each other. It is not necessary for every nucleotide base in two sequences to be capable of pairing with each other for the sequences to be considered "complementary". Sequences may be considered complementary, for example, if at least 30%, 40%, 50%, 55%, 60%, 65%, 70%, 75%, 80%, 85%, 90%, 95%, 98%, 99%, or 100% of the nucleotide bases in two sequences can pair with each other when the sequences are optimally aligned for complementation. In addition, sequences may still be considered "complementary" when the total lengths of the two sequences are significantly different from each other. For example, a primer of 15 nucleotides may be considered "complementary" to a longer polynucleotide containing hundreds of nucleotides if multiple individual nucleotide bases of the primer can pair with nucleotide bases in the longer polynucleotide when the primer is aligned anti-parallel to a particular region of the longer polynucleotide. Additionally, "complementary" sequences may contain one or more nucleotide analogs or nucleobase analogs. As used herein, "perfectly complementary" or "perfect complementation" or the like refers two sequences which are 100% complementary to each other (i.e. where there are no mis-matches between the nucleotides of the sequences when the sequences are paired for maximum complementation).

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Homology" or "homologous" as used herein in the context of two or more polypeptide or polynucleotide sequences, can mean that the sequences have a specified percentage of residues that are either i) the same, or ii) conservative substitutions of the same residue, over a specified region. Conservative substitutions include substitutions of one amino acid by an amino acid of the same group, and include substitutions of one amino acid by an amino acid as an exemplary or as a preferred substitution as known in the art. In determining homology of two sequences, identical residues and homologous residues are given equal weight. The percentage can be calculated by optimally aligning the two sequences, comparing the two sequences over the specified region, determining the number of positions at which either identical or homologous residues occur in both sequences to yield the number of matched positions, dividing the number of matched positions by the total number of positions in the specified region, and multiplying the result by 100 to yield the percentage of sequence homology. In cases where the two sequences are of different lengths or the alignment produces one or more staggered ends and the specified region of comparison includes only a single sequence, the residues of the single sequence are included in the denominator but not the numerator of the calculation.

As used herein, in the context of two or more polymeric molecules (e.g. nucleic acids, proteins), "corresponds to", "corresponding to", and the like refers to polymeric molecules or portions thereof which have the same or similar sequence of component elements (e.g. nucleotides, amino acids). For example, if a first nucleic acid is described as containing a region which "corresponds to" the sequence of a second nucleic acid, the relevant region of the first nucleic acid has a nucleotide sequence which is the same or similar to the sequence of the second nucleic acid.

As used herein, the term "isolated" as applied to proteins, nucleic acids, or other biomolecules refers to a molecule that has been purified or separated from a component of its naturally-occurring environment (e.g. a protein purified from a cell in which it was naturally produced). An "isolated" molecule may be in contact with other molecules (for example, as part of a reaction mixture). As used herein, "isolated" molecules also include recombinantly-produced proteins or nucleic acids which have an amino acid or nucleotide sequence which occurs naturally. "Isolated" nucleic acids include polypeptide-encoding nucleic acid molecules contained in cells that ordinarily express the polypeptide where, for example, the nucleic acid molecule is at a chromosomal location different from that of natural cells. In some embodiments, "isolated" polypeptides are purified to at least 50%, 60%, 70%, 80%, 90%, 95%, 98%, or 100% homogeneity as evidenced by SDS-PAGE of the polypeptides followed by Coomassie blue, silver, or other protein staining method.

As used herein, a nucleic acid molecule which is described as containing the "sequence" of a template or other nucleic acid may also be considered to contain the template or other nucleic acid itself (e.g. a molecule which is described as containing the sequence of a template may also be described as containing the template), unless the context clearly dictates otherwise.

As used herein, when a first polynucleotide is described as "annealed", "annealing" or the like to a second polynucleotide, the entirety of the first polynucleotide or any portion thereof may anneal to the second polynucleotide, and vice versa.

As used herein, a reference to "treating" a given object to a condition or other object or the like refers to directly or indirectly exposing the given object to the recited condition or other object. Thus, while a "treating" step may involve a distinct related action (e.g. adding an enzyme to a vessel, shaking a vessel, etc.), not every "treating" step requires a distinct related action. For example, a reaction involving one or more reagents can be set up in a vessel, and once the reaction has been initiated, multiple events or steps may occur in the vessel without further human or mechanical intervention with the contents of the vessel. One or more of these multiple events or steps in the vessel may be described as "treating" an object in the vessel, even if no separate intervention with the contents of the vessel occurs after the initiation of the reaction.

As used herein, the term "Zika" refers to Zika virus, and the acronym "ZIKV" also refers to Zika virus. ZIKV is a member of the Flavivirus genus of viruses (family Flaviviridae). Other members of the genus include dengue virus (DENV), West Nile Virus (WNV), Japanese encephalitis virus (JEV), yellow fever virus (YFV), and tick-borne encephalitic virus (TBEV). Flaviviruses have a single-strand, positive-sense RNA genome that serves both as a genome and messenger RNA. The RNA genome is translated into a single polyprotein that is proteolytically cleaved into three structural proteins (capsid, prM, and envelope) and non-structural proteins NS1 to NS5. The virion contains a nucleocapsid composed of the capsid protein (C) and the RNA genome, surrounded by an icosahedral shell comprising both the envelope (E) glycoprotein and membrane (M) protein or the precursor membrane (prM) protein anchored in a lipid membrane.

A composition may include a buffer. Buffers include, without limitation, phosphate, citrate, ammonium, acetate, carbonate, tris(hydroxymethyl)aminomethane (TRIS), morpholino) propanesulfonic acid (MOPS), 3-morpholino-2-hydroxypropanesulfonic acid (MOPSO), 2-(N-morpholino) ethanesulfonic acid (MES), N-(2-Acetamido)-iminodiacetic acid (ADA), piperazine-N,N'-bis(2-ethanesulfonic acid) (PIPES), N-(2-Acetamido)-2-aminoethanesulfonic acid (ACES), cholamine chloride, N,N-Bis(2-hydroxyethyl)-2-aminoethanesulfonic acid (BES), 2-[[1,3-dihydroxy-2-(hydroxymethyl)propan-2-yllaminol ethanesulfonic acid (TES), 4-(2-hydroxyethyl)-1-piperazine ethanesulfonic acid (HEPES), acetamidoglycine, tricine (N-(2-Hydroxy-1,1-bis (hydroxymethyl)ethyl)glycine), glycinamide, and bicine (2-(Bis(2-hydroxyethyl)amino)acetic acid) buffers. Buffers include other organic acid buffers in addition to the phosphate, citrate, ammonium, acetate, and carbonate buffers explicitly mentioned herein.

An article of manufacture may comprise a container; and a composition contained within the container, wherein the composition comprises a nucleic acid molecule (such as, e.g., a primer directed to a target related to ZIKV). An article of manufacture may comprise a container; and a composition contained within the container, wherein the composition comprises a nucleic acid molecule (such as, e.g., a primer directed to a target related to ZIKV). An article of manufacture may comprise a container; and a composition contained within the container, wherein the composition comprises a nucleic acid molecule (such as, e.g., a primer directed to a target related to ZIKV). The containers may be formed from a variety of materials such as glass or plastic, and may have a sterile access port (for example the container may be an intravenous solution bag or a vial having a stopper pierceable by a hypodermic injection needle). The article of manufacture may further comprise a label or package insert on or associated with the container indicating that the composition may be used to detect the presence of a nucleic acid molecule (such as, e.g., a primer directed to a target related to ZIKV) in a sample.

Hybrid Nucleic Acid Amplification Methods

In embodiments, provided herein is method for amplification of a target nucleic acid, wherein the method includes at least two different nucleic acid amplification processes. In embodiments, a target nucleic acid may be first be amplified by a first nucleic acid amplification method which involves thermocycling, and then some or all of the target nucleic acid amplified in the thermocycling reaction may then be used for a second nucleic acid amplification reaction, wherein the second nucleic acid amplification reaction is an isothermal amplification reaction. For example, a target nucleic acid may be first amplified in a polymerase chain reaction ("PCR") amplification reaction (described, for example, in U.S. Pat. No. 4,683,202). PCR amplification methods are thermocycling amplification methods.

Then, following amplification by a PCR method, some or all of the amplified target nucleic acid from the PCR reaction may be used in an isothermal nucleic acid amplification reaction, such as is described in, for example, any of International Application No. PCT/US14/30028, filed Mar. 15, 2014, International Application No. PCT/US14/30034, filed Mar. 15, 2014, International Application No. PCT/US14/56151, filed Sep. 17, 2014, or International Application No. PCT/US14/30036, filed Mar. 15, 2014, are each herein incorporated by reference in their entirety for all purposes. For brevity hereafter, the isothermal nucleic acid amplification methods described in PCT/US14/30028, in PCT/US14/30034, in PCT/US14/56151, and in PCT/US14/30036 are collectively termed "NAA" methods.

The present methods improve (i.e., lower) the limit of detection (LOD) of nucleic acid amplification assays. That is, the presence of smaller numbers of target nucleic acid sequences in a sample can be detected when pre-amplification by thermal-cycling methods are applied to the sample, and then isothermal nucleic acid amplification methods are applied, as compared to when isothermal methods are applied to a sample without such pre-amplification. As few as 1 copy per microliter of target nucleic acid has been detected in samples using PCR followed by NAA methods.

PCR Methods

Polymerase chain reaction ("PCR") methods (see, e.g. U.S. Pat. No. 4,683,202) are popular methods for the amplification of nucleic acids. PCR methods are in vitro methods that can be used to amplify specific polynucleotide sequences, including genomic DNA, single-stranded cDNA, and mRNA among others. As described in U.S. Pat. Nos. 4,683,202, 4,683,195, and 4,800,159 (hereby incorporated herein by reference), PCR typically comprises treating separate complementary strands of a target nucleic acid with two polynucleotide primers to form complementary primer extension products on both strands that act as templates for synthesizing copies of the desired nucleic acid sequences. By repeating the separation and synthesis steps in an automated system, essentially exponential duplication of the target sequences can be achieved.

To successfully perform a PCR reaction, the reaction must be performed at multiple different temperatures. This requires hardware or other mechanisms for repeatedly changing the temperature of the PCR reaction. In embodiments where the target nucleic acid is RNA, reverse transcription PCR (rtPCR) may be used.

As used herein, PCR refers to any of the nucleic acid amplification methods in which a target nucleic acid (typically a double-stranded deoxyribonucleic acid) is exposed to a thermostable DNA polymerase during multiple thermal cycles, and in which multiple copies of the target nucleic acid (typically including copies of nucleic acid sequences disposed between a first target region on one strand of a double-stranded target nucleic acid and a second target region on the complementary strand of a double-stranded target nucleic acid) are produced, amplifying the target nucleic acid. Thermal cycles typically include low temperature portions (typically at temperatures between about 40° C. and about 59° C., or between about 45° C. and about 55° C.), intermediate temperature portions (typically at temperatures between about 60° C. and about 74° C.), and higher temperature portions (typically at temperatures between about 75° C. and about 99° C., or between about 80° C. and about 95° C.). For example, some PCR reactions include a) incubation of a mixture including target molecules and primers at high temperature (e.g., about 90° C. to about 95° C.) to denature the target DNA; b) cooling the mixture to an intermediate temperature (e.g., about 50° C. to about 60° C.) to allow annealing between the primers and target DNA; and c) in the presence of DNA polymerase, generating extensions of the primers (e.g., by action of the polymerase at, e.g. temperatures of about 65° C. to about 75° C.); and repeating this cycle of steps a), b), and c). Steps a), b), and c) together may be termed a "thermal cycle".

Amplification occurs with each thermal cycle, and, following multiple cycles, significant amplification of the target nucleic acid molecule produces large numbers of DNA copies of the target sequence. PCR requirements include a DNA polymerase (e.g., a thermostable DNA polymerase), deoxynucleotides (typically as deoxynucleotide tri-phosphates ("dNTPs") such as dATP, dTTP, dGTP, and dCTP), and appropriate buffer solutions. Where a target nucleic acid is an RNA target, reverse transcriptase (RT) may be used to produce a DNA copy of the RNA, and PCR applied to the DNA copies.

Reverse transcription PCR (RT-PCR) refers to methods for amplifying RNA targets, in which copy DNA molecules (cDNAs) are produced from RNA target polynucleotides by application of reverse transcriptase, and PCR is applied to the cDNA copies to amplify the cDNA copies for detection and/or amplification of the target polynucleotide. RT-PCR requirements include a reverse transcriptase, a DNA polymerase (e.g., a thermostable DNA polymerase), deoxynucleotides (typically as dNTPs such as dATP, dTTP, dGTP, and dCTP), and appropriate buffer solutions.

Real-time PCR refers to PCR amplification methods in which the progress, or extent, of target amplification is monitored during the course of the assay (e.g., at each thermal cycle). Progress of the amplification reactions may be monitored, for example, detecting the amount of fluorescence or absorbance of reporter molecules. Suitable reporter molecules include intercalating dyes (which are detectable when bound to double-stranded DNA, or to the minor groove of DNA, such as ethidium bromide and SYBR Green dye); fluorogenic probes, such as self-quenching dyes, or dye pairs (the pairs including a dye and a quencher) attached to primers (which fluoresce when the primer is bound to target, but do not produce significant fluorescence when not hybridized to target nucleic acid molecules); and other reporter molecules.

As used herein, "rRT-PCR" refers to reverse-transcription real-time PCR. rRT-PCR is real-time PCR applied to RNA targets, using reverse-transcription PCR to amplify nucleic acids based on RNA target molecules, and monitoring the amplification using real-time PCR methods. Reverse-transcription PCR methods provide the DNA substrate required for PCR by contacting a sample, under the appropriate conditions, with a reverse transcriptase and producing cDNA copies of RNA molecules in the sample.

NAA Methods

It will be understood that complete description of the isothermal nucleic acid amplification methods termed herein "NAA methods" is to be found in U.S. Patent Application Publication 2014/0295440, in U.S. Patent Application Publication 2015/0140567, in U.S. Patent Application Publication 2016/0060673, in U.S. Patent Application Publication 2016-0060674, in U.S. Patent Application Publication 2016/0076069, and in U.S. Patent Application Publication 2016/0201148 (each of which is hereby incorporated by reference in theirs entireties); however, these methods are also briefly summarized in the following.

NAA methods of nucleic acid amplification may be applied to double-stranded DNA. However, target nucleic acid molecules need not be limited to double-stranded DNA targets; for example, double-stranded DNA for use in NAA methods described herein may be prepared from viral RNA, or mRNA, or other single stranded RNA target sources, by reverse transcriptase. In further example, double-stranded DNA for use in NAA methods described herein may be prepared from single-stranded DNA targets by DNA polymerase. Such methods may be applied as an initial step, prior to application of the NAA methods discussed below.

Amplification of a double-stranded DNA target, for example, begins with a primary double-stranded DNA to be amplified (termed the "primary nucleic acid" in the following). The primary nucleic acid contains a target region termed a template region; the template region has a template sequence. Such a double-stranded template region contains a first DNA strand and a complementary second DNA strand, and includes a 5' terminal nucleotide in one strand and a 3' terminal nucleotide in the other strand that are complementary to each other.

A first primer and a second primer are provided which each have template-binding regions and tail regions; the primer template-binding regions are complementary to the target template regions. The tail regions of the primers may contain three components: a) the 5' terminal nucleotide of the primer, b) an innermost nucleotide, wherein the innermost nucleotide is downstream from the 5' terminal nucleotide, and c) a middle section between the 5' terminal nucleotide and the innermost nucleotide, comprising one or more nucleotides. In addition, at least portions of the two primer tail regions may be complementary to each other when properly aligned.

It should be noted that although the tail region of the second primer may contain a nucleotide sequence which is complementary to the nucleotide sequence of the tail region of the first primer, typically, products formed by the annealing of the first primer and second primer are not desirable or useful for methods or compositions provided herein. Accordingly, in some embodiments, steps may be taken to minimize the formation of first primer-second primer annealed products. Such steps may include, for example, not pre-incubating a first primer and a second primer under conditions where the primers may anneal for an extended period of time before initiating a method provided herein.

The primary nucleic acid may be treated with a polymerase and a first copy of the first primer under conditions such that the template-binding region of the first copy of the first primer anneals to the first strand of the nucleic acid template. Under these conditions, an extension product of the first copy of the first primer is formed. The polymerase, which may have strand displacement activity, may catalyze the formation of the extension product of the first copy of the first primer. The first copy of the first primer may be covalently linked to the synthesized extension product, such that the first copy of the first primer (which is complementary to the first strand of the nucleic acid template) becomes part of the molecule described herein as the "extension product of the first copy of the first primer." The template-binding region but not the tail region of the first copy of the first primer anneals to the first strand of the nucleic acid template. Examples of conditions suitable for polymerase-based nucleic acid synthesis are known in the art and are provided, for example, in *Molecular Cloning: A Laboratory Manual*, M. R. Green and J. Sambrook, Cold Spring Harbor Laboratory Press (2012), which is incorporated by reference herein in its entirety.

The extension product of the first copy of the first primer may be treated with a polymerase (which may have strand displacement activity) and with the second primer under conditions such that the template-binding region of the second primer anneals to the extension product of the first copy of the first primer. In this way, an extension product of the second primer may be formed. The polymerase may displace the first strand of the nucleic acid template from the extension product of the first copy of the first primer during the synthesis of the extension product of the second primer. The second primer may be covalently linked to the synthesized extension product, such that the second primer becomes part of the molecule described herein as the "extension product of the second primer." The extension product of the second primer is complementary to the extension product of the first copy of the first primer. The template-binding region but not the tail region of the second primer may anneal to the extension product of the first copy of the first primer when the second primer anneals to the extension product of the first copy of the first primer.

The extension product of the second primer may be treated with a polymerase (which may have strand displacement activity) and a second copy of the first primer so as to form an extension product of the second copy of the first primer. During the generation of the extension product of the second copy of the first primer, the second copy of the first primer may be covalently linked to the synthesized extension product, such that the second copy of the first primer becomes part of the molecule described herein as the "extension product of the second copy of the first primer." The extension product of the second copy of the first primer is complementary to the extension product of the second primer.

Generation of the extension product of the second copy of the first primer may result in the generation of a molecule comprising the extension product of the second copy of the first primer and the extension product of the second primer, which may be referred to herein as the "secondary nucleic acid." A secondary nucleic acid may comprise the 3' terminal region of the extension product of the second primer (and the complement thereof) and may comprise the 3' terminal region of the extension product of the second copy of the first primer (and the complement thereof). Secondary nucleic acid molecules include sequences of the template region adjacent to tail sequences. In embodiments, double-stranded nucleic acids are produced in which complementary template and tail region sequences line up. In practice, multiple copies (e.g., two or more) of the secondary nucleic acid are produced by any process whereby a nucleic acid having the general structure of the secondary nucleic acid may be generated, including by practice of NAA methods discussed herein.

Thus, pairs of copies of the secondary nucleic acid may be provided. Further numbers of copies may then be generated, for example, by repetition of the foregoing steps and methods. For example, the full process as described above for generating a secondary nucleic acid from a primary nucleic acid may be repeated two times, in order to generate a two pairs of copies of the secondary nucleic acid; further repetitions may be performed to amplify the number of copies further, e.g., to exponentially amplify the number of copies (e.g., by powers of two).

In addition, since the secondary nucleic acid molecules include sequences of the template region adjacent to tail sequences, partially double-stranded nucleic acids may be produced in which tail region sequences hybridize and line up. Since these tail region sequences are attached to single-stranded template regions, a cross-over structure having two nucleic acid strands together held by the hybridized tail region sequences is produced. These cross-over structures may be extended by a polymerase to form extension products of both component strands. These extension products which may be referred to as "concatemer strands." Two concatemer strands may be annealed together, and may be collectively referred to as a concatemer; such concatemers may contain two or more copies of the nucleic acid template.

In some embodiments, even longer concatemers may be formed. For example, concatemers may anneal together; or two concatemer molecules may form a cross-over structure similar to those formed by the shorter molecules termed concatemer strands, as discussed above, followed by a larger concatemer molecule containing four copies of the nucleic acid template. In another example, a secondary nucleic acid and a concatemer may form a cross-over structure, followed by a larger concatemer molecule containing three copies of the nucleic acid template. In some embodiments, multiple different concatemers of multiple different lengths may be simultaneously generated.

Thus, concatemers generated according to such methods may be of any length of nucleotides. In some embodiments, concatemer molecules generated herein may be at least 30, 40, 50, 60, 70, 80, 90, 100, 150, 200, 250, 300, 400, 500, 600, 700, 800, 900, 1000, 1500, 2000, 3000, 4000, 5000, 6000, 7000, 8000, 9000, 10,000, 15,000, 20,000, or 25,000 nucleotides in length. Concatemers generated according to such methods may contain any number of copies of a nucleic acid template. In some embodiments, concatemer molecules generated herein may contain at least 2, 3, 4, 5, 6, 7, 8, 9, 10, 11, 12, 13, 14, 15, 16, 17, 18, 19, 20, 25, 30, 35, 40, 45, 50, 60, 70, 80, 90, or 100 copies of a nucleic acid template. Further examples are provided, and greater detail of these and other examples, is provided in U.S. Patent Application 61/800,606, filed Mar. 15, 2013.

Detection of Reactions

Progress of a method provided herein may be monitored in multiple different ways. In one embodiment, a reaction may be assayed for a nucleic acid amplification product (e.g. for the level of the product or the rate of its generation). In another embodiment, a reaction may be assayed for the activity of a polymerase along a nucleic acid template (e.g. for movement of a polymerase along a template strand). Thus, in some embodiments, events of a method provided herein may observed due to the accumulation of product from a method (which may be during or after completion of steps of the method), or due to detectable events occurring during the steps of a method.

The presence of amplified nucleic acids can be assayed, for example, by detection of reaction products (amplified nucleic acids or reaction by-products) or by detection of probes associated with the reaction progress.

In some embodiments, reaction products may be identified by staining the products with a dye. In some embodiments, a dye may have greater fluorescence when bound to a nucleic acid than when not bound to a nucleic acid. In some embodiments, a dye may intercalate with a double-stranded nucleic acid or it may bind to an external region of a nucleic acid. Nucleic acid dyes that may be used with methods and compositions provided herein include, for example, cyanine dyes, PicoGreen®, OliGreen®, RiboGreen®, SYBR® dyes, SYBR® Gold, SYBR® Green I, SYBR® Green II, ethidium bromide, dihydroethidium, BlueView™, TOTO® dyes, TO-PRO® dyes, POPO® dyes, YOYO® dyes, BOBO® dyes, JOJO® dyes, LOLO® dyes, SYTOX® dyes, SYTO® dyes, propidium iodide, hexidium iodide, methylene blue, DAPI, acridine orange, quinacrine, acridine dimers, 9-amino-6-chloro-2-methoxyacridine, bis-benzimide dyes, Hoechst dyes, 7-aminoactinomycin D, actinomycin D, hydroxystilbamidine, pyronin Y, Diamond™ dye, GelRed™, GelGreen™ and LDS 751.

Methods of detecting the presence of a target marker, such as, e.g. a virus such as a flu virus, a bacterium such as a *Staphylococcus aureus* bacterium, or other biological target may be detected in a sample are disclosed herein, wherein the presence of a plurality of possible targets are tested from a single sample within a short period of time. In embodiments, the plurality of possible targets comprise at least 5 possible targets, or at least 10 possible targets, or at least 15 possible targets, or at least 20 possible targets, or at least 25 possible targets, or at least 30 possible targets, or at least 35 possible targets, or at least 40 possible targets, or at least 45 possible targets, or at least 50 possible targets, or at least 55 possible targets, or at least 60 possible targets, or at least 64 possible targets, or at least 65 possible targets, or more. In embodiments, a short period of time is a period of time that is five hours or less, or is four hours or less, or is three hours or less, or is two hours or less, or is one hour or less, or is 50 minutes or less, or is 40 minutes or less, or is 30 minutes or less, or is 20 minutes or less, or is 10 minutes or less, or is 5 minutes or less.

In some embodiments, reaction products may be identified by analysis of turbidity of amplification reactions for example, where increased turbidity is correlated with formation of reaction products and reaction by-products (e.g. pyrophosphate complexed with magnesium).

In some embodiments, reaction products may be identified by separating a reaction performed according to a method herein by gel electrophoresis, followed by staining of the gel with a dye for nucleic acids. The dye may be any nucleic acid dye disclosed herein or otherwise known in the art.

In some embodiments, any method or composition known in the art for the detection of nucleic acids or processes associated with the generation of nucleic acids may be used with methods and compositions provided herein.

In some embodiments, a nucleic acid probe which contains a nucleotide sequence complementary to a portion of a nucleic acid template strand (or strand having a similar or identical sequence) and which contains one or both of a fluorescent reporter (fluorophore) and a quencher are included in a reaction provided herein.

In an example, a nucleic acid probe may contain a fluorescent reporter at its 5' or 3' terminus, and a quencher at the other terminus.

In another example, a nucleic acid probe may contain a fluorescent reporter at its 5' or 3' terminus, and it may be annealed to a nucleic acid primer containing a quencher. The nucleic acid primer containing a quencher may contain the quencher at a position in the primer such that when the nucleic acid probe is annealed to the primer, the fluorescent reporter is quenched.

In probes containing a fluorescent reporter and quencher pair, the fluorescent reporter and quencher may be selected so that the quencher can effectively quench the reporter. In some embodiments, a fluorescent reporter is paired with a quencher where the emission maximum of the fluorescent reporter is similar to the absorption maximum of the quencher. Fluorophores that may be used as the fluorescent reporter include, for example, CAL Fluor Gold, CAL Fluor Orange, Quasar 570, CAL Fluor Red 590, CAL Fluor Red 610, CAL Fluor Red 610, CAL Fluor Red 635, Quasar 670 (Biosearch Technologies), VIC, NED (Life Technologies), Cy3, Cy5, Cy5.5 (GE Healthcare Life Sciences), Oyster 556, Oyster 645 (Integrated DNA Technologies), LC red 610, LC red 610, LC red 640, LC red 670, LC red 705 (Roche Applied Science), Texas red, FAM, TET, HEX, JOE, TMR, and ROX. Quenchers that may be used include, for example, DDQ-I, DDQ-II (Eurogentec), Eclipse (Epoch Biosciences), Iowa Black FQ, Iowa Black RQ (Integrated DNA Technologies), BHQ-1, BHQ-2, BHQ-3 (Biosearch Technologies), QSY-7, QSY-21 (Molecular Probes), and Dabcyl.

In some embodiments, a method provided herein may be monitored in an apparatus containing a light source and an optical sensor. In some situations, the reaction may be positioned in the path of light from the light source, and light absorbed by the sample (e.g. in the case of a turbid reaction), scattered by the sample (e.g. in the case of a turbid reaction), or emitted by the sample (e.g. in the case of a reaction containing a fluorescent molecule) may be measured.

In embodiments, the sample may be diluted prior to testing for the presence of a plurality of disease-causing agents. In embodiments, such dilution of a sample is greater for subjects who have a condition which indicates they may have higher levels of disease-causing agents than subject who do not have that condition, or than subjects who have a different condition.

Systems and Devices for Detection of Targets in Samples

The assays and methods disclosed herein may be performed on a device, or on a system, for processing a sample. In embodiments, Applicants disclose herein systems and devices suitable for use in performing methods disclosed herein. The assays and methods disclosed herein can be readily incorporated into and used in device for processing a sample, or a system for processing a sample, which may be an automated assay device, or may be an automated assay system. Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be an automated assay device. A device may be an automated assay device. An automated assay device may be configured to facilitate collection of a sample, prepare a sample for a clinical test, or effect a chemical reaction with one or more reagents or other chemical or physical processing, as disclosed herein. An automated assay device may be configured to obtain data from a sample. An automated assay device may be configured to transmit data obtained from a sample. An automated assay device may be configured to analyze data from a sample. An automated assay device may be configured to communicate with another device, or a laboratory, or an individual affiliated with a laboratory, to analyze data obtained from a sample.

An automated assay device may be configured to be placed in or on a subject. An automated assay device may be configured to accept a sample from a subject, either directly or indirectly. A sample may be, for example, a blood sample (e.g., a sample obtained from a fingerstick, or from venipuncture, or an arterial blood sample), a urine sample, a biopsy sample, a tissue slice, stool sample, or other biological sample; a water sample, a soil sample, a food sample, an air sample; or other sample. A blood sample may comprise, e.g., whole blood, plasma, or serum. An automated assay device may receive a sample from the subject through a housing of the device. The sample collection may occur at a sample collection site, or elsewhere. The sample may be provided to the device at a sample collection site.

In some embodiments, an automated assay device may be configured to accept or hold a cartridge. In some embodiments, an automated assay device may comprise a cartridge. The cartridge may be removable from the automated assay device. In some embodiments, a sample may be provided to the cartridge of the automated assay device. Alternatively, a sample may be provided to another portion of an automated assay device. The cartridge and/or device may comprise a sample collection unit that may be configured to accept a sample.

A cartridge may include a sample, and may include reagents for use in processing or testing a sample, disposables for use in processing or testing a sample, or other materials. Following placement of a cartridge on, or insertion of a cartridge into, an automated assay device, one or more components of the cartridge may be brought into fluid communication with other components of the automated assay device. For example, if a sample is collected at a cartridge, the sample may be transferred to other portions of the automated assay device. Similarly, if one or more reagents are provided on a cartridge, the reagents may be transferred to other portions of the automated assay device, or other components of the automated assay device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as an automated assay device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the automated assay device. The sample, reagent, or aliquot thereof can be deposited at a location on or within the automated assay device. Sample and reagent, or multiple reagents, may be mixed using a sample handling system in a similar manner. One or more components of the cartridge may be transferred in an automated fashion to other portions of the automated assay device, and vice versa.

A device, such as an automated assay device, may have a fluid handling system. A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

An automated assay device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. An automated assay device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

An automated assay device may be configured to run one or more assay on a sample, and to obtain data from the sample. An assay may include one or more physical or chemical treatments, and may include running one or more chemical or physical reactions. An automated assay device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

An automated assay device may be configured to perform a plurality of assays on a sample. In embodiments, an automated assay device may be configured to perform a plurality of assays on a single sample. In embodiments, an automated assay device may be configured to perform a plurality of assays on a single sample, where the sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. An automated assay device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

An automated assay device may perform nucleic acid assays, including isothermal nucleic acid assays (e.g., assays for detecting and measuring nucleic acid targets in a sample, including DNA and RNA targets). In embodiments, an automated assay device may perform nucleic acid assays as disclosed in U.S. patent application Ser. No. 14/183,503, filed Feb. 18, 2014; U.S. patent application Ser. No. 14/214,850, filed Mar. 15, 2014; International Patent Application PCT/US2014/030034, filed Mar. 15, 2014; and in International Patent Application PCT/US2014/056151, filed Sep. 17, 2014. An automated assay device may perform antibody assays, including enzyme-linked immunosorbent assays (ELISA), and other assays for detecting and measuring the amounts of proteins (including antibodies), peptides, and small molecules in samples. An automated assay device may perform general chemistry assays, including electrolyte assays (e.g., assays for detecting and measuring the amounts of electrolytes such as sodium and potassium in a sample).

An automated assay device may be configured to detect one or more signals relating to the sample. An automated assay device may be configured to identify one or more properties of the sample. For instance, the automated assay device may be configured to detect the presence or concentration of one analyte or a plurality of analytes or a disease condition in the sample (e.g., in or through a bodily fluid, secretion, tissue, or other sample). Alternatively, the automated assay device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device, such as an automated sample analysis device, may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample.

The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, an automated assay device may be configured to transmit data obtained from a sample. In embodiments, an automated assay device may be configured to communicate over a network. An automated assay device may include a communication module that may interface with the network. An automated assay device may be connected to the network via a wired connection or wirelessly. The network may be a local area network (LAN) or a wide area network (WAN) such as the Internet. In some embodiments, the network may be a personal area network. The network may include the cloud. The automated assay device may be connected to the network without requiring an intermediary device, or an intermediary device may be required to connect an automated assay device to a network. An automated assay device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

An automated assay device may provide data regarding a sample to, e.g., a health care professional, a health care professional location, such as a laboratory, or an affiliate thereof. One or more of a laboratory, health care professional, or subject may have a network device able to receive or access data provided by the automated assay device. An automated assay device may be configured to provide data regarding a sample to a database. An automated assay device may be configured to provide data regarding a sample to an electronic medical records system, to a laboratory information system, to a laboratory automation system, or other system or software. An automated assay device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by an automated assay device, or analysis of such data, or reports, may be provided to a database, an electronic medical records system, to a laboratory information system (LIS), to a laboratory automation system (LAS), or other system or software.

An example of an integrated system disclosed herein comprises an integrated system for providing testing and diagnosis of a subject suspected of suffering from a disease, said system comprising a means for obtaining a sample (which may include, e.g., a sample collection device comprising a lancet, a syringe, a needle and tube, or other blood collection device; or a nasal swab, a mouth swab (e.g., a cheek swab), a throat swab, a vaginal swab, or other swab, and fluid in which to immerse the swab following contacting the swab with a subject); a cartridge comprising reagents for assays for the disease; a device for running a plurality of assays for detecting a plurality of diseases; a device/means for displaying/communicating the detection of one or more of said diseases. Such integrated systems may be configured for uses wherein the sample is a small volume sample; for uses wherein detection is performed in a short period of time; or for uses both wherein the sample is a small volume sample and wherein detection is performed in a short period of time.

Another example of an integrated system disclosed herein comprises an integrated system for providing testing and diagnosis of a subject suspected of suffering from a respiratory disorder, said system comprising a means for obtaining a sample (which may include, e.g., a nasal swab, a throat swab, a mouth swab (e.g., a cheek swab), a vaginal swab, or other swab, and fluid in which to immerse the swab following contacting the swab with a subject); a cartridge comprising reagents for assays for respiratory disorders; a device for running a plurality of assays for detecting a plurality of respiratory disorders; a device/means for displaying/communicating the detection of one or more of said respiratory disorders. Such integrated systems may be configured for uses wherein the sample is a small volume sample; for uses wherein detection is performed in a short period of time; or for uses both wherein the sample is a small volume sample and wherein detection is performed in a short period of time.

A further example of an integrated system disclosed herein comprises an integrated system for providing testing, diagnosis, and prescription of a subject suspected of suffering from a respiratory disorder, said system comprising a means for obtaining a sample (which may include, e.g., a nasal swab, a throat swab, a mouth swab (e.g., a cheek swab), a vaginal swab, or other swab, and fluid in which to immerse the swab following contacting the swab with a subject); a cartridge comprising reagents for assays for respiratory disorders; a device for running a plurality of assays for detecting a plurality of respiratory disorders; a device/means for displaying/communicating the detection of one or more of said respiratory disorders; and means for providing a prescription for the treatment of a respiratory disorder detected in said sample. Such integrated systems may be configured for uses wherein the sample is a small volume sample; for uses wherein detection is performed in a short period of time; or for uses both wherein the sample is a small volume sample and wherein detection is performed in a short period of time.

A yet further example of an integrated system as disclosed herein comprises an integrated system for providing testing, diagnosis, prescription, and treatment of a subject suspected of suffering from a respiratory disorder, said system comprising a means for obtaining a sample (which may include, e.g., a nasal swab, a throat swab, a mouth swab (e.g., a cheek swab), a vaginal swab, or other swab, and fluid in which to immerse the swab following contacting the swab with a subject); a cartridge comprising reagents for assays for respiratory disorders; a device for running a plurality of assays for detecting a plurality of respiratory disorders; a device/means for displaying/communicating the detection of one or more of said respiratory disorders; means for providing a prescription for the treatment of a respiratory disorder detected in said sample; and means for providing/selling/delivering a treatment (drug/pill/shot) to said subject pursuant to said prescription. Such integrated systems may be configured for uses wherein the sample is a small volume sample; for uses wherein detection is performed in a short period of time; or for uses both wherein the sample is a small volume sample and wherein detection is performed in a short period of time.

Description and disclosure of examples of reagents, assays, methods, kits, devices, and systems which may use, or be used with, the methods, devices, and systems disclosed herein may be found, for example, in U.S. Pat. Nos. 8,088,593; 8,380,541; 8,435,738; 8,475,739; 8,840,838; U.S. patent application Ser. No. 14/183,503, filed Feb. 18, 2014; U.S. patent application Ser. No. 13/933,035, filed Jul. 1, 2013; U.S. patent application Ser. No. 13/769,820, filed Feb. 18, 2013; U.S. patent application Ser. No. 14/183,503, filed Feb. 18, 2014; Patent application Ser. No. 14/214,850, filed Mar. 15, 2014; International Patent Application PCT/US2014/030034, filed Mar. 15, 2014; International Patent Application PCT/US2014/056151, filed Sep. 17, 2014; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. application Ser. No. 13/945,202, filed Jul. 18, 2013, the disclosures of which patents and patent applications are all hereby incorporated by reference in their entireties.

EXAMPLES

The following examples are offered for illustrative purposes only, and are not intended to limit the present disclosure in any way.

Example 1

Thermocycling pre-amplification methods include any suitable thermocycling method, including PCR, reverse-transcriptase PCR (rtPCR), and other PCR methods. Two-step PCR methods include methods with steps of incubating at a first temperature (e.g., between about 38-45° C., or about 42° C.); incubating at a second, raised temperature (e.g., between about 90-105° C., or about 98° C.); thermal cycling between two temperatures where the two temperatures are a) a second, raised temperature (e.g., between about 90-105° C., or about 98° C.) and b) a lower, annealing temperature (Tm, e.g., between about 50° C. to about 80° C.); and then incubating at a third, lower temperature (e.g., a temperature between about 65° C. to about 75° C.). Three-step PCR methods include methods with steps of incubating at a first temperature (e.g., between about 38-45° C., or about 42° C.); incubating at a second, raised temperature (e.g., between about 90-105° C., or about 98° C.); thermal cycling between three temperatures where the three temperatures are a) a second, raised temperature (e.g., between about 90-105° C., or about 98° C.) and b) a lower, annealing temperature (Tm, e.g., between about 50° C. to about 80° C.); and c) a third, lower temperature (e.g., a temperature between about 65° C. to about 75° C.); and then, an incubation at a third, lower temperature (e.g., a temperature between about 65° C. to about 75° C.). Following the last incubation at the third, lower temperature, the amplified sample may be used immediately, or may be stored (e.g., at 4° C.) until needed.

A method as provided herein was performed as follows:

PCR thermal cycling was performed on a sample, where the sample was subjected to thermal cycling as follows:

1) incubated for 30 minutes at 42° C., then.

2) incubated at 98° C. for 2 minutes, followed by 3) 35 repeated thermal cycles as follows:

i) 10 seconds at 98° C., followed by ii) 15 seconds at Tm ° C., followed by iii) 15 seconds at 72° C.; and then, after the 35 cycles, 4) incubated for 2 minutes at 72° C.

In alternative embodiments, the number of repeated cycles in step 3) above may be altered; for example, the number of repeated cycles may be reduced to, e.g., 30, or 25, or 20, or fewer cycles. In other alternative embodiments, the number of repeated cycles in step 3) above may be increased, e.g., to 40, or 45, or 50, or more cycles. In alternative embodiments, step iii) above may be shortened to less than 15 seconds, or may be eliminated altogether. Where step iii) is eliminated, the PCR method becomes a "two-step" PCR method.

Following the above steps 1 to 4, the amplified sample can be immediately used for isothermal amplification (e.g., by NAA methods) or may be stored at 4° C. until needed. Steps 1) to 4) take approximately one hour to complete. The "Tm" indicates the annealing temperature for a particular primer set; a primer set may have a different Tm than other primer sets, or may have the same Tm as another primer set. In many cases, Tm is typically between about 50° C. to about 75° C. For example, in the experiments shown in the figures, Tm was 62° C. for RLX3539/40 primers, and was 72° C. for RLX3547/48 primers.

Primers directed to nucleic acid sequences present in Ebola virus were developed and synthesized. Two primer sets were used in the experiments disclosed herein. Experiments were performed in order to determine the limit of detection (LOD) of target Ebola virus nucleic acid target sequences. These experiments were performed with both pre-amplification primer sets RLX3539/40 and RLX3547/48. For the primer set RLX3539/40, an annealing temperature of 61° C. was used. An annealing temperature of 62° C. may also be used with this primer set. An annealing temperature of 71° C. was used for primer set RLX3547/48.

In embodiments, the primers used for the PCR and the NAA methods may be nested primers, where the nucleic acid targets of one set of primers are internal to (encompassed within) the nucleic acid sequences amplified by the other set of primers. For example, primers used for NAA amplification may be targeted to nucleic acid sequences that are amplified during PCR amplification, i.e., the NAA target nucleic acids are internal to the target nucleic acids to which the PCR primers hybridize.

Primer set RLX3539/40 had the following nucleic acid sequence:

RLX3539
(SEQ ID NO: 1)
TGCCAACTTATCATACAGGC

RLX3540
(SEQ ID NO: 2)
GACTGCGCCACTTTCC

Primer set RLX3547/48 had the following nucleic acid sequence:

RLX3547
(SEQ ID NO: 3)
TGCCAACTTATCATACAGGCCTT

RLX3548
(SEQ ID NO: 4)
TGCCCTTCCAAATACTTGACTGCGCCA

In the "pre-amplification" experiments shown in the figures, rtPCR was used to amplify RNA target nucleic acids in a sample; target nucleic acids were included with PCR reagents to a final concentration of $10^3$, $10^2$, 10, 5, and 1 copy per microliter (4), and PCR amplification performed; 2.5 µL of the resulting reagent, following the amplification, was combined with NAA reagents and isothermal NAA amplification performed. In the "control no pre-amplification" experiments, target nucleic acids were included with NAA reagents to a final concentration of $10^3$, $10^2$, 10, 5, and 1 copy per microliter (4), and isothermal NAA amplification was performed. As shown in the figures, these methods combining PCR pre-amplification with NAA isothermal amplification were able to achieve an LoD of 1 copy/µL (shown as "1c/uL" in the figures); such an LoD means there were 5 copies/RT PCR reaction. See results below for both primers sets.

Detection of target is indicated by the inflection time measured in the NAA assay (note that "NTC" (no-template control) shows an inflection, but at much later times than a specific signal detected for target sequences). Primer set RLX3539/40 was used for the RT-PCR pre-amplification in the experiments shown in FIGS. 1 and 2. As shown in FIG. 1, target nucleic acid sequences were detected in 20 minutes or less for all copy numbers in samples with RT-PCR pre-amplification (left five columns, displaying inflection times for $10^3$, $10^2$, 10, 5, and 1 copy per microliter (4)). In contrast, the inflection times for control experiments (NAA assays without RT-PCR pre-amplification, shown on the right) were all greater than about 35 minutes (all but one were greater than 60 minutes; the shortest inflection time being for the greatest number of copies ($10^3$ copies/µL). Thus, target nucleic acid sequences in samples were more readily detected by the isothermal NAA methods as disclosed herein when the sample was first "pre-amplified" by PCR (results labeled "pre-amplification"), than by the NAA isothermal methods alone.

Figure 2:
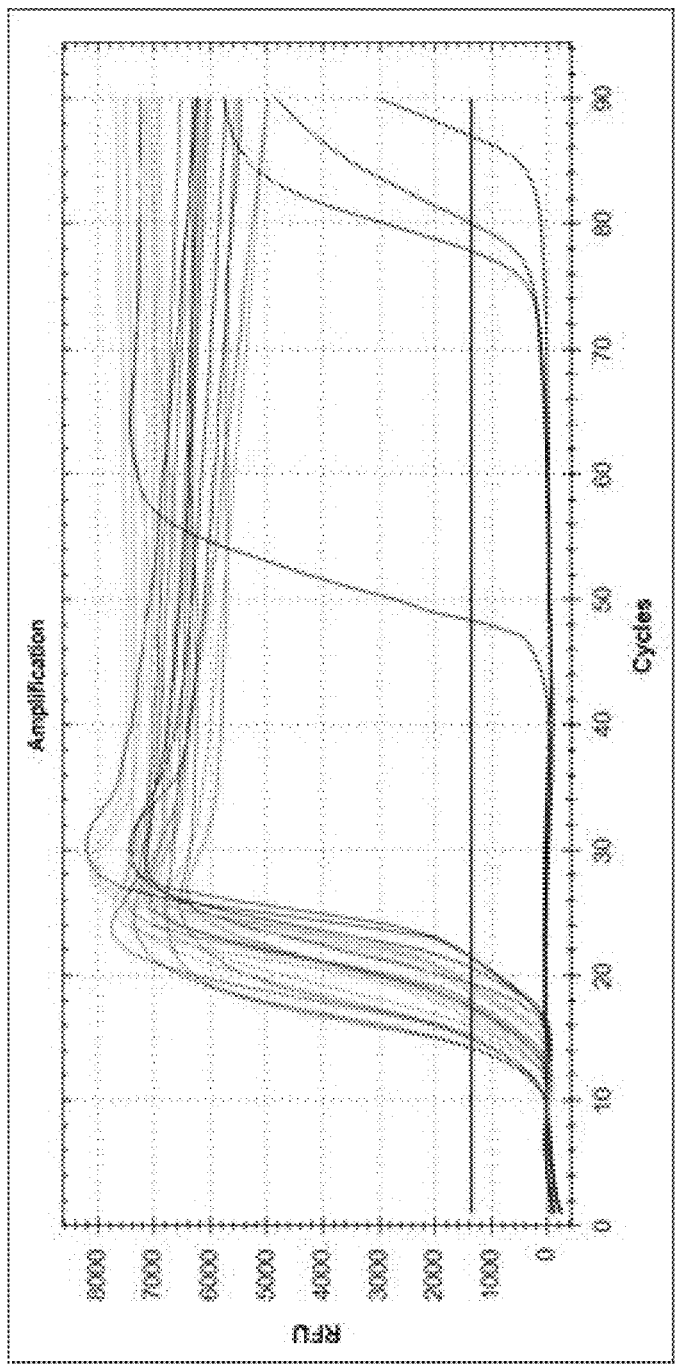
FIG. 2 shows exemplary results according to a method provided herein.

FIG. 2 shows some raw output of the experiments summarized in FIG. 1. The traces shown in FIG. 2 are from NAA assays performed following pre-amplification, with relative fluorescence shown in the vertical direction, and time (as "cycles", where a cycle is about 60 to 90 seconds, i.e., approximately about one minute) in the horizontal direction.

Figure 3:
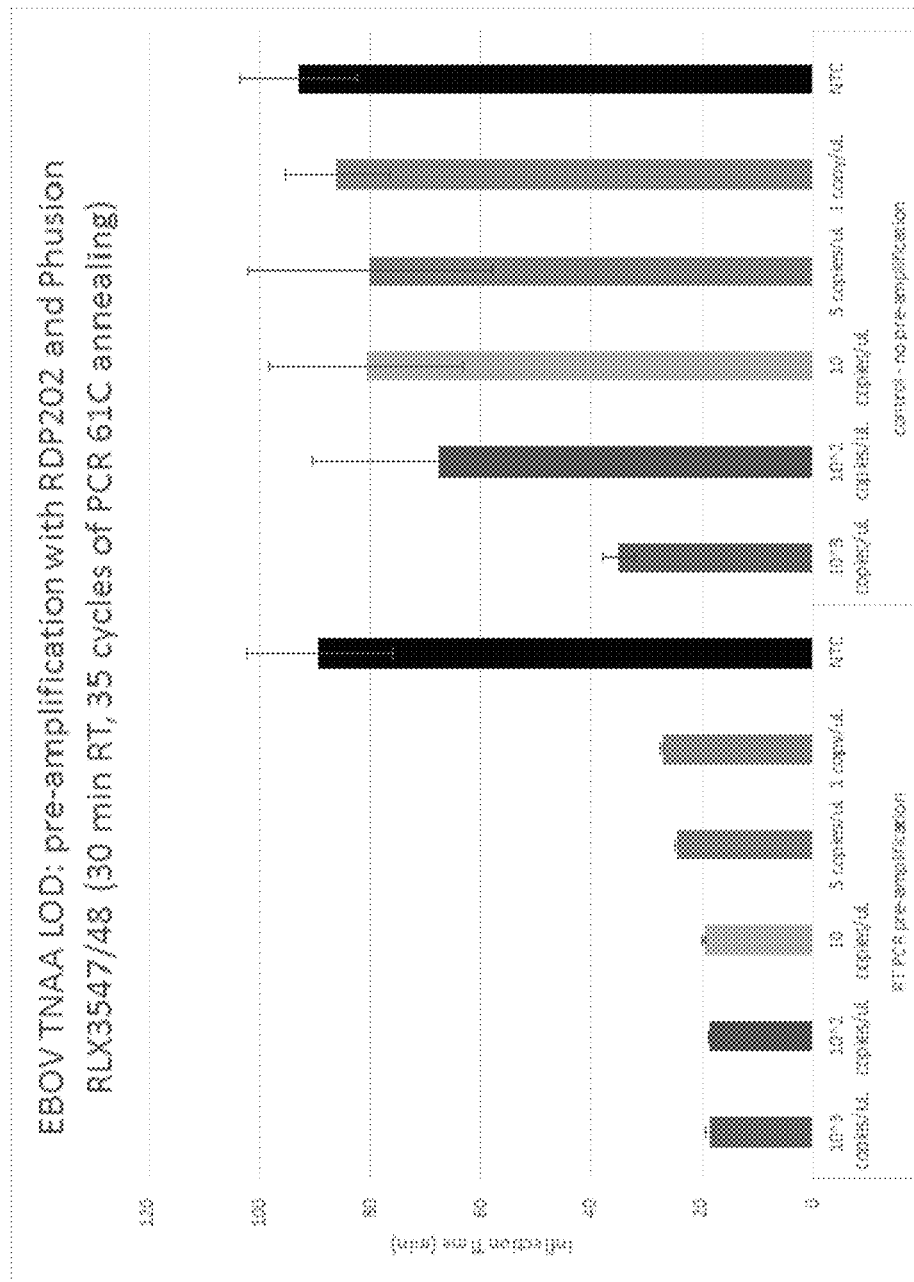
FIG. 3 shows exemplary results according to a method provided herein.
Figure 4:
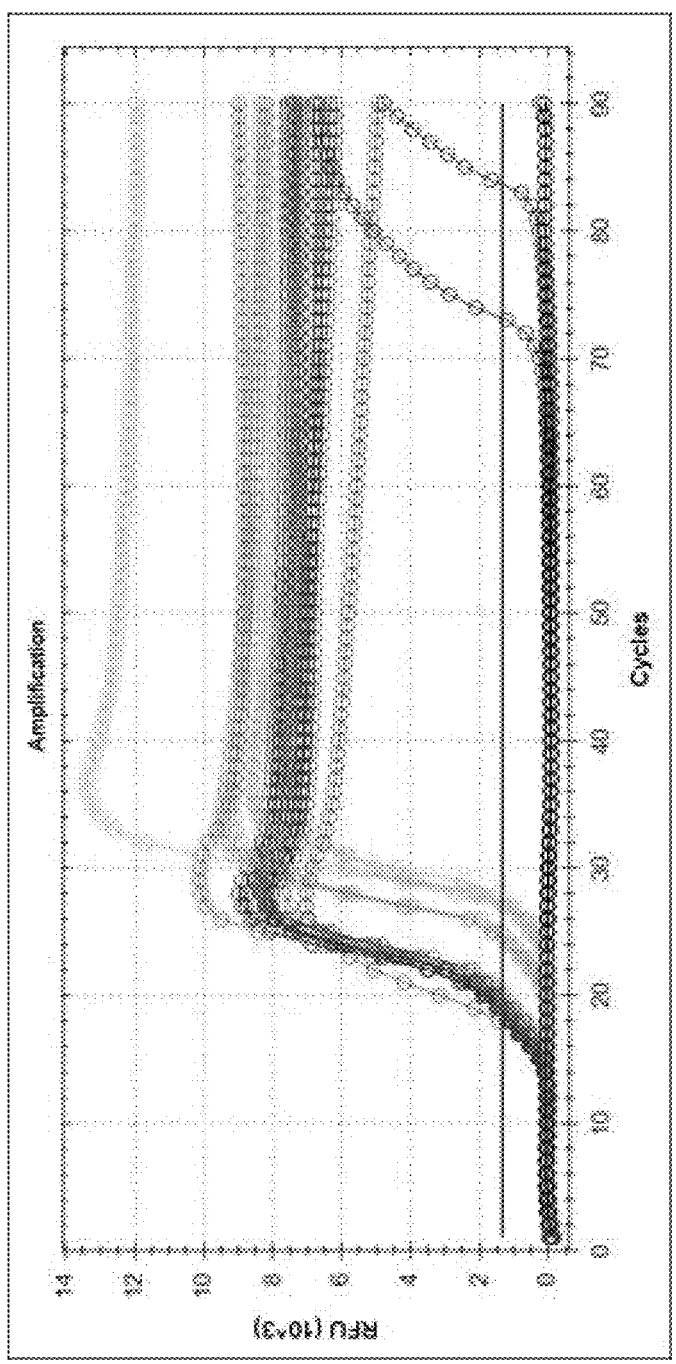
FIG. 4 shows exemplary results according to a method provided herein.
Figure 5:
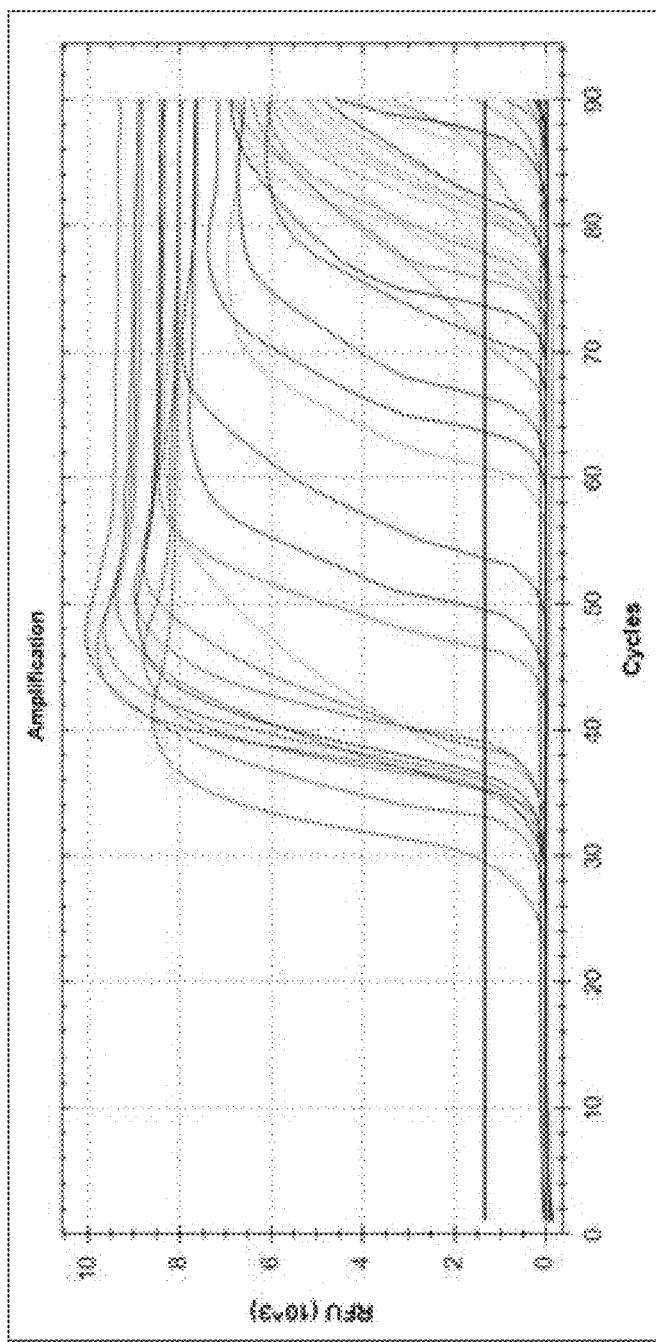
FIG. 5 shows exemplary results according to a method provided herein.

Primer set RLX3547/48 was used for the RT-PCR pre-amplification in the experiments shown in FIGS. 3, 4, and 5. As shown in FIG. 3, target nucleic acid sequences were detected in about 30 minutes or less for all copy numbers in samples with RT-PCR pre-amplification (left five columns, displaying inflection times for $10^3$, $10^2$, 10, 5, and 1 copy per microliter (4)). In contrast, the inflection times for control experiments (NAA assays without RT-PCR pre-amplification, shown on the right) were all greater than about 35 minutes, and all but one, for $10^3$ copies/µL, were greater than 60 minutes. Thus, in these experiments as well, when the sample was first "pre-amplified" by PCR, target nucleic acid sequences in samples were more readily detected by the isothermal NAA methods than by the NAA isothermal methods alone.

FIG. 4 shows some raw output from the NAA assays with pre-amplification (summarized in FIG. 3), with relative fluorescence shown in the vertical direction, and time (as "cycles", where a cycle is about 60 to 90 seconds, i.e., approximately about one minute) in the horizontal direction. In contrast, FIG. 5 shows some raw output from the NAA assays with no pre-amplification (summarized in FIG. 3), with relative fluorescence shown in the vertical direction, and time (as "cycles", where a cycle is about 60 to 90 seconds, i.e., approximately about one minute) in the horizontal direction. Comparison of the traces in FIG. 4 and FIG. 5 illustrates the reduced time for detection (shorter inflection time) when NAA isothermal methods are preceded by RT-PCR as compared to the time for detection (inflection time) for NAA isothermal methods alone (in the absence of RT-PCR pre-amplification).

Example 2

In one non-limiting example, rapid identification of acute and established HIV infection using a single test that is capable of detecting HIV nucleic acids, antibodies, and antigens can have a dramatic impact on public health by helping patients with positive HIV results obtain the care and services they need faster. In one embodiment, a single test for HIV is provided that is capable of detecting HIV nucleic acids, antibodies, and antigens (for both diagnostic and prognostic use), is simple to use on specimens, processed or unprocessed, capable of either or both qualitative and quantitative applications, may be performed in 5 hrs or less, 4 hrs or less, 3 hrs or less, 2 hrs or less, or 60 minutes or less, and suitable for commercial distribution.

In one embodiment, an HIV test of the invention tests for all of the following from a sample obtained from a subject in a single device or with the housing of one device: HIV-1 RNA, HIV-2 RNA, p24 antigen, HIV-1 antibodies, and HIV-2 antibodies. Thus, the HIV test of the invention is also capable of differentiating between HIV-1 and HIV-2 infection. In one embodiment, a simplified sixth-generation HIV test comprises performing all the following tests from one small sample: HIV-1 RNA, HIV-2 RNA, p24 antigen, HIV-1 IgG, HIV-2 IgG, HIV-1 IgM, and HIV-2 IgM.

In one non-limiting example, the sample may be between about 100 to about 200 microliters of blood (venous or capillary). In another non-limiting example, the small sample may be between about 10 to about 100 microliters of blood (venous or capillary). In some embodiments, the blood is pre-processed so that the sample being tested is plasma. In some embodiments, the blood is pre-processed so that the sample being tested is serum. In some embodiments, the blood is pre-processed so that the sample being tested is diluted blood. In some embodiments, the sample being tested is undiluted blood. In some embodiments, the pre-processing occurs on a device separate from the sample processing device. Optionally, the pre-processing and sample processing both occur in one device or within the housing of one device. In an embodiment, the HIV-1 RNA, HIV-2 RNA, p24 antigen, HIV-1 antibodies, and HIV-2 antibodies are tested from a single sample obtained from the subject.

In one non-limiting example, by combining nucleic acid testing and serological testing, this embodiment of the test will provide information to detect acute infections as well as for established infections. Optionally, this HIV test is fully automated and will have on-board quality controls (QC) that are processed in parallel with the patient sample. In one embodiment of the on-board QC, the on-board quality controls will include positive and negative controls as well as the human RNaseP gene to act as a positive control with human clinical specimens to indicate that adequate isolation of nucleic acid resulted from the extraction of the clinical specimen. In one non-limiting example the QC reagents and consumables are contained in the same cartridge that has the reagents and consumables for the HIV test.

In one non-limiting example, this HIV test is designed to be run from a capillary whole-blood sample. Optionally, in a still further embodiment, it should be understood that the test can be configured to run on capillary or venous whole blood, serum, or plasma. In one embodiment, the test is processed automatically by a sample processing without any user intervention. In one embodiment, the test is processed automatically by a sample processing without any user intervention after loading of the sample into the device. Given the ease of sample collection, the ease of running the sample, the high sensitivity/high specificity nucleic acid, antigen, and serologic testing, this embodiment of the test can be used for rapid diagnosis and differentiation of HIV-1 and HIV-2 infections.

By way of one non-limiting example, the steps of processing a sample may comprise
  a. RNA extraction from the sample by a beads-based method is performed;
  b. Reverse transcription (RT) is performed;
  c. Pre-amplification is performed through a series of polymerase chain reaction (PCR) amplification cycles,
  d. Isothermal amplification and detection are performed;
  e. Immunoassays to detect p24, HIV-1 antibodies, and HIV-2 antibodies are performed in parallel to the above nucleic acid testing;
  f. On-board controls are processed in parallel to the sample processing on the instrument.

The immunoassays may be direct or indirect immunoassays and may be an ELISA (enzyme-linked immunosorbent assay). For example, p24 may be detecting using an antibody-sandwich immunoassay using a monoclonal antibody specific for p24. The HIV test of the invention may also be capable of detecting IgG, IgM, or both, antibodies of HIV-1 and HIV-2. In a particular embodiment, the test of the invention is capable of detecting both IgG and IgM antibodies of HIV-1 and HIV-2. In a non-limiting example, both the IgG and IgM antibodies are detected using antigen sandwich immunoassays for HIV-1 and HIV-2. In an embodiment, the immunoassays are capable of distinguishing between HIV-1 and HIV-2 antibodies by, for example, using antigens specific for HIV-1 and HIV-2, respectively. In another embodiment, the HIV tests are capable of distinguishing between antigen reactivity and antibody reactivity by, for example, using different detection reagents, performing the assays separately from one another, and/or different detection methods. The capture reagent (eg. antigen, antibody, etc.) may be immobilized on a solid support, including but not limited to, beads, surface of wells, and inside assay tips.

Further, although many of embodiments herein describe nucleic acid amplification using an isothermal technique, it should be understood that other nucleic acid amplification techniques such as PCR, qPCR, nested PCR, or other nucleic acid detection techniques are not excluded. In another embodiment, the test is capable of distinguishing between HIV-1 and HIV-2 RNA by using primers that are specific to HIV-1 and HIV-2, respectively.

In one non-limiting example, raw data from the testing is transmitted to a data analyzer for interpretation. In one embodiment, the data analyzer is not at the same location as the device that processes the sample using the above steps. Optionally, other embodiments may have the data analyzer in the same location as the sample processor. Optionally, other embodiments may combine the data analyzer and the sample processor in the same device. It should also be understood that in some embodiments, the raw data is in the form of voltage, current, numeric, electronic, optical, digital, or other non-final value that, if intercepted by another party or device, is meaningless unless the intercepting party or device has conversion information or an algorithm to convert such raw data or other readout into health measurements.

In one embodiment, test cartridges are stored refrigerated (4-8° C.) prior to use. Optionally, the test cartridges are stored refrigerated (2-10° C.) prior to use. In one embodiment, the test uses a single cartridge that provides all reagents and consumables used for at least the nucleic acid testing and serological testing. Optionally, the combined test uses a single cartridge that provides all reagents and consumables used for the nucleic acid testing, antibody testing, and antigen testing. Optionally, the combined test uses a single cartridge that provides all reagents and consumables used for the nucleic acid testing, antibody testing, and antigen testing on blood and a tissue sample contained in the cartridge. Optionally, the combined test uses a single cartridge that provides all reagents and consumables used for the nucleic acid testing, antibody testing, and antigen testing on blood and a sample on a nasal swab contained in the cartridge. Optionally, the combined test uses a single cartridge that provides all reagents and consumables used for the nucleic acid testing, antibody testing, and antigen testing on blood and a sample on a throat swab contained in the cartridge. Optionally, the combined test uses a single cartridge that provides all reagents and consumables used for the nucleic acid testing, antibody testing, and antigen testing on capillary blood. Optionally, the combined test uses a single cartridge that provides all reagents and consumables used for the nucleic acid testing, antibody testing, and antigen testing on diluted capillary blood. Optionally, the combined test uses a single cartridge that provides all reagents and consumables used for the nucleic acid testing, antibody testing, and antigen testing on diluted venous blood. Optionally, the combined test uses a single cartridge that provides all reagents and consumables used for the nucleic acid testing, antibody testing, and antigen testing on venous blood.

The HIV test, as described in one embodiment herein, can be deployed at urgent care centers with trained and certified medical staff on-site to perform finger-stick tests and collect samples. Optionally, some may have these test available at locations at retail pharmacies, retail stores, or other locations accessible at location that subjects may visit for other purposes (shopping or the like) during hours when regular doctor offices are closed or even when the doctor offices are open.

In one embodiment, fully automated production facilities can support the production of tests in extremely high volumes (sufficient for processing tens of millions of samples).

In one non-limiting example, the sensitivity of the HIV test will be comparable to if not more sensitive than other FDA-approved nucleic acid tests such as the Abbott Real-Time HIV-1 test. In one embodiment, the limit of detection (LOD) may be as low as 5, 8, 10, 15, 20, 50, 100, 500, or 1000 HIV copies in a sample.

In one embodiment herein, the nucleic acid tests are highly-sensitive for low copy number sensitivity that can be used for rapid diagnosis during acute infection. By way of non-limiting example, the nucleic acid tests in this embodiment are specific to HIV-1 Group M (A-H) and Group 0, and HIV-2 subtypes A and B, respectively.

In one embodiment of the test herein, the turnaround time may be a run time that is less than 60 minutes. The traditional turnaround time for existing nucleic acid testing is 6.5 hours (3.5 hours for extraction and 3 hours for amplification and detection) for individual or pooled nucleic acid testing.

In terms of CLIA status and test complexity, given the ease of sample collection, on-board QC, automated sample processing, and automated analysis and results interpretation, the HIV may be configured for a CLIA waiver or similar waiver from other regulatory body regarding test complexity, while some may opt to run it through CLIA certified or other regulatory agency certified laboratories.

The embodiments herein may dramatically improve the ability to rapidly identify acute and established HIV infection through simplified nucleic acid tests for detecting and quantifying HIV, and thus allow patients to receive care and services faster.

In some embodiments, the HIV test uses a quantitative nucleic acid amplification process. Optionally, some embodiments may use a qualitative nucleic acid amplification process.

Example 3 MRSA Detection

Methicillin-resistant *Staphylococcus aureus* (MRSA) is a type of *Staphylococcus aureus* (*S. aureus*) which can cause infection in humans and is resistant to beta-lactam antibiotics. As a result of its resistance to certain antibiotics, MRSA infections can be difficult to treat.

*S. aureus* bacteria typically become methicillin-resistant through acquiring the mecA gene. The mecA gene is typically located in the staphyloccal cassette chromosome mec (SCCmec), which is a multi-gene, transferrable genomic element. Different types of SCCmec exist, with known SCCmec types ranging in size from approximately 21,000-67,000 nucleotides in length. Generally, within each type of SCCmec, the mecA gene is surrounded by other genes or elements which are other components of the SCCmec. In MRSA bacteria, SCCmec containing the mecA gene is integrated into the *S. aureus* chromosome.

In order identify and control MRSA bacteria, effective reagents and methods for MRSA detection are needed.

Provided herein are systems and methods for MRSA detection. Various features described herein may be applied to any of the particular embodiments set forth below or for any other types systems for or involving MRSA detection. Systems and methods described herein may be applied as a standalone system or method, or as part of an integrated system or method. It shall be understood that different aspects of the disclosed systems and methods can be appreciated individually, collectively, or in combination with each other.

Prior methods for MRSA detection typically separately test a sample for the mecA gene and for genetic material from the *S. aureus* chromosome. If both the mecA gene and *S. aureus* genetic material are found in the sample, a presumptive conclusion is made that MRSA is present. However, this conclusion might not be accurate, because the mecA gene can exist outside of *S. aureus* (as part of the SCCmec, which is transferrable between organisms). Thus, a sample that contains both the mecA gene and *S. aureus* might not actually contain MRSA; instead, it may contain non-MRSA *S. aureus* bacteria, and a different bacteria or free genetic element which contains the mecA gene. This situation thus may give rise to a false-positive identification of MRSA in a sample.

Methods and compositions provided herein address the above problem, and provide methods and compositions for identifying the mecA gene in a *S. aureus* chromosome (and thus, true MRSA).

One approach to identifying a mecA gene in a *S. aureus* chromosome might be to perform, for example, polymerase chain reaction (PCR), where the PCR reaction would contain a sample which might contain MRSA bacteria or MRSA genetic material, and wherein one of the primers for the PCR reaction would anneal to portion of the mecA gene and the other primer for the PCR reaction would anneal to a portion of the *S. aureus* chromosome. If such a PCR reaction yielded a reaction product, it would indicate that both the mecA gene and genetic material from the *S. aureus* chromosome were on the same strand (and thus, that the sample contained true MRSA bacteria). However, typically this approach is not effective, because in most MRSA bacteria, the mecA gene is many thousands of nucleotides away from genetic material of the *S. aureus* chromosome. This is due to the fact that in MRSA, the mecA gene is integrated into the *S. aureus* chromosome as part of the SCCmec, and the mecA gene is typically in an inner portion of the SCCmec, surrounded on both sides by thousands of additional nucleic acids of the SCCmec insert. The relatively large nucleotide distance between the mecA gene and the *S. aureus* chromosome in most MRSA strains generally results in the poor performance of traditional PCR reactions as described above (e.g. with one primer annealing to a portion of the mecA gene and the other primer annealing to a portion of the *S. aureus* chromosome), as traditional PCR and many other nucleic acid amplification techniques are not very effective at amplifying relatively long nucleotide sequences.

Multiple different types of SCCmec have been identified. For instance, the position of the mecA gene may differ between the different SCCmec types; the content of the SCCmec elements may differ between the different SCCmec types, and the locations in the *S. aureus* chromosome where the SCCmec are inserted (e.g. attL and attR) may differ between the different SCCmec types. The mecA gene when present in a *S. aureus* chromosome is typically separated from *S. aureus* genetic material by thousands or even tens of thousands of nucleotides.

Provided herein are improved methods and compositions for identifying the mecA gene in a *S. aureus* chromosome (and thus, true MRSA).

In embodiments, methods provided herein comprise at least two steps: 1) a step to generate a nucleic acid strand wherein at least a portion of the mecA gene and the *S. aureus* chromosome are in close physical proximity to each other within the strand; and 2) a step to perform a nucleic acid amplification method using at least a first primer, a second primer and the nucleic acid strand of step 1), wherein the first primer anneals to a portion of the mecA gene and the second primer anneals to a portion of the *S. aureus* chromosome, and where an amplification product is generated which includes portions of both the mecA gene and the *S. aureus* chromosome.

In embodiments of systems and methods provided herein, a *S. aureus* chromosome or portion thereof containing a SCCmec cassette containing a mecA gene 200 may be provided (referred to as a "MRSA chromosome"). The MRSA chromosome 200 may be incubated with a first primer and a second primer, wherein the first primer is complementary to a portion of the mecA gene (or, optionally, other element of the SCCmec cassette), and the second primer is complementary to a portion of the *S. aureus* chromosome. In addition, one or both of the primers is phosphorylated at the 5' end. The MRSA chrosomosome is incubated in a first DNA amplification reaction with a DNA polymerase having high processivity. An exemplary DNA polymerase with high processivity is phi29 polymerase. The first DNA amplification reaction may be, for instance, an isothermal method. By use of a DNA polymerase with high processivity, at least a small amount of amplification product 202 may be generated. The amplification product from this reaction 202 will contain both *S. aureus* and mecA genetic material, but typically, only a small amount of amplified material 202 will be generated. This amplified material 202 is generally difficult to detect, due to the small amount generated. Accordingly, the amplified material 202 is then incubated with a DNA ligase, which can ligate amplification products 202 together due to the phosphate groups on the 5' end of the primers used for the amplification reaction. Incubation of the amplified material 202 with a ligase may result in two general types of ligation products: a) concatemers 204 formed by the end-to-end ligation of two or more amplification products 202; or b) circularized products 206 formed by the ligation of one end of an amplification product 202 to the other end of the same amplification product 202. With both types of ligation products (204 and 206), the mecA gene is brought into close physical proximity with *S. aureus* genetic material (e.g. attR, ora). Accordingly, both types of ligation products are suitable templates for nucleic acid amplification methods which are most effective at amplification of relatively small amplicons (e.g. 2000 nucleotides or less). Thus, the next step of a method provided herein involves using the ligation products for a second nucleic acid amplification step. This second nucleic acid amplification step will use at least a first primer which anneals to a portion of the mecA gene (or optionally, another portion of the SCCmec cassett), and a second primer which anneals to *S. aureus* genetic material. Various nucleic acid amplification methods may be used for the second nucleic acid amplification step, such as PCR or an amplification method as described in PCT/US14/56151, filed Sep. 17, 2014, which is hereby incorporated by reference in its entirety for all purposes. In embodiments, the first primer and second primer of the second nucleic acid amplification step are different than the first primer and second primer of the first nucleic acid amplification step (which produced product 202). In embodiments, the first primer and second primer of the second nucleic acid amplification step have an opposite orientation as compared to the first primer and second primer of the first nucleic acid amplification step. In embodiments, the first primer and second primer of the second nucleic acid amplification step are the same as the first primer and second primer of the first nucleic acid amplification step.

FIG. 6 provides exemplary primer sequences which may be used with a method provided herein.

In embodiments, all of the steps of methods provided herein may be permitted to occur simultaneously in the same vessel (e.g. all reagents for methods provided herein may be provided in the same vessel at the same time).

In addition to being used for the detection of true MRSA bacteria, the method provided herein may also be used for the detection of other genetic elements in other species or molecules, in which, for example, there are two or more genetic elements which may be on a common nucleic acid strand or part of a common molecule, but for which the elements are separated from each other by a large nucleotide distance. The general approach as provided herein (i.e. to perform a first amplification reaction, followed by a ligation reaction, followed by a second amplification reaction) may be used for a wide range of genetic elements which present a similar structural problem.

In addition, in embodiments, the first amplification reaction provided herein may be omitted, if multiple copies of a molecule containing genetic elements of interest are already present, and such molecules may be ligated together to form structures in which the elements of interest may be readily amplified by, for example, as PCR or an amplification method as described in PCT/US14/56151.

Example 4 SNP Detection

Within Hepatitis C genotype 1a, there is a polymorphic site Q80K in the protease gene, NS3, that is associated with treatment failure with the protease inhibitor boceprevir, which otherwise can be effective in blocking peptide maturation in the virus. Assessing the Q80 polymorphism in the NS3 gene in patients with subtype 1a can be an important part of formulating a treatment plan.

Accordingly, improved reagents and methods for assessing the Q80 polymorphism are needed. In addition, improved reagents and methods for assessing other SNPs are needed.

Provided herein are systems and methods for assessing SNPs. Various features described herein may be applied to any of the particular embodiments set forth below or for any other types systems for or involving assessing SNPs. Systems and methods described herein may be applied as a standalone system or method, or as part of an integrated system or method. It shall be understood that different aspects of the disclosed systems and methods can be appreciated individually, collectively, or in combination with each other.

In embodiments, provided herein are compositions and methods for evaluating a SNP, mutation, or other nucleotide of interest in a target sequence. In some situations, a target sequence may have multiple different polymorphisms which surround the position of the nucleotide of interest. For example, the nucleotide of interest may be located in the 60th nucleotide position of a target sequence of 150 nucleotides (with the 5' most nucleotide being in the first position, the nucleotide next to the 5' most nucleotide being in the second position, etc.).

In embodiments, a nucleotide of interest may be evaluated through use of a method for SNP detection as provided in PCT/US14/56151, filed Sep. 17, 2014, which is hereby incorporated by reference in its entirety for all purposes. In such a method, a primer pair is used to amplify a target nucleic acid containing the nucleotide of interest, wherein each primer contains a tail/first region and a template-binding/second region. In embodiments, the tail of the/first region of the second primer of the primer pair is complementary to a portion of the target nucleic acid including the nucleotide of interest. In a method as disclosed in PCT/US14/56151, the identity of a nucleotide of interest may be determined, for example, by comparing the rate or amount of amplification of a target nucleic acid containing the nucleotide of interest by one or more primer pairs having slightly different nucleotide sequences in the first/tail region of the primer (typically by just a single nucleotide difference between the primer pairs).

However, in some situations, it may be difficult to perform a method for SNP detection as provided in PCT/US14/56151, if there is a lot of sequence variance in the target nucleic acid one or more positions near the nucleotide of interest. Such positions, for example, may be in the region corresponding to the template-binding regions of the first and/or second primer. If the primers as described in PCT/US14/56151 for SNP detection are not able to readily bind to a target nucleic acid sequence, the method disclosed therein may not be effective for SNP detection.

Accordingly, provided herein are compositions and methods which facilitate the identification of SNPs. In a first step, a region of a target nucleic acid containing the nucleotide of interest is amplified by a first amplification reaction (such as PCR), to generate a first amplification product. In this first amplification reaction, relatively long primer pairs (e.g. each primer contains at least 15, 20, 25, 30, 35, 40, 45, 50, 55, 60, 65, 70, 80, 90, or 100 nucleotides) are used to amplify the target nucleic acid. The long primers may tolerate relatively large amounts of sequence diversity in the template-binding regions (i.e. because the primers are long, they may still anneal to a target sequence, even if multiple nucleotides are mis-matched). Importantly, in the first amplification reaction, neither of the primers is to anneal to the exact position of the nucleotide/SNP of interest (i.e. the primers should only anneal to areas near the SNP of interest). This is because with methods provided herein, it is not desirable to change the identity of the nucleotide/SNP of interest (since it is desired to identify the nucleotide/SNP of interest). Once a first amplification product is generated in the first amplification reaction, the first amplification product will have a generally known nucleotide sequence (as a result of knowing the nucleotide sequence of the primers used in the first amplification reaction to generate the first amplification product). However, the identity of the nucleotide/SNP of interest will still be unknown in the first amplification product, since neither of the primers used in the first amplification reaction annealed to the location of the nucleotide/SNP of interest. The first amplification product may then incubated with primers as provided in PCT/US14/56151 for SNP detection. These primers may be designed to have regions that are complementary to sequences that are known to be present in the first amplification product, based on the fact that the first amplification product was generated through use of primers of known sequences. The identity of a SNP/nucleotide of interest may then be determined as described in PCT/US14/56151.

Figure 7:
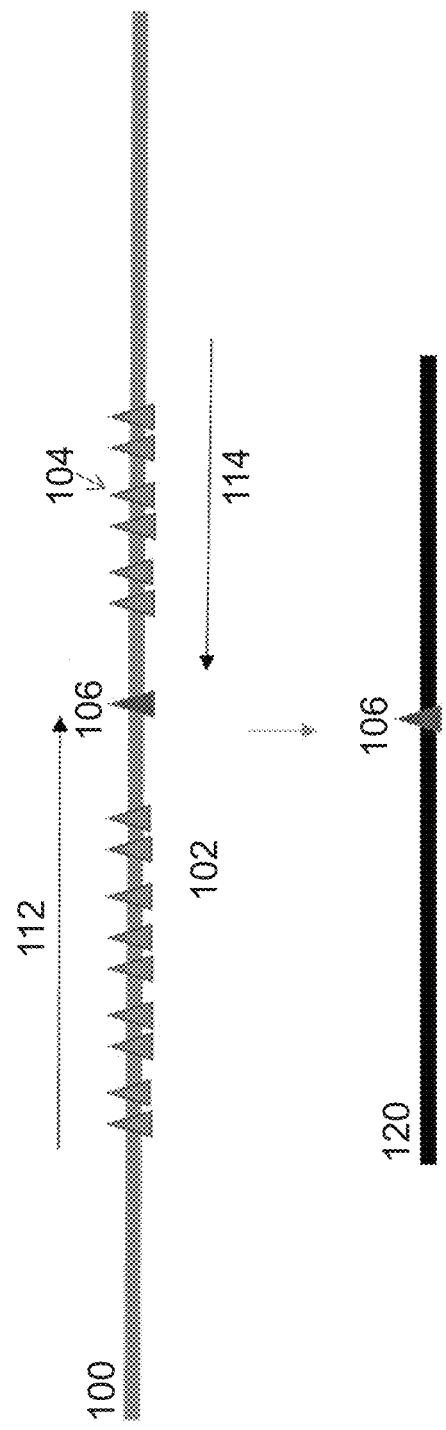
FIG. 7 is a general schematic of method provided herein.

FIG. 7 provides a general schematic of a method provided herein. A nucleic acid strand 100 containing a target nucleic acid 102 may be provided. The target nucleic acid 102 may contain multiple polymorphisms/variant nucleotides 104. The target nucleic acid 102 also contains a nucleotide/SNP of interest 106. The target nucleic acid is incubated with a first primer 112 and second 114 primer, in order to generate a first amplification product 120. The first amplification product 120 will have a generally known nucleotide sequence, since it was amplified with the first primer 112 and second primer 114 (which have known nucleotide sequences). During the process of generating the first amplification product 120, the multiple polymorphisms/variant nucleotides 104 are replaced by the nucleotides of the first primer 112 and second primer 114. However, the first amplification product 120 still has an unknown nucleotide/SNP of interest 106. The first amplification product 120 may then be used in a method as described in PCT/US14/56151 for SNP detection.

In embodiments, methods provided herein may be used to assess a SNP in the polymorphic site Q80K in the Hepatitis C protease gene, NS3. FIG. 8 provides exemplary primer sequences which may be used as part of a method for assessing the Q80K site. Methods provided herein may be used to assess SNPs in many different target nucleic acids, wherein the target nucleic acids have a high level of sequence variability.

Figure 9:
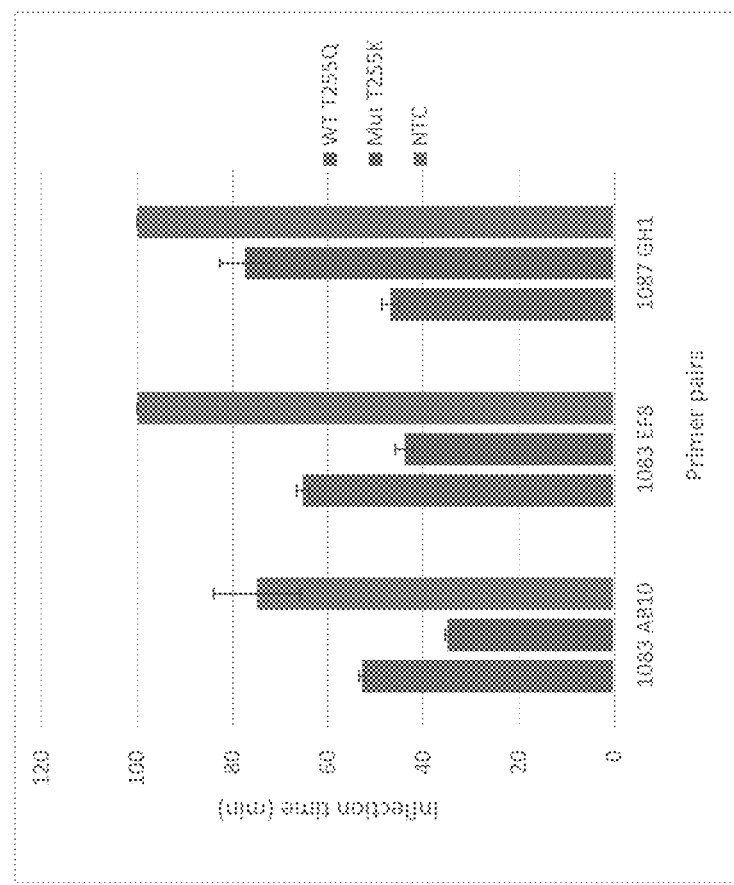
FIG. 9 shows results from a method provided herein.

FIG. 9 provides results from steps of a method performed as described herein. FIG. 10 provides primer sequences used for the experiments of FIG. 9. In addition, nucleotide sequences also used for the results of FIG. 9 were as follows:

T255Q Sequence:

```
                                              (SEQ ID NO: 5)
GGAACGAGGACCATCGCATCACCCAAGGGTCCTGTTATCCAGATGTATA

CCAATGTAGACCAAGACCTCGTGGGCTGGCCCGCTCCTCAAGGTGCCCG

CTCATTGACACCCTGCACCTGCG.
```

T255K Sequence:

```
                                              (SEQ ID NO: 6)
GGAACGAGGACCATCGCATCACCCAAGGGTCCTGTTATCCAGATGTATA

CCAATGTAGACAAAGACCTCGTGGGCTGGCCCGCTCCTCAAGGTGCCCG

CTCATTGACACCCTGCACCTGCG
```

In embodiments, all of the steps of methods provided herein may be permitted to occur simultaneously in the same vessel (e.g. all reagents for methods provided herein may be provided in the same vessel at the same time).

Example 5 Zika Virus Detection

Zika virus (ZIKV) has received global scrutiny following an outbreak in South America, causing a spectrum of neurologic complications including microcephaly. Current ZIKV diagnostic procedures begin with initial observation of clinical symptoms, including any combination of fever, conjunctivitis, and rash. The range of ZIKV RNA concentrations in sera of symptomatic patients is about 900 to about 729,000 copies/mL, as detected by rRT-PCR (Lanciotti, et al., *Emerg Infect Dis.* 2008; 14(8):1232-1239). ZIKV rRT-PCR dan also detect ZIKV in urine and saliva for up to two additional weeks after ZIKV becomes undetectable in blood (Zhang, et al., *Lancet Infect Dis.* 2016; 16(6):641-642; Barzon, et al., *Euro Surveill.* 2016; 21(10)).

This Example provides a ZIKV nucleic acid amplification test (ZNAT) that detects ZIKV RNA in capillary EDTA whole blood (CWB) samples and venous serum samples.

Methods:

The Zika nucleic acid amplification test system (ZNAT) uses nested primers in two sequential reactions that comprise RT-PCR amplification followed by isothermal amplification and detection. This test is performed using a single-use cartridge that is processed on a fully automated, transportable device (an automated, diagnostic platform) with fully integrated sample preparation and processing capabilities. The test system can process and amplify nucleic acid from venous serum or capillary whole blood, requires minimal handling, and is complete in about 2 hours. The analytical performance of the ZNAT was compared to the Centers for Disease Control and Prevention (CDC) and altona Diagnostics Zika RT-PCR tests (altona assay) using serum and capillary whole blood (CWB) samples from the Dominican Republic, Colombia, and United States, including from symptomatic and pregnant subjects.

Results:

The ZNAT had analytical sensitivities of 320 and 480 genomic copies/mL for capillary whole blood and serum, respectively. The ZNAT detected multiple Zika strains, including the current South American PRVABC59 strain and two African strains. The test did not cross-react with other flaviviruses or pathogens that produce Zika-like symptoms. The ZNAT successfully detected Zika virus in both venous serum and capillary blood of symptomatic patients from the Dominican Republic and Colombia. When compared to results from both the CDC Zika RT-PCR and altona Diagnostics RealStar® assays, ZNAT exhibited 100% sensitivity (67 of 67 samples [95% CI 94.6-100]) with 95.6% specificity (109 of 114 samples [95% confidence interval (CI) 90.1-98.6]) for serum samples and 98.0% sensitivity (50 of 51 samples [95% CI 89.7-99.7]) and 100.0% specificity (56 of 56 samples [95% CI 93.6-100.0]) for capillary whole blood samples.

The ZNAT performance is equivalent to existing Zika diagnostics. These results demonstrate that ZNAT can provide rapid and accurate results and can provide efficient diagnostic testing in regions of immediate need without requiring the presence or intervention of molecular-biology trained technicians. The combination of capillary collection and shipping technology with low cost nucleic acid analysis facilitates effective screening in remote locations otherwise difficult to access.

Materials and Methods

ZNAT Workflow:

Disposable, barcoded test cartridges contained all necessary assay reagents and consumables. Sample collection units (SCUs, Thermos, Palo Alto, Calif.) containing CWB or serum were inserted into test cartridges (see next section) and the cartridges were inserted into the sample processing unit (SPU), which is an automated sample analysis device. The fully automated SPU processed blood samples for RNA extraction and nucleic acid amplification. Reagents and consumables used for the test were returned back into the cartridge upon assay completion; the assay cartridge was then ejected and retrieved by trained personnel and disposed of as bio-hazardous waste. The run time for analysis (e.g., from time of sample insertion into the automated sample analysis device to the analytical result was approximately 2 hours.

Specimen Collection:

Venous blood was collected using standard procedures into serum separator tubes (BD Biosciences #367987, Franklin Lakes, N.J.) by trained phlebotomists and then centrifuges at 1300×g for 15 minutes. Capillary whole blood (CWB) was collected after fingersticks with disposable lancets (BD Biosciences #366593, Franklin Lakes, N.J.) and with EDTA-coated Sample Collection Devices (SCDs) (Theranos, Palo Alto, Calif.); SCDs contained detachable SCUs. Serum was obtained from 102 symptomatic subjects from the Dominican Republic (D.R.) and Colombia (Boca Biolistics, Pompano Beach, Fla.; Allied Research Society, Miami Lakes, Fla.). Matched subject CWB, serum, and urine samples were obtained from 30 subjects from the D.R (Boca Biolistics, Pompano Beach, Fla.). Serum samples from 25 febrile U.S. patients were obtained from commercial vendors (Access Biologicals LLC, Vista, Calif.). 78 serum and 77 CWB samples were obtained from Zika-asymptomatic U.S. volunteers. All samples were collected after written, informed consent with approval from an ethics committee.

ZNAT assay workflow: All necessary assay reagents and consumables were assembled in disposable, barcoded assay cartridges. SCUs containing serum or capillary whole blood were inserted into assay cartridges (see next section) and the cartridges were inserted into the SPU. The sample-to-result fully-automated SPU extracted RNA from samples and performed nucleic acid amplification. Reagents and consumables used for the assay were returned back into the cartridge upon assay completion; the assay cartridge was then ejected and disposed of as bio-hazardous waste.

Blood Sample Preparation for ZNAT:

Each SCU, comprised of two identical storage vessels, contained a total of 160 µL of CWB or serum. As necessary, live ZIKV (strain PRVABC59, Centers for Disease Control, Atlanta, Ga.) was added into CWB or serum blood samples. ZIKV was added manually for serum samples or automatically within SPUs for CWB samples. The SPU also added MS2 bacteriophage to the serum and CWB samples to serve as a positive control for sample preparation/RNA extraction and thermal cycling-based amplification.

For CWB samples with added ZIKV, ZIKV stocks at 27.7× the desired concentration, diluted in Tris-EDTA (TE) buffer pH 8.0 (IDT DNA, Coralville, Iowa) with 1 U/µL of RNase-inhibitor (Theranos, Palo Alto, Calif.), were manually pipetted into a specified vessel within the ZNAT cartridge before insertion into a SPU. Within the SPU, the device spiked 3 µL of 27.7×ZIKV stock into each of the two vessels of the SCU, with each containing approximately 80 µL of CWB to yield a 1:27.7 dilution. For venous serum samples with added ZIKV, live ZIKV was diluted with serum matrix and then manually pipetted to yield the desired, final concentration. 80 µL of venous serum with added ZIKV was then manually dispensed into each vessel of an SCU, placed into a ZNAT cartridge.

SPU operation and functionality: SPUs were equipped with all necessary mechanical and software components to process ZNAT assay cartridges, including the ability to automate the ZIKV RNA extraction, nucleic acid amplification, and detection processes. These components include an automated, multi-channel liquid handling system, centrifuge, thermal-cycler, 64-well isothermal heat block with an optical sensor and detector laser-emitting diode per well, and network functionality. SPUs were completely enclosed instruments except for a retractable cartridge insertion door and filtered intake/exhaust vents. SPUs were controlled through a touch-screen user interface and were remotely monitored using a secured network connection. ZIKV diagnostic results were transmitted to secured, encrypted, remote servers, collectively known as the Theranos Laboratory Automation System (TLAS), and data retrieved by trained personnel.

Automated RNA Extraction from Blood Samples:

Both serum and CWB samples were first centrifuged and then serum and plasma, respectively, were subjected to lysis, RNA capture onto magnetic beads, washing, and then RNA elution into water.

The SPU added MS2 bacteriophage positive control (Theranos, Palo Alto, Calif.), lithium chloride (Sigma-Aldrich, St. Louis, Mo.), and iodoacetic acid (Santa Cruz Biotechnology, Santa Cruz, Calif.) to blood or serum samples to yield final concentrations of 18.75 plaque-forming units (PFU)/mL, 300 mM, and 150 mM, respectively. Both lithium chloride and iodoacetic acid served as RNase inhibitors. Samples were centrifuged on board the SPU at 1,448 RCF (relative centrifugal force) for 4 min, and 75 µL of supernatant (e.g. plasma in the case of whole blood samples) underwent RNA extraction. Both ZIKV and MS2 bacteriophage in plasma or serum were lysed for 5 min in 450 µL of RNA-extraction lysis/binding buffer (Thermo Fisher, Waltham, Mass.) with 36 µM beta-mercaptoethanol (βME), followed by RNA capture via incubation with 30 µL magnetic beads (Zymo Research, Irvine, Calif.). Beads were captured with a sleeved, magnetic rod and washed in commercial, proprietary wash buffers: 225 µL of wash-1 buffer for 3 min, and 225 µL of wash-2 buffer for 3 min (Thermo Fisher, Waltham Mass.). ZIKV and MS2 RNAs from the magnetic beads were eluted in 50 µL DNase/RNase-free water (Teknova, Hollister, Calif.).

MS2 Phage Preparation:

C3000 bacteria was grown in #271-L media (Luria Bertani medium containing 2% glucose, 53 mM $CaCl_2$, and 0.02% thiamine (vitamin B12) and infected with MS2 bacteriophage (ATCC #15597-B1™, Manassas, Va.) over #271 soft agar media using standard procedures. After 18 h, soft agar media harboring bacteria and phage particles was collected and passed through a 0.2 µm filter. MS2 phage particles were purified through precipitation with 4% PEG8000 and 0.5 M NaCl. MS2 phage particles were pelleted by centrifugation at 6,500×g, followed by resuspension in TMSG buffer (10 mM Tris pH 7.5, 100 mM NaCl, 1 mM $MgCl_2$, 0.1% gelatin, 0.05% $NaN_3$) and storage at 4° C.

Automated Preliminary Amplification:

The liquid handling system within the SPU added 40 µL of extracted RNA to 60 µL of preliminary amplification master mix. Template-negative, DNase/RNase-free water was used in a separate parallel reaction as a negative control. Reaction vessels were overlaid with mineral oil (Sigma, St. Louis, Mo.) and transferred by the sample handling system of the SPU to a thermal-cycling module in the SPU to commence RT-PCR.

The preliminary amplification mix yielded final concentrations of 1× Phusion High-Fidelity buffer (New England Biolabs # B0518S, Ipswich, Mass.), 0.25 mM dNTP, 0.975 mM $MgCl_2$, 0.008 mg/mL reverse-transcriptase (RT, Theranos, Palo Alto, Calif.), 1.25 mg/mL DNA polymerase (D-Pol, Theranos, Palo Alto, Calif.), 0.8 µM of each pre-amp primer against ZIKV, and 0.8 µM of each pre-amp primer against MS2 phage. Thermal-cycling parameters started with 42° C. for 3 min for the reverse transcription reactions. Preliminary amplification utilized one cycle of a denaturation step at 94° C. for 84 sec, annealing step at 62° C. for 33 seconds, extension step at 72° C. for 32 seconds followed by 30 cycles of 94° C. for 5 seconds, 62° C. for 15 seconds and 72° C. for 8 seconds.

Automated Isothermal Amplification and Detection:

Primer pairs contained pair-wise complementary 5' ends that resulted in amplicons containing 5' overhangs. These overhangs facilitated the generation of fluorescently detectable concatemers. Three µL of pre-amplified product (see above) for both sample and negative control were added by the automated liquid handling system into separate wells containing 22 µL of isothermal reaction mix against ZIKV or MS2. ZIKV DNA target amplicon, at $1\times10^6$ copies/mL, was used as an isothermal-specific positive control in a separate well. Assays were invalid if any controls failed (see FIG. 11B, which presents a Table for ZNAT results interpretation).

Isothermal reaction mixes contained a final concentration of 0.64% Tween®-20 (Sigma, St. Louis, Mo.), 160 mM Tris-HCl pH 7.9 (Teknova, Hollister, Calif.), 80 mM $Mg(CH_3COO)_2$ (Sigma, St. Louis, Mo.), 400 mM $CH_3COOK$ (Sigma, St. Louis, Mo.), 8 mM dithiothreitol (DTT) (Teknova, Hollister, Calif.), 400 mM betaine (Sigma, St. Louis, Mo.), 2 µM SYTO®-59 (Thermo Fisher, Waltham, Mass.), 1.6 mM dNTP mix (Sigma, St. Louis, Mo.), 0.097 µM Bst DNA polymerase (Theranos, Palo Alto, Calif.), and 1 µM each of forward and reverse primers (Theranos, Palo Alto, Calif.). Isothermal reactions were overlaid with a melted wax solution comprised of equal parts of 80% isododecane mixture (Alfa Aesar, Ward Hill, Mass.) and melted paraffin wax (Sigma, St. Louis, Mo.) that solidified at room temperature (approximately 22° C.) but melted into an optically-clear liquid after 1 min at 56° C. The isothermal reaction is conducted at 56° C. during which SYTO®-59 relative fluorescence unit (RFU) measurements were taken every minute for 35 minutes within the isothermal module of the SPU. Inflection time calculations were determined from sets of four consecutive time points ($t_0$, $t_1$, $t_2$, $t_3$). If the difference in signal (As) between adjacent time points within a set of time points were greater than a pre-defined threshold, then to was determined as the inflection time.

Zika Target Sequence for ZNAT:

A 101 base-pair region within the Zika polyprotein gene was selected as the target sequence using in-house software algorithms and multiple sequence alignments of available Zika polyprotein gene sequences. This target sequence includes:

(SEQ ID NO: 7)
AAGCCTACCTTGACAAGCAATCAGACACTCAATATGTCTGCAAAAGAAC

GTTAGTGGACAGAGGCTGGGGAAATGGATGTGGACTTTTTGGCAAAGGG

AGC

Notably, this target sequence is present in the genome of Zika strains in the current Brazilian outbreak (e.g. GenBank accession # KU991811, b.p. 1179-1239).

Primers for ZNAT:

Two pairs of primers were designed and synthesized de novo (Theranos, Palo Alto, Calif.) for each target sequence, where one pair was used for preliminary amplification (pre-amplification) via thermocycling and another pair was used for isothermal amplification and detection. Pre-amplification primer pairs were chosen according to their performance at an annealing temperature of 61.5° C. and screened from several primer pairs suggested by in-house software according to given target sequence inputs. Potential isothermal primer pairs were chosen by screening >100 possible primer pairs as suggested by proprietary software, which also determines the most appropriate tail-ends of each primer. Primers were further narrowed down by their specificity in amplifying only the target sequence within human genomic backgrounds without amplifying any target-independent products. The following primers were used:

Pre-Amplification:

```
Zika Forward:
                                    (SEQ ID NO: 8)
5'-AAGCCTACCTTGACAAGC-3'

Zika Reverse:
                                    (SEQ ID NO: 9)
5'-GCTCCCTTTGCCAAAAAG-3'

MS2 phage Forward:
                                    (SEQ ID NO: 10)
5'-ACCAGCATCCGTAGCCTTATT-3'

MS2 phage Reverse:
                                    (SEQ ID NO: 11)
5'-GGACCGCGTGTCTGATCC-3'
```

Isothermal Amplification and Detection:

```
Zika Forward:
                                    (SEQ ID NO: 12)
5'-TTTCCCCATCAGACACTCAATATGT-3'

Zika Reverse:
                                    (SEQ ID NO: 13)
5'-TGGGGAAAGCCAAAAAGTCCACA-3'

MS2 phage Forward:
                                    (SEQ ID NO: 14)
5'-GTGCCCCAGTTCTCCAACGG-3'

MS2 phage Reverse:
                                    (SEQ ID NO: 15)
5'-TGGGGCACTTGTAAGGCGCTGC-3'
```

In-Silico Analysis of Zika Pre-Amplification and Isothermal Primers:

Primer-BLAST (NIH NCBI) was employed as previously published, utilizing the publically available "nr" nucleotide sequence database (Ye J, Coulouris G, Zaretskaya I, Cutcutache I, Rozen S, Madden T L. Primer-BLAST: a tool to design target-specific primers for polymerase chain reaction. BMC Bioinformatics. 2016; 13: 134; Yoshida A, Nagashima S, Ansai T, Tachibana M, Kato H, Watari H, et al. Loop-mediated isothermal amplification method for rapid detection of the periodontopathic bacteria *Porphyromonas gingivalis*, *Tannerella forsythia*, and *Treponema denticola*. J Clin Microbiol. 2005; 43(5): 2418-24). Cross reactivity against each organism was tested explicitly by entering its taxonomy id. Primers with six or more mismatches were constituted as non-reactive. Furthermore, OligoAnalyzer 3.1 (IDT) was used to estimate the decrease in Tm due to mismatches at specific sites. To get a lower bound estimate of the effect of six mismatches, we took the mutation with the smallest influence on Tm at each site, and then sorted by Tm change. The sum of the $\Delta T_m$ for the 6 mutations with the least effect was 15.1° C., at which point we anticipate <1% of the oligonucleotides to be annealed to a target with these six mismatches at the temperature and conditions of the isothermal reaction.

Analytical Sensitivity Study:

The analytical sensitivity study determined the limit of detection (LoD) of ZNAT based on inflection time. The cut-off for the inflection time was defined as the time before >95% of the NTC (no template control) inflections occurred while also being after >90% of the inflection times for ZIKV samples at 1× the limit of detection (LoD). A total of 33 replicates of positive Zika samples at 320 copies/mL (10 PFU/mL) (1× Limit of Detection (LoD) based on the preliminary LoD of 10 PFU/mL) and 40 false positive ZIKV inflections from negative controls among greater than 1,500 assay runs were compiled and considered during determination of the cut-off time. The limit of detection was deemed the lowest viral concentration level corresponding to a detection rate of 95%. Inflections were considered positive as long as they occurred before the cut-off time; the lowest concentration displaying a 100% ZIKV detection rate from at least six replicates was further evaluated by precision testing with 20 or more additional test replicates. Standard qRT-PCR methods with SYBR™ Green Master Mix (Thermo Fisher Scientific #4367659, Waltham Mass.) and de novo synthesized ZIKV gene standards were used to determine a conversion factor from PFU/mL to copies/mL (1 PFU=32.6 copies) for the PRVABC59 strain.

Inclusivity:

Two commercially available ZIKV strains, DakArdD 41662 and MR 766 (Zeptometrix, Buffalo, N.Y.), were tested in ZNAT using SPUs; using the CDC Zika RT-PCR methods; and using an in-house Zika RT-PCR assay at a concentration of 2×LoD in serum.

Analytical Specificity:

A total of 11 pathogens were tested for cross-reactivity based on their taxonomic position (other members of the genus Flavivirus with high sequence homology to ZIKV) and prevalence in South America, including pathogens causing diseases with symptoms such as fever, conjunctivitis, and rash. The 11 pathogens and nine potential interfering substances found in blood were tested in triplicate, added into serum with or without added ZIKV at 2×LoD. Potential blood interfering substances were diluted in their respective diluents and stored at 10× the tested concentration with the exception of the triglyceride mix. The triglyceride mix was stored as a 70× stock because further dilution would require the solvent methanol, which inhibits the ZNAT. The interfering substance stocks were diluted 1:10, or 1:70 for the triglyceride mix, into serum when generating the serum samples for testing.

Nucleic acids were either extracted from cultured viral stocks obtained from commercial vendors or used as inactivated virus. Cross-reactants were added to specific vessel in the cartridge, which then were automatically added into the lysis/binding reaction within SPUs at various concentrations. For 10× and 70× stock preparations, the following interfering substances were diluted as: bilirubin in DMSO; cholesterol in ethanol, gamma globulin in 0.9% NaCl, and human genomic DNA (hgDNA) in TE buffer pH 8.0 (IDT DNA, Coralville, Iowa), and all other potential interfering substances were diluted in DNase/RNase-free water (Teknova, Hollister, Calif.). The substances bilirubin, cholesterol, gamma-globulin, hemoglobin, hgDNA, and triglycerides, were chosen because they are components of human blood and have the potential to interfere with the assay if they are not removed by the sample prep process. The substances EDTA, heparin lithium salt, and sodium citrate are common anti-coagulants used when collecting blood samples. All substance test concentrations, with the exception of the anticoagulants, were recommended by the Clinical Laboratory Standards Institute (CLSI) guideline EP7-A2: Interference Testing Clinical Chemistry. Ten viruses and one parasite tested for analytical specificity were obtained from Zeptometrics and ATCC and all interfering substances we obtained from Sigma-Aldrich. The nucleic acids of nine viruses (excluding parvovirus) and one parasite were extracted from cultured material obtained from vendors using the QIAcube® automated sample prep device using the QIAGEN QIAamp Viral Mini Kit (Qiagen, Hilden, Germany). The purified nucleic acids were quantified through qRT-PCR. Serial ten-fold dilutions of a synthetic RNA or DNA template of known concentration was used to prepare standards for qRT-PCR. Each of the lysates were diluted 10, 100, and 1000 fold from respective stocks. Purified samples were tested in parallel with the standards. Ten-fold serial dilutions of synthetic RNA standards determined a standard curve. Lysates concentrations were determined by extrapolating the concentration values in copies/mL from the standard curve.

CDC RT-PCR Assay:

Based on the protocol provided by CDC (TaqMan Real Time RT-PCR Protocol—25 several modifications were made by CDC to the previously published methods by Lanciotti et al. These include the usage of 5 μL of RNA extract instead of 10 μL. Each of the two assays within the CDC RT-PCR test utilized two separate sets of primers and probes. Each assay utilized RNA extracted from the same blood specimen within two test wells per assay. Positive ZIKV test results were defined by all four test wells yielding Ct values <38. The CDC Zika RT-PCR protocol notes that their test includes two primer/probe sets for the detection of Zika virus RNA. The first set detects all known genotypes of Zika virus; the second, modified set Zika4481/4507cFAM/4552c is specific for Zika virus Asian genotype currently circulating in the Western Hemisphere and is specified below:

```
Zika4481
                                   (SEQ ID NO: 16)
CTGTGGCATGAACCCAATAG Zika4507cFAM
                                   (SEQ ID NO: 17)
CCACGCTCCAGCTGCAAAGG Zika4552c
                                   (SEQ ID NO: 18)
ATCCCATAGAGCACCACTCC
```

Statistical Analyses:

95% confidence intervals (CIs) on PPA and NPA were computed according to equations 15 & 15B under section 10.2.2 in CLSI EP12 A2E guidelines.

In-House Zika rRT-PCR Assay:

Serum samples were processed according to manufacturer's instructions using the QIAcube workstation (Qiagen, Valencia, Calif.). RT-PCR reactions were prepared by adding 1×qPCR Assay QuantiTect Probe RT-PCR master-mix (Qiagen, Valencia, Calif.), 1 μM Zika forward primer

```
(GACATGGCTTCGGACAG (SEQ ID NO: 19))
```

1 μM Zika reverse primer

```
(ATATTGAGTGTCTGATTGCTTG (SEQ ID NO: 20))
```

0.15 μM Zika probe

```
(5'FAM TGCCCAACACAAGGTGAAGCC Dabcyl 3'
(SEQ ID NO: 21))
```

0.25 μM enzyme mix (Qiagen, Valencia, Calif.), 5 μL template. Reactions were run using the following thermocycling program, and monitored in the FAM channel: Reverse transcription step at 50° C. for 30 min, denaturation at 95° C. for 15 sec, followed by 45 cycles of 95° C. for 15 sec, 60° C. for 1 min on the Bio Rad CFX96 Touch™ Real Time PCR Detection System (Bio Rad, Hercules, Calif.).

Run-to-Run (Carry-Over) Contamination Assessment for ZNAT:

Ten consecutive runs were performed on each of five SPUs, where each run alternated between serum samples with ZIKV at $1.3\times10^7$ genomic copies/mL or without ZIKV.

Clinical Study:

ZIKV detection rates in blood samples obtained from Colombia, Dominican Republic, and U.S., including from Zika-symptomatic subjects, were compared between the ZNAT and CDC ZIKV RT-PCR assay. Discordant results between the two assays were further tested with the altona Diagnostics GmbH RealStar® Zika Virus RT-PCR ("altona Diagnostics RealStar®") method (altona Diagnostics, Hamburg, Germany). CDC ZIKV RT-PCR was performed following a modified CDC protocol using serum (Lanciotti R S, Kosoy O L, Laven J J, Velez J O, Lambert A J, Johnson A J, et al. Genetic and serologic properties of Zika virus associated with an epidemic, Yap State, Micronesia, 2007. *Emerg Infect Dis.* 2008; 14(8): 1232-9). The altona Diagnostics RealStar® assay was performed as per manufacturer protocol, using serum or urine. ZIKV RNA extraction was performed on the Qiacube automated device (Qiagen, Hilden, Germany). Thermal-cycling and fluorescent detection was performed on the Bio-Rad C1000 Touch™ with CFX96™ Optical Reaction Module (Bio-Rad, Hercules, Calif.).

Results

Analytical Sensitivity of ZNAT:

The cut-off time of the assay was determined to be the time point before which any inflection was deemed a positive test result (i.e. ZIKV inflection). ZIKV inflection times <40 min were obtained from both true- and false-positives. True-positives comprised 27 serum samples with ZIKV added at 1× of the preliminary LoD while 40 false-positives were collected from >1,500 preliminary test assays. All ZIKV inflections were plotted as a histogram (FIG. 11A). The histogram shown in FIG. 11A is a histogram plot for Cut-off determination for ZNAT, showing a histogram of ZIKV inflections <40 minutes from totals of 40 and 27 venous serum samples, with added ZIKV at 10 plaque-forming units (PFU)/ml (1×LoD (LoD=limit of detection)) or without ZIKV (no template control (NTC)). Receiver operating characteristic (ROC) curve analyses identified 27.0 min as a cut-off time allowing >90% sensitivity (true-positive detection rate) and >95% specificity (true-negatives exclusion rate) in serum samples (FIG. 11A).

ZNAT analytical sensitivity was determined by ZIKV (strain PRVABC59 from the CDC) at various concentrations in serum, including 0, 1, 5, 15, 30, and 60 PFU/mL with equivalent genomic copies of 0, 32, 160, 480, 960, and 1920 copies/mL respectively at n=6 replicates each. 15 PFU/mL (480 copies/mL) was the lowest concentration in serum at which 100% of the results were positive and was further confirmed as the final LoD when it yielded a 95% ZIKV detection rate for 20 additional replicates (FIG. 13, showing analytical sensitivity determination of ZNAT). This method was similarly applied to CWB, which established 10 PFU/mL (320 copies/mL) as the final LoD for yielding 95% positive ZIKV detection rate for 20 replicates (FIG. 13). Taking initial viral titers into consideration, qRT-PCR determined that 10 and 15 PFU/mL corresponded to approximately 327 and 490 copies/mL, respectively (FIG. 12, showing quantification of three ZIKV lysates). As shown in FIG. 12, qRT-PCR was used to convert plaque-forming units (PFU) and half-maximal tissue culture infective dose ($TCID_{50}$) values to number of copies for three different ZIKV lysates. Ten-fold serial dilutions of synthetic RNA standards (indicated by circles) were used to determine a standard curve. Lysates of unknown concentrations tested in parallel are indicated by crosses.

Inclusivity of ZNAT:

In silico analyses were conducted using 109 sequences from 38 publicly available (as of Jun. 1, 2016) ZIKV strains to determine whether ZNAT PCR primer pairs contained complementary sequences. Complete complementation was observed for 31 strains, suggesting that the ZNAT primers should detect these ZIKV strains. The remaining seven strains exhibited at least one base pair mismatch within the primer binding sites, indicating these strains may have decreased detection rates due to incomplete primer-target DNA binding (FIG. 14, a table showing the results of in silico analyses of ZNAT primers against sequenced Zika virus strains). Two of these seven strains, ArD157995 and MR 766, possessed at least two base pair mismatches within primer binding sites (FIG. 14). Of these two mismatch-containing strains, only MR 766 was commercially available to test ZNAT. ZNAT successfully detected both MR 766 and another commercial strain that did not contain any mismatches, DakArD 41662, at 960 copies/mL, in serum samples. In contrast, the CDC ZIKV RT-PCR assay failed to detect either strain in serum samples (FIG. 16). However, Thermos Zika RT-PCR primers successfully detected both strains in the same RNA extracts that the CDC Zika RT-PCR assay failed to detect, ruling out the possibility that the CDC Zika RT-PCR non-detections were due to faulty RNA extraction (FIG. 15, showing, in Table form, reactivity/inclusivity analysis of ZNAT in serum). The concentrations tested for these two strains corresponded to approximately 2× equivalents of the LoD for the CDC ZIKV (PRVABC59) strain, or 980 copies/mL (FIG. 12).

Analytical Specificity of ZNAT:

During primer design, in silico analyses suggested that cross-reactivity against large panels of pathogens with similar genetic sequences or ZIKV-like clinical symptoms was unlikely due to the presence of multiple base pair mismatches between ZNAT primers and target priming sequences (FIG. 16 (a table showing in silico analysis of Zika preliminary amplification and isothermal primers against prevalent diseases with Zika-like onset symptoms) and FIG. 17 (a table showing in silico mismatch analysis of ZNAT primers against potentially cross-reacting organisms)). A panel of organisms bearing significant genetic homology or clinical similarity with ZIKV was tested using ZNAT within serum samples. Tested organisms did not produce any false results when tested using serum samples with or without 2×LoD ZIKV, respectively (FIG. 18, a table showing results of cross-reactivity and interfering substance analyses of ZNAT in serum).

Interfering Substances Analysis of ZNAT:

High concentrations of common components in whole blood, such as cholesterol or hemoglobin, can potentially interfere with assays such as the ZNAT. These components were tested with added ZIKV at 0 or 30 PFU/mL (960 copies/mL) (0 or 2×LoD) in serum. No tested component contributed any observable change in ZIKV detection at 960 copies/mL (2×LoD), or any false positives at 0 copies/mL (0×LoD) of ZIKV (FIG. 19). In addition, the organisms previously tested for cross-reactivity (above) did not produce any false negatives in samples containing 2×LoD ZIKV (FIG. 19).

Run-to-Run (Carry-Over) Contamination Analysis of ZNAT:

To investigate whether sample or amplicon contaminants carried over between consecutive ZNAT device tests, five SPU devices were used in five rounds of paired ZNAT assays. Each round of paired assays consisted of an initial assay of a sample containing high titer ZIKV ($4\times10^5$ PFU/mL, which is $1.3\times10^7$ copies/mL) followed by an assay of a sample lacking ZIKV (0 PFU/mL, which is 0 copies/mL), with all assays utilizing serum. No false-positives were detected for any of the five SPU devices for any of the ZIKV-negative serum samples. This suggested that run-to-run carry-over contamination did not occur, or was not significant (FIG. 20, a table showing the results of analyses of run-to-run contamination of ZNAT in serum).

Concordance Studies:

Serum samples were obtained from 78 U.S. subjects and 102 Dominican Republic and Colombian subjects. Of the samples obtained from Zika-endemic areas, 69 subjects were symptomatic patients whose Zika status were unknown, and 33 were febrile subjects known to be negative on the CDC ZIKV RT-PCR assay. ZIKV was not detected by either the ZNAT or the CDC assays in 78 serum samples from either healthy or febrile subjects from the U.S., where ZIKV infections are currently rare (FIG. 21, a table showing the results of clinical studies using ZNAT). Of the 69 samples that were clinically unknown, the ZNAT detected ZIKV in samples from 39 of 69 subjects, whereas the CDC ZIKV RT-PCR assay detected ZIKV in samples from 17 of 69 subjects (FIG. 21). Samples from the 22 discordant results that were ZNAT positive but CDC ZIKV RT-PCR assay negative were further tested with the FDA EUA-approved altona Diagnostics RealStar® ZIKV RT-PCR assay. The altona Diagnostics assay detected ZIKV in samples from 17 of the 22 discordant sample results (FIG. 21). Furthermore, to gauge the robustness of the ZNAT, the 33 additional serum samples from febrile subjects collected in Colombia, that were first tested as ZIKV-negative by the CDC assay, were tested with exogenously-added ZIKV at different concentrations. The CDC and ZNAT assays yielded 100% ZIKV detection rates for all 33 samples containing exogenously added ZIKV at 480, 960, and 2400 copies/mL (15, 30, and 75 PFU/mL) (FIG. 21).

To calculate the positive and negative percent agreement (PPA and NPA, respectively), test results from the combined CDC RT-PCR with altona assays were used as the reference results. Therefore, the combined CDC RT-PCR and altona assays determined 67 total subjects to be ZIKV-positive (CDC RT-PCR assay detected ZIKV in 17 of 69 subjects, altona confirmed an additional 17 subjects to be ZIKV-positive, and the CDC RT-PCR assay detected all 33 samples with exogenously added ZIKV). The Minilab ZNAA assay likewise detected ZIKV in the same 67 subjects or samples. As the Minilab ZNAA assay detected ZIKV 39 of 69 subjects, five more than the combined CDC RT-PCR and altona assays, these five test results were considered Minilab ZNAA false positives when calculating NPA. When comparing the ZNAT to the CDC Zika RT-PCR assay with confirmation of discrepancies by the altona Diagnostics assay, the ZNAT demonstrated 100% sensitivity (67 of 67 samples [95% CI 94.6-100]) with 95.6% specificity (109 of 114 samples [95% CI 90.1-98.6]) for serum samples (FIG. 21).

Concordance studies were also performed with CWB samples from 77 U.S. and 30 Dominican Republic subjects. As both CDC Zika RT-PCR and altona Diagnostics assays were not cleared for use with capillary whole blood, matched-subject serum and urine specimens were obtained in addition to capillary whole blood samples from Dominican Republic subjects. Specimens from 52 healthy, U.S. subjects tested ZIKV-negative by both the ZNAT and CDC ZIKV RT-PCR assays (FIG. 21). Specimens from 25 additional healthy, U.S. subjects were also prepared with added ZIKV were tested on both the ZNAT and CDC Zika RT-PCR assays. The ZNAT detected ZIKV in 24 of 25 CWB samples with added ZIKV while the CDC Zika RT-PCR assay detected ZIKV in 23 of 25 matched-subject serum samples (FIG. 21). The two samples with added ZIKV that tested ZIKV-positive by ZNAT and ZIKV-negative by CDC RT-PCR testing were confirmed to be ZIKV-positive by altona Diagnostics RealStar® testing (FIG. 21).

Additionally, the ZNAT detected ZIKV in 26 of 30 CWB samples from Dominican Republic subjects with Zika-like clinical symptoms while the CDC Zika RT-PCR assay detected ZIKV in only 5 of 30 matched-subject serum samples (FIG. 21). Samples from all 21 discordant results were confirmed to be ZIKV-positive when using the altona Diagnostics assay on either matched-subject serum or urine samples (FIG. 21). In 10 of these 21 subjects, the altona Diagnostics assay did not detect ZIKV in the serum, but did detect ZIKV in the subject-matched urine samples. The combined CDC RT-PCR and altona assays determined 51 total subjects to be ZIKV-positive (the CDC RT-PCR assay detected ZIKV in 5 Dominican Republic subjects, altona confirmed an additional 21 Dominican Republic subjects to be ZIKV-positive, and the CDC RT-PCR assay detected all 25 samples with exogenously added ZIKV), while the Minilab ZNAA assay detected ZIKV in all of the donor-matched capillary whole blood samples with the exception of one sample from a healthy subject with added ZIKV. When comparing the ZNAT to the CDC Zika RT-PCR assay with discordant subject results confirmed by the altona Diagnostics assay, the ZNAT displayed 98.0% sensitivity (50 of 51 samples [95% CI 89.7-99.7]) and 100.0% specificity (56 of 56 samples [95% CI 93.5-100.0]) for CWB samples.

DISCUSSION

A novel sample-to-result diagnostic assay was developed to detect ZIKV in both venous serum and CWB samples. This assay was performed using a single-use cartridge run on a transportable, fully-automated diagnostic platform (the SPU). The analytical performance of the ZIKV assay was characterized in several studies. Namely, the assay performance was not affected by high concentrations of common, potentially interfering substances, did not demonstrate cross-reactivity with genetically-homologous or clinically-similar pathogens, detected multiple ZIKV strains, and showed no carry-over contamination from high viral load ZIKV samples. The assay had an LoD of 320 and 480 copies/mL for CWB and serum, respectively. The ZNAT has a LoD that is at least similar to the CDC ZIKV RT-PCR assay. Indeed, the ZNAT identified ZIKV in more symptomatic subjects from Zika-prevalent areas than did the CDC ZIKV RT-PCR test. Of these 22 samples, 17 were subsequently confirmed as ZIKV-positive using a third, FDA-approved, altona Diagnostics RealStar® ZIKV RT-PCR assay (FIG. 21). ZNAT also detected ZIKV in samples from symptomatic subjects that the altona Diagnostics assay failed to detect as having ZIKV, which suggests that ZNAT either has greater sensitivity, is more inclusive for Zika strains, or has lower specificity than the altona Diagnostics assay. However, the complete lack of false positive results among the serum and CWB samples collected from healthy or febrile U.S. subjects and tested by ZNAT argues against a lack of specificity.

ZNAT detected ZIKV in capillary whole blood specimens from 21 subjects while the CDC ZIKV RT-PCR assay did not detect ZIKV in matched-subject serum specimens from the same subjects. All 21 patients were confirmed ZIKV-positive when their respective serum or urine samples were tested by the altona Diagnostics assay (FIG. 21). While ZNAT detected in these 21 CWB specimens, the altona Diagnostics assay detected ZIKV in 11 of 21 serum specimens. The altona Diagnostics assay only confirmed the remaining 10 patients to be ZIKV-positive when their urine specimens were tested.

The present example demonstrates that the ZNAT can detect ZIKV in CWB with sensitivities similar to serum, thereby obviating a need for venipuncture. Implementing fingerstick phlebotomy to provide CWB samples that can be stably transported will aid in expanding ZIKV diagnostics, particularly in centralized testing locations and for pregnant women and neonates. Rapid ZIKV testing with increased accessibility can help women better prepare for pregnancies and guide expectant mothers in managing their pregnancies. Combining protein-based or antibody-based, serologic ZIKV tests in parallel with ZNAT diagnostics in the same platform may distinguish active from cleared ZIKV infections.

FIG. 22—The Nucleic Acid Amplification based assays were run on the detection system shown in this figure. This part of the module opens to contain 64 discrete wells, capable of running 64 discrete reactions including controls for a given assay. The thermocycler module is on the bottom left, and above it is an isothermal detector. The diagram on the right of FIG. 22 shows a cross-section of the isothermal detector. The fluorescence based isothermal detector (shown at the upper left of the figure) has dimensions of 2.5 inches high by 5.4 inches wide by 13.1 inches long. The thermocycler module (shown at the lower left of the figure) has dimensions of 3.9 inches high by 5.7 inches wide by 8.5 inches long. There are series of sample vessels in the middle where the path of the excitation LED can shine through the sample and be detected as a fluorescent signal. Nucleic Acid Amplification-based assays may use a thermocycler module as shown on the bottom left of FIG. 22; a fluorescence-based isothermal detection module is shown above the thermocycler module. The fluorescence-based isothermal detection module is capable of running 64 separate, distinct reactions, including controls for a given assay.

A cross sectional diagram overview of the isothermal detector is shown on the right of FIG. 22. A series of sample vessels are shown in the middle row where the light path of the excitation LEDs shines through the sample and then may be detected as a fluorescent signal by an array of photodetectors at the bottom. For the Zika assay, measurements are taken every minute for 35 minutes in order to detect an inflection point in the fluorescent signal. An image depicting an idealized plot of fluorescence measurements taken periodically during the course of multiple thermal cycles is shown as an inset in FIG. 22.

FIG. 23A provides information regarding a novel isothermal nucleic acid amplification method for use with sample analysis devices and systems. In embodiments using automated sample analysis devices and systems as disclosed herein, all of the sample prep may be automated and performed on board automated sample analysis devices using a magnetic bead based extraction method performed using a sample handling systems or a fluid handling system as disclosed herein. The amplification method is a combination of a thermal cycle based pre-amplification step, and then an isothermal amplification and detection step, according to methods disclosed herein. The high sensitivity is driven in part by a highly efficient on-board sample extraction process. Primers were designed using multisequence gene alignment.

The assay method employed by the automated assay device for the Zika assay is an isothermal nucleic acid amplification method according to the methods disclosed herein which requires 75 microliters of plasma or serum. All of the sample prep was automated on the automated assay device and performed using a magnetic bead-based extraction method. The assay method used a combination of a PCR-based pre-amplification step, followed by an isothermal amplification and detection step. The high sensitivity of the assay was driven in part by a highly efficient automated on-board sample extraction process performed by the automated assay device. The primers used in the nucleic acid amplification Zika assay were designed from a consensus of a multi-sequence alignment of all Zika strains deposited in GenBank. The selected gene target was a 100-base pair region within the highly conserved polyprotein gene.

As shown in FIG. 23B, Applicant presents results for analytical sensitivity, specificity, and inclusivity to show the robustness of the platform. Additionally, a clinical study was performed to demonstrate concordance with reference methods.

As shown in FIG. 24 the Zika assay sensitivity is shown here using a Zika strain from the Centers for Disease Control (CDC) that is of Asian lineage from the recent Zika outbreak. The LoD was determined by testing Zika virus across a range of concentrations in serum, from 0 to 1920 copies per mL. The LoD was determined to be 480 copies/mL and was verified by testing 20 additional replicates. For reference this is twice as sensitive as the published LoD for the CDC Zika test.

As shown in FIG. 25, Applicant tested a panel of organisms that are genetically or clinically similar to Zika, at very high concentrations, both in the absence and presence of the Zika virus, in order to confirm the analytical specificity of the assay. As shown in the middle columns, there was no cross reactivity for any of the organisms tested. These organisms did not cause any significant interference with the detection of Zika virus, as shown in the columns to the right.

As shown in FIG. 26, there was no cross-reactivity or interference detected for any of the common potentially interfering substances, as listed in the Table shown in FIG. 6.

Inclusivity data is shown in FIG. 27A, illustrating results from the NAA Zika test and the CDC assay. As shown in FIG. 27A, the NAA Zika test was able to detect these two additional Zika virus strains (of African lineage) while the CDC test did not.

The assays carried out using the methods and devices disclosed herein showed no significant carry-over between runs of testing on the same device. In these carryover studies, samples were tested with very high concentrations of Zika virus and then run a using negative control sample. As shown in FIG. 27B, no false positives were detected for any of the negative controls, demonstrating no carry-over or cross contamination between runs. This illustrates an advantage of the single-use cartridge format disclosed herein, in which a cartridge with completely sealed consumables is provided to the automated sample analysis device, and in which the sample, which is also provided in the cartridge, does not come in direct contact with the instrument but is instead provided on, and carried by, the cartridge.

As shown in FIG. 28, samples were collected from 181 subjects, from South America and the U.S., in order to evaluate clinical performance of the assays. 78 of the subjects were from the US—both healthy and febrile, and 103 were from the Dominican Republic and Colombia and presented with Zika symptoms. In order to ensure there were enough positive samples to compute percent agreements, the 39 naturally positive samples were supplemented with 33 additional samples to which Zika virus was added. To calculate percent agreement, the NAA Zika assay was compared to the CDC RT-PCR assay and also to the altona kit, which has received emergency use authorization (EUA).

FIG. 29 provides a comparison between the NAA Zika Assay and the CDC RT-PCR, with confirmation by the altona assay for both negative and positive percent agreement along with the 95% confidence interval. The NAA Zika assay shows a high level of concordance with the reference methods. These results demonstrate that the automated sample analysis devices disclosed herein can automatically perform molecular testing with fully integrated assay and results processing, comparable to methods that require highly trained personnel.

FIG. 30 provides an overview of some of the criteria of a clinical study performed using the NAA Zika Assay disclosed herein on capillary blood samples. Capillary samples were prospectively collected from healthy or symptomatic subjects in the US or Dominican Republic, respectively, and shipped in small containers (Nanotainer™) to the United States for analysis on the automated sample analysis devices ("minilabs") as disclosed herein. Capillary whole blood samples were tested on 20 minilabs while venous serum and urine samples were tested using the CDC or Altona methods.

As shown in FIG. 31, the NAA Zika Assay using capillary whole blood samples on the miniLab showed a high level of concordance with the comparator methods. There was only a single sample with added Zika virus that was detected as negative by CDC but positive by Altona that was detected by the miniLab NAA Zika test as negative. The NAA Zika Assay performed using the miniLab is believed to be the only Zika test that can use capillary blood.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. For example, a feature of one embodiment may be combined with a feature of another embodiment, whether such combination is described herein or not. It should also be understood that while the invention provided herein has been described herein using a limited number of terms and phrases for purposes of expediency, the invention could also be described using other terms and phrases not provided herein which also accurately describe the invention.

Additionally, although some embodiments herein may describe the initial thermal cycling as a "PCR" process, many embodiments herein may perform only a thermal cycling style processing and not any type of detection during the initial "PCR" process. In embodiments, it should be understood that other processes that provide an increased number of copy numbers may be used for the initial sample enrichment. The term "initial" as used in the examples herein does not necessarily imply that it is the first step, but merely that it occurs before one or more follow-up detection step(s). Some embodiments may view this as a pre-amplification step. Some embodiments may view this as a sample enrichment step.

In embodiments, it should also be understood that the initial thermal cycling process may be performed on a bulk portion and/or common portion of the sample with a plurality of different binder types therein (ebola, malaria, etc. . . . ) for a plurality of different loci, wherein post-thermal cycling, the process may be processed for more specific detection such as but not limited to DNA amplification or other detection processing currently known or may be developed in the future. In such embodiments where there is bulk processing of sample with a plurality of different binders, it should be understood that detection in the initial stage, although not specifically excluded, such detection is generally not done due the variety of different binders in the sample that may or may not yield actionable data. In embodiments, the hybrid process can be configured to detect many targets from a single common sample that is enriched, wherein the targets may be at least 5 or more. In embodiments, the process may detect many targets from a single sample, wherein the targets may be at least 7 or more. In embodiments, the process may detect many targets from a single sample, wherein the targets may be at least 10 or more. In embodiments, the process may detect many targets from a single sample, wherein the targets may be at least 20 or more.

In embodiments, the hybrid process herein may improve sensitivity of the isothermal process, at least in part due to the increase in copy numbers from the initial thermal cycling, but also provides better specificity than PCR specificity, in part because of the use of at least two different primers (for example, primer in thermal cycling process and primer in the isothermal process). In embodiments, the initial process may be coarser for the thermal cycling step for enriching for the target(s) and not necessarily for detection during the initial processing. In embodiments, the initial processing may create non-specific product (along with creating more copies of the target material) and the processing of the sample in subsequent step provides at least a second layer of detection that is more specific for the desired target(s) but having the benefit of more copies to detect due to the enrichment from the initial step (even if creating some non-specific product in the process). In embodiments, the secondary or other later detection process of the hybrid process may be viewed as an end point detection that is sequence specific. In embodiments, the hybrid process may be better than either a PCR process or isothermal process individually in terms of sensitivity and specificity In embodiments, some may use parallel track processing wherein at least one portion of the initial sample is processed along one track using the hybrid process and at least another portion is processed on at least one other track such as but not limited to another PCR process or an isothermal detection process. Because it may be the case that it is unknown if the sample has sufficient copy numbers of a target in the sample, some situations may occur where pre-amplification is not needed for detection to occur in one of the non-hybrid processing tracks, particularly if copy numbers are sufficient without sample enrichment. If one track returns a signal sooner, the process may be stopped earlier if a sufficient response is received on one track that reduces the need to continue detection along one of the other parallel tracks. In embodiments, a sample processing device may include at least one thermal cycler and at least one non-cycling heater. Optionally, some embodiments may have multiple thermal cyclers wherein at one can be controlled not to cycle. In embodiments, some embodiments may have a thermal cycler with fewer wells, chambers, or vessels for thermal cycling that the subsequent detection process, but optionally, each may be configured to hold larger volumes than the wells of the follow-on detection method. Thus, one embodiment may have one or two wells, chambers, or vessels for thermal cycling and at least 10 or more wells, chambers, or vessels for the follow-on detection, where each well, chamber, or vessel may be more specific for certain loci. In such an embodiment, a division of the sample into smaller aliquots may occur after the initial thermal cycling step that enriches the sample. In one embodiments, a control sample may also be thermal cycled for control purposes.

It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. The appended claims are not to be interpreted as including means-plus-function limitations, unless such a limitation is explicitly recited in a given claim using the phrase "means for." As used in the description herein and through the claims that follow, a first object described as containing "at least a portion" of a second object may contain the full amount of/the complete second object.

As used in the description herein and throughout the claims that follow, the terms "comprise", "include", and "contain" and related tenses are inclusive and open-ended, and do not exclude additional, unrecited elements or method steps. Also, the presence of broadening words and phrases such as "one or more," "at least," "but not limited to" or other like phrases in some instances shall not be read to mean that the narrower case is intended or required in instances where such broadening phrases may be absent. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction by anyone of the patent documents or the patent disclosure, as they appear in the US Patent and Trademark Office patent file or records, but otherwise reserves all copyright rights whatsoever. The following notice shall apply: Copyright 2013-16 Thermos, Inc.

The invention claimed is:

1. A method for amplifying a polynucleotide template, the method comprising:
   A) generating multiple copies of a polynucleotide template in a polymerase chain reaction (PCR) amplification reaction mixture, wherein the sample is derived from capillary whole blood wherein the PCR amplification reaction mixture comprises a first PCR amplification reaction primer and a second PCR amplification reaction primer, wherein in the PCR amplification reaction mixture, the first PCR amplification reaction primer anneals to the polynucleotide template and the second PCR amplification reaction primer anneals to a polynucleotide which is complementary to the polynucleotide template, and wherein in the PCR amplification reaction mixture, multiple copies of a PCR amplification reaction product are formed, wherein the PCR amplification reaction product is a double-stranded nucleic acid molecule comprising a first strand and a second strand, and wherein a first strand of the PCR amplification reaction product is a copy of the polynucleotide template;
   B) incubating copies of the polynucleotide template in a non-thermocycling reaction mixture comprising a non-thermocycling reaction first primer and a non-thermocycling reaction second primer, wherein:
   the polynucleotide template comprises a first portion, a second portion and a third portion, wherein the third portion is situated in the polynucleotide template between the first portion and the second portion;
   the first primer comprises a first region and a second region, wherein the second region of the first primer is complementary to the first portion of the polynucleotide template; and the second primer comprises a first region and a second region, wherein the second region of the second primer is complementary to a sequence in the PCR amplification reaction product second strand which is complementary to the second portion of the polynucleotide template, the first region of the second primer is complementary to the first region of the first primer, and the first region of the second primer is complementary to the third portion of the polynucleotide template.

2. The method of claim 1, wherein the first portion and second portion of the polynucleotide template are each between 6 and 30 nucleotides in length.

3. The method of claim 1, wherein the third portion of the polynucleotide template is between 4 and 14 nucleotides in length.

4. A method for amplifying a polynucleotide template, the method comprising:
   A) generating multiple copies of a polynucleotide template in a polymerase chain reaction (PCR) amplification reaction mixture, wherein the sample is derived from capillary whole blood wherein the PCR amplification reaction mixture comprises a first PCR amplification reaction primer and a second PCR amplification reaction primer, wherein in the PCR amplification reaction mixture, the first PCR amplification reaction primer anneals to the polynucleotide template and the second PCR amplification reaction primer anneals to a polynucleotide which is complementary to the polynucleotide template, and wherein in the PCR amplification reaction mixture, multiple copies of a PCR amplification reaction product are formed, wherein the PCR amplification reaction product is a double-stranded nucleic acid molecule comprising a first strand and a second strand, and wherein a first strand of the PCR amplification reaction product is a copy of the polynucleotide template; B) incubating copies of the polynucleotide template in a non-thermocycling reaction mixture comprising a non-thermocycling reaction first primer and a non-thermocycling reaction second primer, wherein:

the polynucleotide template comprises a first portion, a second portion and a third portion, wherein the third portion is situated in the polynucleotide template between the first portion and the second portion;

the first primer comprises a first region and a second region, wherein the second region of the first primer is complementary to the first portion of the polynucleotide template; and the second primer comprises a first region and a second region, wherein the second region of the second primer is complementary to a sequence in the PCR amplification reaction product second strand which is complementary to the second portion of the polynucleotide template, the first region of the second primer is complementary to the first region of the first primer, and the first region of the second primer is complementary to the third portion of the polynucleotide template;

wherein the number of copies of the polynucleotide template in the non-thermocycling reaction mixture is increased at least 10-fold within 60 minutes of initiation of the method.

5. A method for amplifying a polynucleotide template, the method comprising:

A) generating multiple copies of a polynucleotide template in a polymerase chain reaction (PCR) amplification reaction mixture, wherein the sample is derived from capillary whole blood wherein the PCR amplification reaction mixture comprises a first PCR amplification reaction primer and a second PCR amplification reaction primer, wherein in the PCR amplification reaction mixture, the first PCR amplification reaction primer anneals to the polynucleotide template and the second PCR amplification reaction primer anneals to a polynucleotide which is complementary to the polynucleotide template, and wherein in the PCR amplification reaction mixture, multiple copies of a PCR amplification reaction product are formed, wherein the PCR amplification reaction product is a double-stranded nucleic acid molecule comprising a first strand and a second strand, and wherein a first strand of the PCR amplification reaction product is a copy of the polynucleotide template; B) incubating copies of the polynucleotide template in a non-thermocycling reaction mixture comprising a non-thermocycling reaction first primer and a non-thermocycling reaction second primer, wherein:

the polynucleotide template comprises a first portion, a second portion and a third portion, wherein the third portion is situated in the polynucleotide template between the first portion and the second portion;

the first primer comprises a first region and a second region, wherein the second region of the first primer is complementary to the first portion of the polynucleotide template; and the second primer comprises a first region and a second region, wherein the second region of the second primer is complementary to a sequence in the PCR amplification reaction product second strand which is complementary to the second portion of the polynucleotide template, the first region of the second primer is complementary to the first region of the first primer, and the first region of the second primer is complementary to the third portion of the polynucleotide template;

wherein a concatemer strand comprising at least three copies of the polynucleotide template is generated during the incubation of the non-thermocycling reaction mixture.

\* \* \* \* \*